(12) United States Patent
Zurfluh et al.

(10) Patent No.: US 6,358,505 B1
(45) Date of Patent: Mar. 19, 2002

(54) G-CSF RECEPTOR AGONISTS

(76) Inventors: Linda Zurfluh, 126 E. Maple, Kirkwood, MO (US) 63122; Barbara Klein, 12917 Topping Estates, St. Louis, MO (US) 63131; Charles McWherter, 16564 Thunderhead Canyon Ct., Wildwood, MO (US) 63011; Yiping Feng, 423 Mission Ct., St. Louis, MO (US) 63130; John McKearn, 18612 Babler Meadow Dr., Glencoe, MO (US) 63038; Sarah Braford-Goldberg, 4111 W. Pine #10, St. Louis, MO (US) 63108

( * ) Notice: Subject to any disclaimer, the term of this patent is extended or adjusted under 35 U.S.C. 154(b) by 0 days.

(21) Appl. No.: 09/344,837

(22) Filed: Jun. 25, 1999

Related U.S. Application Data

(60) Division of application No. 08/833,167, filed on Apr. 4, 1997, now Pat. No. 6,100,070, which is a continuation-in-part of application No. PCT/US96/15935, filed on Oct. 4, 1996.
(60) Provisional application No. 60/004,382, filed on Sep. 27, 1995.

(51) Int. Cl.$^7$ .................. A61K 38/00; A61K 39/00; G01N 33/566
(52) U.S. Cl. ................ 424/85.1; 435/7.2; 424/185.1; 424/192.1; 514/2
(58) Field of Search ............... 514/2; 435/7.2; 424/185.1, 85.1, 192.1

(56) References Cited

PUBLICATIONS

Duhrsen et al. Effects of Recombinant Human Granulocyte Colony–Strimulating Factor on Hematopoietic Progenitor Cells in Cancer Patients. Blood vol. 72, No. 6 pp. 2074–2081, 1988.*

* cited by examiner

*Primary Examiner*—Prema Mertz
*Assistant Examiner*—Joseph F. Murphy
(74) *Attorney, Agent, or Firm*—S. Christopher Bauer

(57) ABSTRACT

Disclosed are novel G-CSF receptor agonist proteins, DNAs which encode the multi-functional hematopoietic receptor agonists proteins, methods of making the multi-functional hematopoietic receptor agonists proteins and methods of using the multi-functional hematopoietic receptor agonists proteins.

15 Claims, 4 Drawing Sheets

Sequence Rearranged Protein

Native Protein

I. Construct tandemly-duplicated template

II. PCR-amplify tandemly-duplicated template

SEQUENCE LISTING (1) GENERAL INFORMATION:

(iii) NUMBER OF SEQUENCES: 129

(2) INFORMATION FOR SEQ ID NO:1:

(i) SEQUENCE CHARACTERISTICS:
        (A) LENGTH: 174 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: Modified-site
        (B) LOCATION: 1
        (D) OTHER INFORMATION: /note= "Xaa at position 1 is Thr,
            Ser, Arg, Tyr or Gly;"

(ix) FEATURE:
        (A) NAME/KEY: Modified-site
        (B) LOCATION: 2
        (D) OTHER INFORMATION: /note= "Xaa at position 2 is Pro or
            Leu;"

(ix) FEATURE:
        (A) NAME/KEY: Modified-site
        (B) LOCATION: 3
        (D) OTHER INFORMATION: /note= "Xaa at position 3 is Leu,
            Arg, Tyr or Ser;"

(ix) FEATURE:
        (A) NAME/KEY: Modified-site
        (B) LOCATION: 13
        (D) OTHER INFORMATION: /note= "Xaa at position 13 is Phe,
            Ser, His, Thr or Pro;"

(ix) FEATURE:
        (A) NAME/KEY: Modified-site
        (B) LOCATION: 16
        (D) OTHER INFORMATION: /note= "Xaa at position 16 is Lys,
            Pro, Ser, thr or His;"

(ix) FEATURE:
        (A) NAME/KEY: Modified-site
        (B) LOCATION: 17
        (D) OTHER INFORMATION: /note= "Xaa at position 17 is Cys,
            Ser, Gly, Ala, Ile, Tyr or Arg;"

(ix) FEATURE:
        (A) NAME/KEY: Modified-site
        (B) LOCATION: 18
        (D) OTHER INFORMATION: /note= "Xaa at position 18 is Leu,
            Thr, Pro, His, Ile or Cys;"

(ix) FEATURE:
        (A) NAME/KEY: Modified-site
        (B) LOCATION: 22
        (D) OTHER INFORMATION: /note= "Xaa at position 22 is Arg,
            Tyr, Ser, Thr or Ala;"

(ix) FEATURE:
        (A) NAME/KEY: Modified-site
        (B) LOCATION: 24
        (D) OTHER INFORMATION: /note= "Xaa at position 24 is Ile,
            Pro, Tyr or Leu;"

(ix) FEATURE:
        (A) NAME/KEY: Modified-site
        (B) LOCATION: 27
        (D) OTHER INFORMATION: /note= "Xaa at position 27 is Asp,
            or Gly;"

(ix) FEATURE:

```
          (A) NAME/KEY: Modified-site
          (B) LOCATION: 30
          (D) OTHER INFORMATION: /note= "Xaa at position 30 is Ala,
              Ile, Leu or Gly;"

(ix) FEATURE:
          (A) NAME/KEY: Modified-site
          (B) LOCATION: 34
          (D) OTHER INFORMATION: /note= "Xaa at position 34 is Lys
              or Ser;"

(ix) FEATURE:
          (A) NAME/KEY: Modified-site
          (B) LOCATION: 36
          (D) OTHER INFORMATION: /note= "Xaa at position 36 is Cys
              or Ser;"

(ix) FEATURE:
          (A) NAME/KEY: Modified-site
          (B) LOCATION: 42
          (D) OTHER INFORMATION: /note= "Xaa at position 42 is Cys
              or Ser;"

(ix) FEATURE:
          (A) NAME/KEY: Modified-site
          (B) LOCATION: 43
          (D) OTHER INFORMATION: /note= "Xaa at position 43 is His,
              Thr, Gly, Val, Lys, Trp, Ala, Arg, Cys, or Leu;"

(ix) FEATURE:
          (A) NAME/KEY: Modified-site
          (B) LOCATION: 44
          (D) OTHER INFORMATION: /note= "Xaa at position 44 is Pro,
              Gly, Arg, Asp, Val, Ala, His, Trp, Gln, or Thr;"

(ix) FEATURE:
          (A) NAME/KEY: Modified-site
          (B) LOCATION: 46
          (D) OTHER INFORMATION: /note= "Xaa at position 46 is Glu,
              Arg, Phe, Arg, Ile or Ala;"

(ix) FEATURE:
          (A) NAME/KEY: Modified-site
          (B) LOCATION: 47
          (D) OTHER INFORMATION: /note= "Xaa at position 47 is Leu
              or Thr;"

(ix) FEATURE:
          (A) NAME/KEY: Modified-site
          (B) LOCATION: 49
          (D) OTHER INFORMATION: /note= "Xaa at position 49 is Leu,
              Phe, Arg or Ser;"

(ix) FEATURE:
          (A) NAME/KEY: Modified-site
          (B) LOCATION: 50
          (D) OTHER INFORMATION: /note= "Xaa at position 50 is Leu,
              Ile, His, Pro or Tyr;"

(ix) FEATURE:
          (A) NAME/KEY: Modified-site
          (B) LOCATION: 54
          (D) OTHER INFORMATION: /note= "Xaa at position 54 is Leu
              or His;"

(ix) FEATURE:
          (A) NAME/KEY: Modified-site
          (B) LOCATION: 64
          (D) OTHER INFORMATION: /note= "Xaa at position 64 is Cys
              or Ser;"

(ix) FEATURE:
          (A) NAME/KEY: Modified-site
          (B) LOCATION: 67
          (D) OTHER INFORMATION: /note= "Xaa at position 67 is Gln,
              Lys, Leu or Cys;"

(ix) FEATURE:
          (A) NAME/KEY: Modified-site
```

```
          (B) LOCATION: 70
          (D) OTHER INFORMATION: /note= "Xaa at position 70 is Gln,
              Pro, Leu, Arg or Ser;"

(ix) FEATURE:
          (A) NAME/KEY: Modified-site
          (B) LOCATION: 74
          (D) OTHER INFORMATION: /note= "Xaa at position 74 is Cys
              or Ser;"

(ix) FEATURE:
          (A) NAME/KEY: Modified-site
          (B) LOCATION: 104
          (D) OTHER INFORMATION: /note= "Xaa at position 104 is Asp,
              Gly or Val;"

(ix) FEATURE:
          (A) NAME/KEY: Modified-site
          (B) LOCATION: 108
          (D) OTHER INFORMATION: /note= "Xaa at position 108 is Leu,
              Ala, Val, Arg, Trp, Gln or Gly;"

(ix) FEATURE:
          (A) NAME/KEY: Modified-site
          (B) LOCATION: 115
          (D) OTHER INFORMATION: /note= "Xaa at position 115 is Thr,
              His, Leu or Ala;"

(ix) FEATURE:
          (A) NAME/KEY: Modified-site
          (B) LOCATION: 120
          (D) OTHER INFORMATION: /note= "Xaa at position 120 is Gln,
              Gly, Arg, Lys or His"

(ix) FEATURE:
          (A) NAME/KEY: Modified-site
          (B) LOCATION: 123
          (D) OTHER INFORMATION: /note= "Xaa at position 123 is Glu,
              Arg, Phe or Thr"

(ix) FEATURE:
          (A) NAME/KEY: Modified-site
          (B) LOCATION: 144
          (D) OTHER INFORMATION: /note= "Xaa at position 144 is Phe,
              His, Arg, Pro, Leu, Gln or Glu;"

(ix) FEATURE:
          (A) NAME/KEY: Modified-site
          (B) LOCATION: 146
          (D) OTHER INFORMATION: /note= "Xaa at position 146 is Arg
              or Gln;"

(ix) FEATURE:
          (A) NAME/KEY: Modified-site
          (B) LOCATION: 147
          (D) OTHER INFORMATION: /note= "Xaa at position 147 is Arg
              or Gln;"

(ix) FEATURE:
          (A) NAME/KEY: Modified-site
          (B) LOCATION: 156
          (D) OTHER INFORMATION: /note= "Xaa at position 156 is His,
              Gly or Ser;"

(ix) FEATURE:
          (A) NAME/KEY: Modified-site
          (B) LOCATION: 159
          (D) OTHER INFORMATION: /note= "Xaa at position 159 is Ser,
              Arg, Thr, Tyr, Val or Gly;"

(ix) FEATURE:
          (A) NAME/KEY: Modified-site
          (B) LOCATION: 162
          (D) OTHER INFORMATION: /note= "Xaa at position 162 is Glu,
              Leu, Gly or Trp;"

(ix) FEATURE:
          (A) NAME/KEY: Modified-site
          (B) LOCATION: 163
```

(D) OTHER INFORMATION: /note= "Xaa at position 163 is Val,
            Gly, Arg or Ala;"

(ix) FEATURE:
        (A) NAME/KEY: Modified-site
        (B) LOCATION: 169
        (D) OTHER INFORMATION: /note= "Xaa at position 169 is Arg,
            Ser, Leu, Arg or Cys;"

(ix) FEATURE:
        (A) NAME/KEY: Modified-site
        (B) LOCATION: 170
        (D) OTHER INFORMATION: /note= "Xaa at position 170 is His,
            Arg or Ser;"

(xi) SEQUENCE DESCRIPTION: SEQ ID NO:1:

Xaa Xaa Xaa Gly Pro Ala Ser Ser Leu Pro Gln Ser Xaa Leu Leu Xaa
1               5                   10                  15

Xaa Xaa Glu Gln Val Xaa Lys Xaa Gln Gly Xaa Gly Ala Xaa Leu Gln
            20                  25                  30

Glu Xaa Leu Xaa Ala Thr Tyr Lys Leu Xaa Xaa Xaa Glu Xaa Xaa Val
        35                  40                  45

Xaa Xaa Gly His Ser Xaa Gly Ile Pro Trp Ala Pro Leu Ser Ser Xaa
50                  55                  60

Pro Ser Xaa Ala Leu Xaa Leu Ala Gly Xaa Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Xaa Thr Leu Gln Xaa Asp Val Ala Asp
                100                 105                 110

Phe Ala Xaa Thr Ile Trp Gln Xaa Met Glu Xaa Xaa Gly Met Ala Pro
        115                 120                 125

Ala Leu Gln Pro Thr Gln Gly Ala Met Pro Ala Phe Ala Ser Ala Xaa
        130                 135                 140

Gln Xaa Xaa Ala Gly Gly Val Leu Val Ala Ser Xaa Leu Gln Xaa Phe
145                 150                 155                 160

Leu Xaa Xaa Ser Tyr Arg Val Leu Xaa Xaa Leu Ala Gln Pro
                165                 170

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Gly Gly Gly Ser
1

(2) INFORMATION FOR SEQ ID NO:3:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:3:

GCTCTGAGAG CCGCCAGAGC CGCCAGAGGG CTGCGCAAGG TGGCGTAGAA CGCG        54

(2) INFORMATION FOR SEQ ID NO:4:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:4:

CAGCCCTCTG GCGGCTCTGG CGGCTCTCAG AGCTTCCTGC TCAAGTCTTT AGAG        54

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:5:

GGGCTGCGCA AGGTGGCG        18

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:6:

ACACCATTGG GCCCTGCCAG C        21

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:7:

GATCGACCAT GGCTTACAAG CTGTGCCACC CC        32

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:8:

CGATCGAAGC TTATTAGGTG GCACACAGCT TCTCCT                                   36

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:9:

GATCGACCAT GGCTCCCGAG TTGGGTCCCA CC                                       32

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:10:

CGATCGAAGC TTATTAGGAT ATCCCTTCCA GGGCCT                                   36

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:11:

GATCGACCAT GGCTATGGCC CCTGCCCTGC AG                                       32

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:12:

CGATCGAAGC TTATTATCCC AGTTCTTCCA TCTGCT                                   36

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:13:

GATCGACCAT GGCTACCCAG GGTGCCATGC CG                              32

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:14:

CGATCGAAGC TTATTAGGGC TGCAGGGCAG GGGCCA                          36

(2) INFORMATION FOR SEQ ID NO:15:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:15:

GATCGACCAT GGCTTCTGCT TTCCAGCGCC GG                              32

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:16:

CGATCGAAGC TTATTAGGCG AAGGCCGGCA TGGCAC                          36

(2) INFORMATION FOR SEQ ID NO:17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:17:

ATATCCATGG CTCCGGAACT GGGTCCAACT CTG                             33

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "DNA (synthetic)"

(xi) SEQUENCE DESCRIPTION: SEQ ID NO:18:

ACCTCCAGGA AGCTCTGCAG ATGG                                              24

(2) INFORMATION FOR SEQ ID NO:19:

(i) SEQUENCE CHARACTERISTICS:
         (A) LENGTH: 65 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:19:

TATATCCATG GCTATGGCTC CAGCTCTGCA ACCAACTCAA GGTGCAATGC CAGCATTTGC        60

ATCTG                                                                   65

(2) INFORMATION FOR SEQ ID NO:20:

(i) SEQUENCE CHARACTERISTICS:
         (A) LENGTH: 63 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:20:

GATGGCTAGC AACCAGAACA CCACCTGCAC GACGTTGAAA AGCAGATGCA AATGCTGGCA        60

TTG                                                                     63

(2) INFORMATION FOR SEQ ID NO:21:

(i) SEQUENCE CHARACTERISTICS:
         (A) LENGTH: 57 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:21:

TATATCCATG GCTACTCAAG GTGCTATGCC AGCTTTTGCT TCTGCTTTTC AACGTCG           57

(2) INFORMATION FOR SEQ ID NO:22:

(i) SEQUENCE CHARACTERISTICS:
         (A) LENGTH: 58 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA (synthetic)"

(xi) SEQUENCE DESCRIPTION: SEQ ID NO:22:

GCAGATGGCT AGCAACCAGA ACACCACCTG CACGACGTTG AAAAGCAGAA GCAAAAGC          58

(2) INFORMATION FOR SEQ ID NO:23:

(i) SEQUENCE CHARACTERISTICS:
         (A) LENGTH: 44 base pairs

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:23:

CATGGCTTCT GCTTTTCAAC GTCGTGCAGG TGGTGTTCTG GTTG                 44

(2) INFORMATION FOR SEQ ID NO:24:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:24:

CTAGCAACCA GAACACCACC TGCACGACGT TGAAAAGCAG AAGC                 44

(2) INFORMATION FOR SEQ ID NO:25:

(i) SEQUENCE CHARACTERISTICS:
        (A) LENGTH: 525 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:25:

ATGGCTTACA AGCTGTGCCA CCCCGAGGAG CTGGTGCTGC TCGGACACTC TCTGGGCATC    60

CCCTGGGCTC CCCTGAGCTC CTGCCCCAGC CAGGCCCTGC AGCTGGCAGG CTGCTTGAGC    120

CAACTCCATA GCGGCCTTTT CCTCTACCAG GGGCTCCTGC AGGCCCTGGA AGGGATATCC    180

CCCGAGTTGG GTCCCACCTT GGACACACTG CAGCTGGACG TCGCCGACTT TGCCACCACC    240

ATCTGGCAGC AGATGGAAGA ACTGGGAATG GCCCCTGCCC TGCAGCCCAC CCAGGGTGCC    300

ATGCCGGCCT TCGCCTCTGC TTTCCAGCGC CGGGCAGGAG GGGTCCTGGT TGCTAGCCAT    360

CTGCAGAGCT TCCTGGAGGT GTCGTACCGC GTTCTACGCC ACCTTGCGCA GCCCTCTGGC    420

GGCTCTGGCG GCTCTCAGAG CTTCCTGCTC AAGTCTTTAG AGCAAGTGAG GAAGATCCAG    480

GGCGATGGCG CAGCGCTCCA GGAGAAGCTG TGTGCCACCT AATAA                   525

(2) INFORMATION FOR SEQ ID NO:26:

(i) SEQUENCE CHARACTERISTICS:
        (A) LENGTH: 525 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:26:

ATGGCTCCCG AGTTGGGTCC CACCTTGGAC ACACTGCAGC TGGACGTCGC CGACTTTGCC    60

ACCACCATCT GGCAGCAGAT GGAAGAACTG GGAATGGCCC CTGCCCTGCA GCCCACCCAG    120

GGTGCCATGC CGGCCTTCGC CTCTGCTTTC AGCGCCGGG CAGGAGGGGT CCTGGTTGCT    180
```

-continued

| | |
|---|---|
| AGCCATCTGC AGAGCTTCCT GGAGGTGTCG TACCGCGTTC TACGCCACCT TGCGCAGCCC | 240 |
| TCTGGCGGCT CTGGCGGCTC TCAGAGCTTC CTGCTCAAGT CTTTAGAGCA AGTGAGGAAG | 300 |
| ATCCAGGGCG ATGGCGCAGC GCTCCAGGAG AAGCTGTGTG CCACCTACAA GCTGTGCCAC | 360 |
| CCCGAGGAGC TGGTGCTGCT CGGACACTCT CTGGGCATCC CCTGGGCTCC CCTGAGCTCC | 420 |
| TGCCCCAGCC AGGCCCTGCA GCTGGCAGGC TGCTTGAGCC AACTCCATAG CGGCCTTTTC | 480 |
| CTCTACCAGG GGCTCCTGCA GGCCCTGGAA GGGATATCCT AATAA | 525 |

(2) INFORMATION FOR SEQ ID NO:27:

(i) SEQUENCE CHARACTERISTICS:
        (A) LENGTH: 525 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:27:

| | |
|---|---|
| ATGGCTATGG CCCCTGCCCT GCAGCCCACC CAGGGTGCCA TGCCGGCCTT CGCCTCTGCT | 60 |
| TTCCAGCGCC GGGCAGGAGG GGTCCTGGTT GCTAGCCATC TGCAGAGCTT CCTGGAGGTG | 120 |
| TCGTACCGCG TTCTACGCCA CCTTGCGCAG CCCTCTGGCG GCTCTGGCGG CTCTCAGAGC | 180 |
| TTCCTGCTCA AGTCTTTAGA GCAAGTGAGG AAGATCCAGG GCGATGGCGC AGCGCTCCAG | 240 |
| GAGAAGCTGT GTGCCACCTA CAAGCTGTGC CACCCCGAGG AGCTGGTGCT GCTCGGACAC | 300 |
| TCTCTGGGCA TCCCCTGGGC TCCCCTGAGC TCCTGCCCCA GCCAGGCCCT GCAGCTGGCA | 360 |
| GGCTGCTTGA GCCAACTCCA TAGCGGCCTT TTCCTCTACC AGGGGCTCCT GCAGGCCCTG | 420 |
| GAAGGGATAT CCCCCGAGTT GGGTCCCACC TTGGACACAC TGCAGCTGGA CGTCGCCGAC | 480 |
| TTTGCCACCA CCATCTGGCA GCAGATGGAA GAACTGGGAT AATAA | 525 |

(2) INFORMATION FOR SEQ ID NO:28:

(i) SEQUENCE CHARACTERISTICS:
        (A) LENGTH: 525 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:28:

| | |
|---|---|
| ATGGCTACCC AGGGTGCCAT GCCGGCCTTC GCCTCTGCTT TCCAGCGCCG GGCAGGAGGG | 60 |
| GTCCTGGTTG CTAGCCATCT GCAGAGCTTC CTGGAGGTGT CGTACCGCGT TCTACGCCAC | 120 |
| CTTGCGCAGC CCTCTGGCGG CTCTGGCGG CTCTCAGAGCT TCCTGCTCAA GTCTTTAGAG | 180 |
| CAAGTGAGGA AGATCCAGGG CGATGGCGCA GCGCTCCAGG AGAAGCTGTG TGCCACCTAC | 240 |
| AAGCTGTGCC ACCCCGAGGA GCTGGTGCTG CTCGGACACT CTCTGGGCAT CCCCTGGGCT | 300 |
| CCCCTGAGCT CCTGCCCCAG CCAGGCCCTG CAGCTGGCAG GCTGCTTGAG CCAACTCCAT | 360 |
| AGCGGCCTTT TCCTCTACCA GGGGCTCCTG CAGGCCCTGG AAGGGATATC CCCCGAGTTG | 420 |
| GGTCCCACCT TGGACACACT GCAGCTGGAC GTCGCCGACT TTGCCACCAC CATCTGGCAG | 480 |
| CAGATGGAAG AACTGGGAAT GGCCCCTGCC CTGCAGCCCT AATAA | 525 |

(2) INFORMATION FOR SEQ ID NO:29:

(i) SEQUENCE CHARACTERISTICS:
    (A) LENGTH: 525 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA (synthetic)"

(xi) SEQUENCE DESCRIPTION: SEQ ID NO:29:

| | | | |
|---|---|---|---|
| ATGGCTTCTG CTTTCCAGCG CCGGGCAGGA GGGGTCCTGG TTGCTAGCCA TCTGCAGAGC | 60 |
| TTCCTGGAGG TGTCGTACCG CGTTCTACGC CACCTTGCGC AGCCCTCTGG CGGCTCTGGC | 120 |
| GGCTCTCAGA GCTTCCTGCT CAAGTCTTTA GAGCAAGTGA GGAAGATCCA GGGCGATGGC | 180 |
| GCAGCGCTCC AGGAGAAGCT GTGTGCCACC TACAAGCTGT GCCACCCCGA GGAGCTGGTG | 240 |
| CTGCTCGGAC ACTCTCTGGG CATCCCCTGG GCTCCCCTGA GCTCCTGCCC CAGCCAGGCC | 300 |
| CTGCAGCTGG CAGGCTGCTT GAGCCAACTC CATAGCGGCC TTTTCCTCTA CCAGGGGCTC | 360 |
| CTGCAGGCCC TGGAAGGGAT ATCCCCCGAG TTGGGTCCCA CCTTGGACAC ACTGCAGCTG | 420 |
| GACGTCGCCG ACTTTGCCAC CACCATCTGG CAGCAGATGG AAGAACTGGG AATGGCCCCT | 480 |
| GCCCTGCAGC CCACCCAGGG TGCCATGCCG GCCTTCGCCT AATAA | 525 |

(2) INFORMATION FOR SEQ ID NO:30:

(i) SEQUENCE CHARACTERISTICS:
    (A) LENGTH: 534 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA (synthetic)"

(xi) SEQUENCE DESCRIPTION: SEQ ID NO:30:

| | | | |
|---|---|---|---|
| ATGGCTTACA AGCTGTGCCA CCCCGAGGAG CTGGTGCTGC TCGGACACTC TCTGGGCATC | 60 |
| CCCTGGGCTC CCCTGAGCTC CTGCCCCAGC CAGGCCCTGC AGCTGGCAGG CTGCTTGAGC | 120 |
| CAACTCCATA GCGGCCTTTT CCTCTACCAG GGGCTCCTGC AGGCCCTGGA AGGGATATCC | 180 |
| CCCGAGTTGG GTCCCACCTT GGACACACTG CAGCTGGACG TCGCCGACTT TGCCACCACC | 240 |
| ATCTGGCAGC AGATGGAAGA ACTGGGAATG GCCCCTGCCC TGCAGCCCAC CCAGGGTGCC | 300 |
| ATGCCGGCCT TCGCCTCTGC TTTCCAGCGC CGGGCAGGAG GGGTCCTGGT TGCTAGCCAT | 360 |
| CTGCAGAGCT TCCTGGAGGT GTCGTACCGC GTTCTACGCC ACCTTGCGCA GCCCACACCA | 420 |
| TTGGGCCCTG CCAGCTCCCT GCCCCAGAGC TTCCTGCTCA GTCTTTAGA GCAAGTGAGA | 480 |
| AAGATCCAGG GCGATGGCGC AGCGCTCCAG GAGAAGCTGT GTGCCACCTA ATAA | 534 |

(2) INFORMATION FOR SEQ ID NO:31:

(i) SEQUENCE CHARACTERISTICS:
    (A) LENGTH: 534 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA (synthetic)"

(xi) SEQUENCE DESCRIPTION: SEQ ID NO:31:

| | | | |
|---|---|---|---|
| ATGGCTCCCG AGTTGGGTCC CACCTTGGAC ACACTGCAGC TGGACGTCGC CGACTTTGCC | 60 |
| ACCACCATCT GGCAGCAGAT GGAAGAACTG GGAATGGCCC CTGCCCTGCA GCCCACCCAG | 120 |

```
GGTGCCATGC CGGCCTTCGC CTCTGCTTTC CAGCGCCGGG CAGGAGGGGT CCTGGTTGCT      180

AGCCATCTGC AGAGCTTCCT GGAGGTGTCG TACCGCGTTC TACGCCACCT TGCGCAGCCC      240

ACACCATTGG GCCCTGCCAG CTCCCTGCCC CAGAGCTTCC TGCTCAAGTC TTTAGAGCAA      300

GTGAGAAAGA TCCAGGGCGA TGGCGCAGCG CTCCAGGAGA AGCTGTGTGC CACCTACAAG      360

CTGTGCCACC CCGAGGAGCT GGTGCTGCTC GGACACTCTC TGGGCATCCC CTGGGCTCCC      420

CTGAGCTCCT GCCCCAGCCA GGCCCTGCAG CTGGCAGGCT GCTTGAGCCA ACTCCATAGC      480

GGCCTTTTCC TCTACCAGGG GCTCCTGCAG GCCCTGGAAG GGATATCCTA ATAA           534
```

(2) INFORMATION FOR SEQ ID NO:32:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (Synthetic)"

(xi) SEQUENCE DESCRIPTION: SEQ ID NO:32:

```
ATGGCTATGG CCCCTGCCCT GCAGCCCACC CAGGGTGCCA TGCCGGCCTT CGCCTCTGCT       60

TTCCAGCGCC GGGCAGGAGG GGTCCTGGTT GCTAGCCATC TGCAGAGCTT CCTGGAGGTG      120

TCGTACCGCG TTCTACGCCA CCTTGCGCAG CCCACACCAT GGGCCCTGC CAGCTCCCTG       180

CCCCAGAGCT TCCTGCTCAA GTCTTTAGAG CAAGTGAGAA AGATCCAGGG CGATGGCGCA      240

GCGCTCCAGG AGAAGCTGTG TGCCACCTAC AAGCTGTGCC ACCCCGAGGA GCTGGTGCTG      300

CTCGGACACT CTCTGGGCAT CCCCTGGGCT CCCCTGAGCT CCTGCCCCAG CCAGGCCCTG      360

CAGCTGGCAG GCTGCTTGAG CCAACTCCAT AGCGGCCTTT TCCTCTACCA GGGGCTCCTG      420

CAGGCCCTGG AAGGGATATC CCCCGAGTTG GGTCCCACCT TGGACACACT GCAGCTGGAC      480

GTCGCCGACT TTGCCACCAC CATCTGGCAG CAGATGGAAG AACTGGGATA ATAA           534
```

(2) INFORMATION FOR SEQ ID NO:33:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:33:

```
ATGGCTACCC AGGGTGCCAT GCCGGCCTTC GCCTCTGCTT TCCAGCGCCG GGCAGGAGGG       60

GTCCTGGTTG CTAGCCATCT GCAGAGCTTC CTGGAGGTGT CGTACCGCGT TCTACGCCAC      120

CTTGCGCAGC CCACACCATT GGGCCCTGCC AGCTCCCTGC CCAGAGCTT CCTGCTCAAG       180

TCTTTAGAGC AAGTGAGAAA GATCCAGGGC GATGGCGCAG CGCTCCAGGA GAAGCTGTGT      240

GCCACCTACA AGCTGTGCCA CCCCGAGGAG CTGGTGCTGC TCGGACACTC TCTGGGCATC      300

CCCTGGGCTC CCCTGAGCTC CTGCCCCAGC CAGGCCCTGC AGCTGGCAGG CTGCTTGAGC      360

CAACTCCATA GCGGCCTTTT CCTCTACCAG GGGCTCCTGC AGGCCCTGGA AGGGATATCC      420

CCCGAGTTGG GTCCCACCTT GGACACACTG CAGCTGGACG TCGCCGACTT TGCCACCACC      480

ATCTGGCAGC AGATGGAAGA ACTGGGAATG GCCCCTGCCC TGCAGCCCTA ATAA           534
```

(2) INFORMATION FOR SEQ ID NO:34:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:34:

```
ATGGCTTCTG CTTTCCAGCG CCGGGCAGGA GGGGTCCTGG TTGCTAGCCA TCTGCAGAGC      60

TTCCTGGAGG TGTCGTACCG CGTTCTACGC CACCTTGCGC AGCCCACACC ATTGGGCCCT     120

GCCAGCTCCC TGCCCCAGAG CTTCCTGCTC AAGTCTTTAG AGCAAGTGAG AAAGATCCAG     180

GGCGATGGCG CAGCGCTCCA GGAGAAGCTG TGTGCCACCT ACAAGCTGTG CCACCCCGAG     240

GAGCTGGTGC TGCTCGGACA CTCTCTGGGC ATCCCCTGGG CTCCCCTGAG CTCCTGCCCC     300

AGCCAGGCCC TGCAGCTGGC AGGCTGCTTG AGCCAACTCC ATAGCGGCCT TTTCCTCTAC     360

CAGGGGCTCC TGCAGGCCCT GGAAGGGATA TCCCCCGAGT TGGGTCCCAC CTTGGACACA     420

CTGCAGCTGG ACGTCGCCGA CTTTGCCACC ACCATCTGGC AGCAGATGGA AGAACTGGGA     480

ATGGCCCCTG CCCTGCAGCC CACCCAGGGT GCCATGCCGG CCTTCGCCTA ATAA           534
```

(2) INFORMATION FOR SEQ ID NO:35:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:35:

```
ATGGCTCCGG AACTGGGTCC AACTCTGGAC ACACTGCAGC TGGACGTCGC CGACTTTGCC      60

ACCACCATCT GGCAGCAGAT GGAAGAACTG GAATGGCCC CTGCCCTGCA GCCCACCCAG      120

GGTGCCATGC CGGCCTTCGC CTCTGCTTTC CAGCGCCGGG CAGGAGGGGT CCTGGTTGCT     180

AGCCATCTGC AGAGCTTCCT GGAGGTGTCG TACCGCGTTC TACGCCACCT TGCGCAGCCC     240

ACACCATTGG GCCCTGCCAG CTCCCTGCCC CAGAGCTTCC TGCTCAAGTC TTTAGAGCAA     300

GTGAGAAAGA TCCAGGGCGA TGGCGCAGCG CTCCAGGAGA AGCTGTGTGC CACCTACAAG     360

CTGTGCCACC CCGAGGAGCT GGTGCTGCTC GGACACTCTC TGGGCATCCC CTGGGCTCCC     420

CTGAGCTCCT GCCCCAGCCA GGCCCTGCAG CTGGCAGGCT GCTTGAGCCA ACTCCATAGC     480

GGCCTTTTCC TCTACCAGGG GCTCCTGCAG GCCCTGGAAG GGATATCCTA A              531
```

(2) INFORMATION FOR SEQ ID NO:36:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:36:

```
ATGGCTATGG CTCCAGCTCT GCAACCAACT CAAGGTGCAA TGCCAGCATT TGCATCTGCT      60
```

| | |
|---|---|
| TTTCAACGTC GTGCAGGTGG TGTTCTGGTT GCTAGCCATC TGCAGAGCTT CCTGGAGGTG | 120 |
| TCGTACCGCG TTCTACGCCA CCTTGCGCAG CCCACACCAT GGGCCCTGC CAGCTCCCTG | 180 |
| CCCCAGAGCT TCCTGCTCAA GTCTTTAGAG CAAGTGAGAA AGATCCAGGG CGATGGCGCA | 240 |
| GCGCTCCAGG AGAAGCTGTG TGCCACCTAC AAGCTGTGCC ACCCCGAGGA GCTGGTGCTG | 300 |
| CTCGGACACT CTCTGGGCAT CCCCTGGGCT CCCCTGAGCT CCTGCCCCAG CCAGGCCCTG | 360 |
| CAGCTGGCAG GCTGCTTGAG CCAACTCCAT AGCGGCCTTT TCCTCTACCA GGGGCTCCTG | 420 |
| CAGGCCCTGG AAGGGATATC CCCCGAGTTG GGTCCCACCT TGGACACACT GCAGCTGGAC | 480 |
| GTCGCCGACT TTGCCACCAC CATCTGGCAG CAGATGGAAG AACTGGGATA A | 531 |

(2) INFORMATION FOR SEQ ID NO:37:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:37:

| | |
|---|---|
| ATGGCTACTC AAGGTGCTAT GCCAGCTTTT GCTTCTGCTT TTCAACGTCG TGCAGGTGGT | 60 |
| GTTCTGGTTG CTAGCCATCT GCAGAGCTTC CTGGAGGTGT CGTACCGCGT TCTACGCCAC | 120 |
| CTTGCGCAGC CCACACCATT GGGCCCTGCC AGCTCCCTGC CCCAGAGCTT CCTGCTCAAG | 180 |
| TCTTTAGAGC AAGTGAGAAA GATCCAGGGC GATGGCGCAG CGCTCCAGGA GAAGCTGTGT | 240 |
| GCCACCTACA AGCTGTGCCA CCCCGAGGAG CTGGTGCTGC TCGGACACTC TCTGGGCATC | 300 |
| CCCTGGGCTC CCCTGAGCTC CTGCCCCAGC CAGGCCCTGC AGCTGGCAGG CTGCTTGAGC | 360 |
| CAACTCCATA GCGGCCTTTT CCTCTACCAG GGGCTCCTGC AGGCCCTGGA AGGGATATCC | 420 |
| CCCGAGTTGG GTCCCACCTT GGACACACTG CAGCTGGACG TCGCCGACTT TGCCACCACC | 480 |
| ATCTGGCAGC AGATGGAAGA ACTGGGAATG GCCCCTGCCC TGCAGCCCTA A | 531 |

(2) INFORMATION FOR SEQ ID NO:38:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:38:

| | |
|---|---|
| ATGGCTTCTG CTTTTCAACG TCGTGCAGGT GGTGTTCTGG TTGCTAGCCA TCTGCAGAGC | 60 |
| TTCCTGGAGG TGTCGTACCG CGTTCTACGC CACCTTGCGC AGCCCACACC ATTGGGCCCT | 120 |
| GCCAGCTCCC TGCCCCAGAG CTTCCTGCTC AAGTCTTTAG AGCAAGTGAG AAAGATCCAG | 180 |
| GGCGATGGCG CAGCGCTCCA GGAGAAGCTG TGTGCCACCT ACAAGCTGTG CCACCCCGAG | 240 |
| GAGCTGGTGC TGCTCGGACA CTCTCTGGGC ATCCCCTGGG CTCCCCTGAG CTCCTGCCCC | 300 |
| AGCCAGGCCC TGCAGCTGGC AGGCTGCTTG AGCCAACTCC ATAGCGGCCT TTTCCTCTAC | 360 |
| CAGGGGCTCC TGCAGGCCCT GGAAGGGATA TCCCCCGAGT GGGTCCCAC CTTGGACACA | 420 |
| CTGCAGCTGG ACGTCGCCGA CTTTGCCACC ACCATCTGGC AGCAGATGGA AGAACTGGGA | 480 |
| ATGGCCCCTG CCCTGCAGCC CACCCAGGGT GCCATGCCGG CCTTCGCCTA A | 531 |

(2) INFORMATION FOR SEQ ID NO:39:

(i) SEQUENCE CHARACTERISTICS:
        (A) LENGTH: 522 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:39:

```
ATGGCTCCGG AACTGGGTCC AACTCTGGAC ACACTGCAGC TGGACGTCGC CGACTTTGCC    60

ACCACCATCT GGCAGCAGAT GGAAGAACTG GGAATGGCCC CTGCCCTGCA GCCCACCCAG   120

GGTGCCATGC CGGCCTTCGC CTCTGCTTTC CAGCGCCGGG CAGGAGGGGT CCTGGTTGCT   180

AGCCATCTGC AGAGCTTCCT GGAGGTGTCG TACCGCGTTC TACGCCACCT TGCGCAGCCC   240

TCTGGCGGCT CTGGCGGCTC TCAGAGCTTC CTGCTCAAGT CTTTAGAGCA AGTGAGAAAG   300

ATCCAGGGCG ATGGCGCAGC GCTCCAGGAG AAGCTGTGTG CCACCTACAA GCTGTGCCAC   360

CCCGAGGAGC TGGTGCTGCT CGGACACTCT CTGGGCATCC CCTGGGCTCC CCTGAGCTCC   420

TGCCCCAGCC AGGCCCTGCA GCTGGCAGGC TGCTTGAGCC AACTCCATAG CGGCCTTTTC   480

CTCTACCAGG GGCTCCTGCA GGCCCTGGAA GGGATATCCT AA                     522
```

(2) INFORMATION FOR SEQ ID NO:40:

(i) SEQUENCE CHARACTERISTICS:
        (A) LENGTH: 522 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:40:

```
ATGGCTATGG CTCCAGCTCT GCAACCAACT CAAGGTGCAA TGCCAGCATT TGCATCTGCT    60

TTTCAACGTC GTGCAGGTGG TGTTCTGGTT GCTAGCCATC TGCAGAGCTT CCTGGAGGTG   120

TCGTACCGCG TTCTACGCCA CCTTGCGCAG CCCTCTGGCG GCTCTGGCGG CTCTCAGAGC   180

TTCCTGCTCA AGTCTTTAGA GCAAGTGAGA AAGATCCAGG GCGATGGCGC AGCGCTCCAG   240

GAGAAGCTGT GTGCCACCTA CAAGCTGTGC CACCCCGAGG AGCTGGTGCT GCTCGGACAC   300

TCTCTGGGCA TCCCCTGGGC TCCCCTGAGC TCCTGCCCCA GCCAGGCCCT GCAGCTGGCA   360

GGCTGCTTGA GCCAACTCCA TAGCGGCCTT TTCCTCTACC AGGGGCTCCT GCAGGCCCTG   420

GAAGGGATAT CCCCCGAGTT GGGTCCCACC TTGGACACAC TGCAGCTGGA CGTCGCCGAC   480

TTTGCCACCA CCATCTGGCA GCAGATGGAA GAACTGGGAT AA                     522
```

(2) INFORMATION FOR SEQ ID NO:41:

(i) SEQUENCE CHARACTERISTICS:
        (A) LENGTH: 522 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:41:

```
ATGGCTACTC AAGGTGCTAT GCCAGCTTTT GCTTCTGCTT TTCAACGTCG TGCAGGTGGT        60

GTTCTGGTTG CTAGCCATCT GCAGAGCTTC CTGGAGGTGT CGTACCGCGT TCTACGCCAC       120

CTTGCGCAGC CCTCTGGCGG CTCTGGCGGC TCTCAGAGCT TCCTGCTCAA GTCTTTAGAG       180

CAAGTGAGAA AGATCCAGGG CGATGGCGCA GCGCTCCAGG AGAAGCTGTG TGCCACCTAC       240

AAGCTGTGCC ACCCCGAGGA GCTGGTGCTG CTCGGACACT CTCTGGGCAT CCCCTGGGCT       300

CCCCTGAGCT CCTGCCCCAG CCAGGCCCTG CAGCTGGCAG GCTGCTTGAG CCAACTCCAT       360

AGCGGCCTTT TCCTCTACCA GGGGCTCCTG CAGGCCCTGG AAGGGATATC CCCCGAGTTG       420

GGTCCCACCT TGGACACACT GCAGCTGGAC GTCGCCGACT TTGCCACCAC CATCTGGCAG       480

CAGATGGAAG AACTGGGAAT GGCCCCTGCC CTGCAGCCCT AA                         522

(2) INFORMATION FOR SEQ ID NO:42:

(i) SEQUENCE CHARACTERISTICS:
        (A) LENGTH: 522 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:42:

ATGGCTTCTG CTTTTCAACG TCGTGCAGGT GGTGTTCTGG TTGCTAGCCA TCTGCAGAGC        60

TTCCTGGAGG TGTCGTACCG CGTTCTACGC CACCTTGCGC AGCCCTCTGG CGGCTCTGGC       120

GGCTCTCAGA GCTTCCTGCT CAAGTCTTTA GAGCAAGTGA GAAAGATCCA GGGCGATGGC       180

GCAGCGCTCC AGGAGAAGCT GTGTGCCACC TACAAGCTGT GCCACCCCGA GGAGCTGGTG       240

CTGCTCGGAC ACTCTCTGGG CATCCCCTGG GCTCCCCTGA GCTCCTGCCC CAGCCAGGCC       300

CTGCAGCTGG CAGGCTGCTT GAGCCAACTC CATAGCGGCC TTTTCCTCTA CCAGGGGCTC       360

CTGCAGGCCC TGGAAGGGAT ATCCCCCGAG TTGGGTCCCA CCTTGGACAC ACTGCAGCTG       420

GACGTCGCCG ACTTTGCCAC CACCATCTGG CAGCAGATGG AAGAACTGGG AATGGCCCCT       480

GCCCTGCAGC CCACCCAGGG TGCCATGCCG GCCTTCGCCT AA                         522

(2) INFORMATION FOR SEQ ID NO:43:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

Tyr Lys Leu Cys His Pro Glu Glu Leu Val Leu Leu Gly His Ser Leu
1               5                   10                  15

Gly Ile Pro Trp Ala Pro Leu Ser Ser Cys Pro Ser Gln Ala Leu Gln
            20                  25                  30

Leu Ala Gly Cys Leu Ser Gln Leu His Ser Gly Leu Phe Leu Tyr Gln
        35                  40                  45

Gly Leu Leu Gln Ala Leu Glu Gly Ile Ser Pro Glu Leu Gly Pro Thr
    50                  55                  60

Leu Asp Thr Leu Gln Leu Asp Val Ala Asp Phe Ala Thr Thr Ile Trp
65                  70                  75                  80

Gln Gln Met Glu Glu Leu Gly Met Ala Pro Ala Leu Gln Pro Thr Gln
```

```
                    85                  90                  95
Gly Ala Met Pro Ala Phe Ala Ser Ala Phe Gln Arg Arg Ala Gly Gly
                100                 105                 110

Val Leu Val Ala Ser His Leu Gln Ser Phe Leu Glu Val Ser Tyr Arg
                115                 120                 125

Val Leu Arg His Leu Ala Gln Pro Ser Gly Ser Gly Gly Ser Gln
                130                 135                 140

Ser Phe Leu Leu Lys Ser Leu Glu Gln Val Arg Lys Ile Gln Gly Asp
145                 150                 155                 160

Gly Ala Ala Leu Gln Glu Lys Leu Cys Ala Thr
                165                 170
```

(2) INFORMATION FOR SEQ ID NO:44:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

```
Pro Glu Leu Gly Pro Thr Leu Asp Thr Leu Gln Leu Asp Val Ala Asp
1               5                   10                  15

Phe Ala Thr Thr Ile Trp Gln Gln Met Glu Glu Leu Gly Met Ala Pro
                20                  25                  30

Ala Leu Gln Pro Thr Gln Gly Ala Met Pro Ala Phe Ala Ser Ala Phe
                35                  40                  45

Gln Arg Arg Ala Gly Gly Val Leu Val Ala Ser His Leu Gln Ser Phe
            50                  55                  60

Leu Glu Val Ser Tyr Arg Val Leu Arg His Leu Ala Gln Pro Ser Gly
65                  70                  75                  80

Gly Ser Gly Gly Ser Gln Ser Phe Leu Leu Lys Ser Leu Glu Gln Val
                85                  90                  95

Arg Lys Ile Gln Gly Asp Gly Ala Ala Leu Gln Glu Lys Leu Cys Ala
                100                 105                 110

Thr Tyr Lys Leu Cys His Pro Glu Glu Leu Val Leu Leu Gly His Ser
                115                 120                 125

Leu Gly Ile Pro Trp Ala Pro Leu Ser Ser Cys Pro Ser Gln Ala Leu
                130                 135                 140

Gln Leu Ala Gly Cys Leu Ser Gln Leu His Ser Gly Leu Phe Leu Tyr
145                 150                 155                 160

Gln Gly Leu Leu Gln Ala Leu Glu Gly Ile Ser
                165                 170
```

(2) INFORMATION FOR SEQ ID NO:45:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

```
Thr Gln Gly Ala Met Pro Ala Phe Ala Ser Ala Phe Gln Arg Arg Ala
1               5                   10                  15
```

```
Gly Gly Val Leu Val Ala Ser His Leu Gln Ser Phe Leu Glu Val Ser
            20                  25                  30

Tyr Arg Val Leu Arg His Leu Ala Gln Pro Ser Gly Gly Ser Gly Gly
            35                  40                  45

Ser Gln Ser Phe Leu Leu Lys Ser Leu Glu Gln Val Arg Lys Ile Gln
 50                  55                  60

Gly Asp Gly Ala Ala Leu Gln Glu Lys Leu Cys Ala Thr Tyr Lys Leu
 65                  70                  75                  80

Cys His Pro Glu Glu Leu Val Leu Leu Gly His Ser Leu Gly Ile Pro
                 85                  90                  95

Trp Ala Pro Leu Ser Ser Cys Pro Ser Gln Ala Leu Gln Leu Ala Gly
            100                 105                 110

Cys Leu Ser Gln Leu His Ser Gly Leu Phe Leu Tyr Gln Gly Leu Leu
            115                 120                 125

Gln Ala Leu Glu Gly Ile Ser Pro Glu Leu Gly Pro Thr Leu Asp Thr
130                 135                 140

Leu Gln Leu Asp Val Ala Asp Phe Ala Thr Thr Ile Trp Gln Gln Met
145                 150                 155                 160

Glu Glu Leu Gly Met Ala Pro Ala Leu Gln Pro
                165                 170

(2) INFORMATION FOR SEQ ID NO:46:

(i) SEQUENCE CHARACTERISTICS:
        (A) LENGTH: 118 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:46:

TGGAATAAAA AAGAGAGAAG GAAAAGGATA GAAGAAGGGG GGGGAAGGGA GAAAAGGCAA        60

TTCGGAGGTA ACGAAGAAGC GGTGGGAAGG GGTATGAAAA AAATTTGGTG GGTAAAAG        118

(2) INFORMATION FOR SEQ ID NO:47:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

Ser Ala Phe Gln Arg Arg Ala Gly Gly Val Leu Val Ala Ser His Leu
 1               5                  10                  15

Gln Ser Phe Leu Glu Val Ser Tyr Arg Val Leu Arg His Leu Ala Gln
            20                  25                  30

Pro Ser Gly Gly Ser Gly Gly Ser Gln Ser Phe Leu Leu Lys Ser Leu
            35                  40                  45

Glu Gln Val Arg Lys Ile Gln Gly Asp Gly Ala Ala Leu Gln Glu Lys
 50                  55                  60

Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                 85                  90                  95

Gln Ala Leu Gln Leu Ala Gly Cys Leu Ser Gln Leu His Ser Gly Leu
```

-continued

```
                        100                 105                 110
Phe Leu Tyr Gln Gly Leu Leu Gln Ala Leu Glu Gly Ile Ser Pro Glu
                115                 120                 125

Leu Gly Pro Thr Leu Asp Thr Leu Gln Leu Asp Val Ala Asp Phe Ala
        130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala
                165                 170
```

(2) INFORMATION FOR SEQ ID NO:48:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

```
Tyr Lys Leu Cys His Pro Glu Glu Leu Val Leu Leu Gly His Ser Leu
1               5                   10                  15

Gly Ile Pro Trp Ala Pro Leu Ser Ser Cys Pro Ser Gln Ala Leu Gln
                20                  25                  30

Leu Ala Gly Cys Leu Ser Gln Leu His Ser Gly Leu Phe Leu Tyr Gln
            35                  40                  45

Gly Leu Leu Gln Ala Leu Glu Gly Ile Ser Pro Glu Leu Gly Pro Thr
        50                  55                  60

Leu Asp Thr Leu Gln Leu Asp Val Ala Asp Phe Ala Thr Thr Ile Trp
65                  70                  75                  80

Gln Gln Met Glu Glu Leu Gly Met Ala Pro Ala Leu Gln Pro Thr Gln
                85                  90                  95

Gly Ala Met Pro Ala Phe Ala Ser Ala Phe Gln Arg Arg Ala Gly Gly
            100                 105                 110

Val Leu Val Ala Ser His Leu Gln Ser Phe Leu Glu Val Ser Tyr Arg
        115                 120                 125

Val Leu Arg His Leu Ala Gln Pro Thr Pro Leu Gly Pro Ala Ser Ser
        130                 135                 140

Leu Pro Gln Ser Phe Leu Leu Lys Ser Leu Glu Gln Val Arg Lys Ile
145                 150                 155                 160

Gln Gly Asp Gly Ala Ala Leu Gln Glu Lys Leu Cys Ala Thr
                165                 170
```

(2) INFORMATION FOR SEQ ID NO:49:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

```
Pro Glu Leu Gly Pro Thr Leu Asp Thr Leu Gln Leu Asp Val Ala Asp
1               5                   10                  15

Phe Ala Thr Thr Ile Trp Gln Gln Met Glu Glu Leu Gly Met Ala Pro
                20                  25                  30
```

```
Ala Leu Gln Pro Thr Gln Gly Ala Met Pro Ala Phe Ala Ser Ala Phe
        35                  40                  45

Gln Arg Arg Ala Gly Gly Val Leu Val Ala Ser His Leu Gln Ser Phe
        50                  55                  60

Leu Glu Val Ser Tyr Arg Val Leu Arg His Leu Ala Gln Pro Thr Pro
65                  70                  75                  80

Leu Gly Pro Ala Ser Ser Leu Pro Gln Ser Phe Leu Leu Lys Ser Leu
                85                  90                  95

Glu Gln Val Arg Lys Ile Gln Gly Asp Gly Ala Ala Leu Gln Glu Lys
                100                 105                 110

Leu Cys Ala Thr Tyr Lys Leu Cys His Pro Glu Glu Leu Val Leu Leu
        115                 120                 125

Gly His Ser Leu Gly Ile Pro Trp Ala Pro Leu Ser Ser Cys Pro Ser
        130                 135                 140

Gln Ala Leu Gln Leu Ala Gly Cys Leu Ser Gln Leu His Ser Gly Leu
145                 150                 155                 160

Phe Leu Tyr Gln Gly Leu Leu Gln Ala Leu Glu Gly Ile Ser
                165                 170
```

(2) INFORMATION FOR SEQ ID NO:50:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

```
Met Ala Pro Ala Leu Gln Pro Thr Gln Gly Ala Met Pro Ala Phe Ala
1               5                   10                  15

Ser Ala Phe Gln Arg Arg Ala Gly Gly Val Leu Val Ala Ser His Leu
                20                  25                  30

Gln Ser Phe Leu Glu Val Ser Tyr Arg Val Leu Arg His Leu Ala Gln
        35                  40                  45

Pro Thr Pro Leu Gly Pro Ala Ser Ser Leu Pro Gln Ser Phe Leu Leu
        50                  55                  60

Lys Ser Leu Glu Gln Val Arg Lys Ile Gln Gly Asp Gly Ala Ala Leu
65                  70                  75                  80

Gln Glu Lys Leu Cys Ala Thr Tyr Lys Leu Cys His Pro Glu Glu Leu
                85                  90                  95

Val Leu Leu Gly His Ser Leu Gly Ile Pro Trp Ala Pro Leu Ser Ser
                100                 105                 110

Cys Pro Ser Gln Ala Leu Gln Leu Ala Gly Cys Leu Ser Gln Leu His
        115                 120                 125

Ser Gly Leu Phe Leu Tyr Gln Gly Leu Leu Gln Ala Leu Glu Gly Ile
        130                 135                 140

Ser Pro Glu Leu Gly Pro Thr Leu Asp Thr Leu Gln Leu Asp Val Ala
145                 150                 155                 160

Asp Phe Ala Thr Thr Ile Trp Gln Gln Met Glu Glu Leu Gly
                165                 170
```

(2) INFORMATION FOR SEQ ID NO:51:

(i) SEQUENCE CHARACTERISTICS:
        (A) LENGTH: 174 amino acids
        (B) TYPE: amino acid (C) STRANDEDNESS: single
          (D) TOPOLOGY: linear (ii) MOLECULE TYPE: protein (xi) SEQUENCE DESCRIPTION: SEQ ID NO:51:

Thr Gln Gly Ala Met Pro Ala Phe Ala Ser Ala Phe Gln Arg Arg Ala
1               5                   10                  15

Gly Gly Val Leu Val Ala Ser His Leu Gln Ser Phe Leu Glu Val Ser
            20                  25                  30

Tyr Arg Val Leu Arg His Leu Ala Gln Pro Thr Pro Leu Gly Pro Ala
        35                  40                  45

Ser Ser Leu Pro Gln Ser Phe Leu Leu Lys Ser Leu Glu Gln Val Arg
    50                  55                  60

Lys Ile Gln Gly Asp Gly Ala Ala Leu Gln Glu Lys Leu Cys Ala Thr
65                  70                  75                  80

Tyr Lys Leu Cys His Pro Glu Glu Leu Val Leu Leu Gly His Ser Leu
                85                  90                  95

Gly Ile Pro Trp Ala Pro Leu Ser Ser Cys Pro Ser Gln Ala Leu Gln
            100                 105                 110

Leu Ala Gly Cys Leu Ser Gln Leu His Ser Gly Leu Phe Leu Tyr Gln
        115                 120                 125

Gly Leu Leu Gln Ala Leu Glu Gly Ile Ser Pro Glu Leu Gly Pro Thr
    130                 135                 140

Leu Asp Thr Leu Gln Leu Asp Val Ala Asp Phe Ala Thr Thr Ile Trp
145                 150                 155                 160

Gln Gln Met Glu Glu Leu Gly Met Ala Pro Ala Leu Gln Pro
                165                 170

(2) INFORMATION FOR SEQ ID NO:52:

(i) SEQUENCE CHARACTERISTICS:
          (A) LENGTH: 174 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:52:

Ser Ala Phe Gln Arg Arg Ala Gly Gly Val Leu Val Ala Ser His Leu
1               5                   10                  15

Gln Ser Phe Leu Glu Val Ser Tyr Arg Val Leu Arg His Leu Ala Gln
            20                  25                  30

Pro Thr Pro Leu Gly Pro Ala Ser Ser Leu Pro Gln Ser Phe Leu Leu
        35                  40                  45

Lys Ser Leu Glu Gln Val Arg Lys Ile Gln Gly Asp Gly Ala Ala Leu
    50                  55                  60

Gln Glu Lys Leu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

```
Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala
                165                 170
```

(2) INFORMATION FOR SEQ ID NO:53:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

```
Pro Glu Leu Gly Pro Thr Leu Asp Thr Leu Gln Leu Asp Val Ala Asp
1                 5                  10                  15

Phe Ala Thr Thr Ile Trp Gln Gln Met Glu Glu Leu Gly Met Ala Pro
                20                  25                  30

Ala Leu Gln Pro Thr Gln Gly Ala Met Pro Ala Phe Ala Ser Ala Phe
                35                  40                  45

Gln Arg Arg Ala Gly Gly Val Leu Val Ala Ser His Leu Gln Ser Phe
50                  55                  60

Leu Glu Val Ser Tyr Arg Val Leu Arg His Leu Ala Gln Pro Thr Pro
65                  70                  75                  80

Leu Gly Pro Ala Ser Ser Leu Pro Gln Ser Phe Leu Leu Lys Ser Leu
                85                  90                  95

Glu Gln Val Arg Lys Ile Gln Gly Asp Gly Ala Ala Leu Gln Glu Lys
                100                 105                 110

Leu Cys Ala Thr Tyr Lys Leu Cys His Pro Glu Glu Leu Val Leu Leu
                115                 120                 125

Gly His Ser Leu Gly Ile Pro Trp Ala Pro Leu Ser Ser Cys Pro Ser
130                 135                 140

Gln Ala Leu Gln Leu Ala Gly Cys Leu Ser Gln Leu His Ser Gly Leu
145                 150                 155                 160

Phe Leu Tyr Gln Gly Leu Leu Gln Ala Leu Glu Gly Ile Ser
                165                 170
```

(2) INFORMATION FOR SEQ ID NO:54:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:54:

```
Met Ala Pro Ala Leu Gln Pro Thr Gln Gly Ala Met Pro Ala Phe Ala
1                 5                  10                  15

Ser Ala Phe Gln Arg Arg Ala Gly Gly Val Leu Val Ala Ser His Leu
                20                  25                  30

Gln Ser Phe Leu Glu Val Ser Tyr Arg Val Leu Arg His Leu Ala Gln
                35                  40                  45

Pro Thr Pro Leu Gly Pro Ala Ser Ser Leu Pro Gln Ser Phe Leu Leu
                50                  55                  60

Lys Ser Leu Glu Gln Val Arg Lys Ile Gln Gly Asp Gly Ala Ala Leu
```

```
65              70              75              80
Gln Glu Lys Leu Cys Ala Thr Tyr Lys Leu Cys His Pro Glu Glu Leu
                85              90              95
Val Leu Leu Gly His Ser Leu Gly Ile Pro Trp Ala Pro Leu Ser Ser
            100             105             110
Cys Pro Ser Gln Ala Leu Gln Leu Ala Gly Cys Leu Ser Gln Leu His
        115             120             125
Ser Gly Leu Phe Leu Tyr Gln Gly Leu Leu Gln Ala Leu Glu Gly Ile
    130             135             140
Ser Pro Glu Leu Gly Pro Thr Leu Asp Thr Leu Gln Leu Asp Val Ala
145             150             155             160
Asp Phe Ala Thr Thr Ile Trp Gln Gln Met Glu Glu Leu Gly
                165             170
```

(2) INFORMATION FOR SEQ ID NO:55:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

```
Thr Gln Gly Ala Met Pro Ala Phe Ala Ser Ala Phe Gln Arg Arg Ala
1               5               10              15
Gly Gly Val Leu Val Ala Ser His Leu Gln Ser Phe Leu Glu Val Ser
                20              25              30
Tyr Arg Val Leu Arg His Leu Ala Gln Pro Thr Pro Leu Gly Pro Ala
            35              40              45
Ser Ser Leu Pro Gln Ser Phe Leu Leu Lys Ser Leu Glu Gln Val Arg
        50              55              60
Lys Ile Gln Gly Asp Gly Ala Ala Leu Gln Glu Lys Leu Cys Ala Thr
65              70              75              80
Tyr Lys Leu Cys His Pro Glu Glu Leu Val Leu Leu Gly His Ser Leu
                85              90              95
Gly Ile Pro Trp Ala Pro Leu Ser Ser Cys Pro Ser Gln Ala Leu Gln
            100             105             110
Leu Ala Gly Cys Leu Ser Gln Leu His Ser Gly Leu Phe Leu Tyr Gln
        115             120             125
Gly Leu Leu Gln Ala Leu Glu Gly Ile Ser Pro Glu Leu Gly Pro Thr
    130             135             140
Leu Asp Thr Leu Gln Leu Asp Val Ala Asp Phe Ala Thr Thr Ile Trp
145             150             155             160
Gln Gln Met Glu Glu Leu Gly Met Ala Pro Ala Leu Gln Pro
                165             170
```

(2) INFORMATION FOR SEQ ID NO:56:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:56:

```
Ser Ala Phe Gln Arg Arg Ala Gly Gly Val Leu Val Ala Ser His Leu
1               5                   10                  15

Gln Ser Phe Leu Glu Val Ser Tyr Arg Val Leu Arg His Leu Ala Gln
            20                  25                  30

Pro Thr Pro Leu Gly Pro Ala Ser Ser Leu Pro Gln Ser Phe Leu Leu
            35                  40                  45

Lys Ser Leu Glu Gln Val Arg Lys Ile Gln Gly Asp Gly Ala Ala Leu
50                  55                  60

Gln Glu Lys Leu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
                100                 105                 110

Ser Gly Leu Phe Leu Tyr Gln Gly Leu Leu Gln Ala Leu Glu Gly Ile
                115                 120                 125

Ser Pro Glu Leu Gly Pro Thr Leu Asp Thr Leu Gln Leu Asp Val Ala
                130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala
                165                 170
```

(2) INFORMATION FOR SEQ ID NO:57:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:57:

```
Pro Glu Leu Gly Pro Thr Leu Asp Thr Leu Gln Leu Asp Val Ala Asp
1               5                   10                  15

Phe Ala Thr Thr Ile Trp Gln Gln Met Glu Glu Leu Gly Met Ala Pro
            20                  25                  30

Ala Leu Gln Pro Thr Gln Gly Ala Met Pro Ala Phe Ala Ser Ala Phe
            35                  40                  45

Gln Arg Arg Ala Gly Gly Val Leu Val Ala Ser His Leu Gln Ser Phe
50                  55                  60

Leu Glu Val Ser Tyr Arg Val Leu Arg His Leu Ala Gln Pro Ser Gly
65                  70                  75                  80

Gly Ser Gly Gly Ser Gln Ser Phe Leu Leu Lys Ser Leu Glu Gln Val
                85                  90                  95

Arg Lys Ile Gln Gly Asp Gly Ala Ala Leu Gln Glu Lys Leu Cys Ala
                100                 105                 110

Thr Tyr Lys Leu Cys His Pro Glu Glu Leu Val Leu Leu Gly His Ser
                115                 120                 125

Leu Gly Ile Pro Trp Ala Pro Leu Ser Ser Cys Pro Ser Gln Ala Leu
                130                 135                 140

Gln Leu Ala Gly Cys Leu Ser Gln Leu His Ser Gly Leu Phe Leu Tyr
145                 150                 155                 160

Gln Gly Leu Leu Gln Ala Leu Glu Gly Ile Ser
                165                 170
```

(2) INFORMATION FOR SEQ ID NO:58:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:58:

```
Met Ala Pro Ala Leu Gln Pro Thr Gln Gly Ala Met Pro Ala Phe Ala
1               5                   10                  15

Ser Ala Phe Gln Arg Arg Ala Gly Gly Val Leu Val Ala Ser His Leu
            20                  25                  30

Gln Ser Phe Leu Glu Val Ser Tyr Arg Val Leu Arg His Leu Ala Gln
            35                  40                  45

Pro Ser Gly Gly Ser Gly Gly Ser Gln Ser Phe Leu Leu Lys Ser Leu
        50                  55                  60

Glu Gln Val Arg Lys Ile Gln Gly Asp Gly Ala Ala Leu Gln Glu Lys
65                  70                  75                  80

Ala Thr Tyr Lys Leu Cys His Pro Glu Glu Leu Val Leu Leu Gly His
                85                  90                  95

Ser Leu Gly Ile Pro Trp Ala Pro Leu Ser Ser Cys Pro Ser Gln Ala
            100                 105                 110

Leu Gln Leu Ala Gly Cys Leu Ser Gln Leu His Ser Gly Leu Phe Leu
            115                 120                 125

Tyr Gln Gly Leu Leu Gln Ala Leu Glu Gly Ile Ser Pro Glu Leu Gly
        130                 135                 140

Pro Thr Leu Asp Thr Leu Gln Leu Asp Val Ala Asp Phe Ala Thr Thr
145                 150                 155                 160

Ile Trp Gln Gln Met Glu Glu Leu Gly
                165
```

(2) INFORMATION FOR SEQ ID NO:59:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

```
Thr Gln Gly Ala Met Pro Ala Phe Ala Ser Ala Phe Gln Arg Arg Ala
1               5                   10                  15

Gly Gly Val Leu Val Ala Ser His Leu Gln Ser Phe Leu Glu Val Ser
            20                  25                  30

Tyr Arg Val Leu Arg His Leu Ala Gln Pro Ser Gly Gly Ser Gly Gly
            35                  40                  45

Ser Gln Ser Phe Leu Leu Lys Ser Leu Glu Gln Val Arg Lys Ile Gln
        50                  55                  60

Gly Asp Gly Ala Ala Leu Gln Glu Lys Leu Cys Ala Thr Tyr Lys Leu
65                  70                  75                  80

Cys His Pro Glu Glu Leu Val Leu Leu Gly His Ser Leu Gly Ile Pro
                85                  90                  95

Trp Ala Pro Leu Ser Ser Cys Pro Ser Gln Ala Leu Gln Leu Ala Gly
            100                 105                 110
```

Cys Leu Ser Gln Leu His Ser Gly Leu Phe Leu Tyr Gln Gly Leu Leu
            115                 120                 125

Gln Ala Leu Glu Gly Ile Ser Pro Glu Leu Gly Pro Thr Leu Asp Thr
            130                 135                 140

Leu Gln Leu Asp Val Ala Asp Phe Ala Thr Thr Ile Trp Gln Gln Met
145                 150                 155                 160

Glu Glu Leu Gly Met Ala Pro Ala Leu Gln Pro
                165                 170

(2) INFORMATION FOR SEQ ID NO:60:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:60:

Ser Ala Phe Gln Arg Arg Ala Gly Gly Val Leu Val Ala Ser His Leu
1               5                   10                  15

Gln Ser Phe Leu Glu Val Ser Tyr Arg Val Leu Arg His Leu Ala Gln
            20                  25                  30

Pro Ser Gly Gly Ser Gly Gly Ser Gln Ser Phe Leu Leu Lys Ser Leu
            35                  40                  45

Glu Gln Val Arg Lys Ile Gln Gly Asp Gly Ala Ala Leu Gln Glu Lys
            50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
            115                 120                 125

Leu Gly Pro Thr Leu Asp Thr Leu Gln Leu Asp Val Ala Asp Phe Ala
            130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala
                165                 170

(2) INFORMATION FOR SEQ ID NO:61:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

Gly Gly Gly Ser Gly Gly Gly Ser
1               5

(2) INFORMATION FOR SEQ ID NO:62:

(i) SEQUENCE CHARACTERISTICS:

(A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

Gly Gly Gly Ser Gly Gly Gly Ser Gly Gly Gly Ser
1               5                   10

(2) INFORMATION FOR SEQ ID NO:63:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

Ser Gly Gly Ser Gly Gly Ser
1               5

(2) INFORMATION FOR SEQ ID NO:64:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

Glu Phe Gly Asn Met
1               5

(2) INFORMATION FOR SEQ ID NO:65:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

Glu Phe Gly Gly Asn Met
1               5

(2) INFORMATION FOR SEQ ID NO:66:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

Glu Phe Gly Gly Asn Gly Gly Asn Met
1               5

(2) INFORMATION FOR SEQ ID NO:67:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

Gly Gly Ser Asp Met Ala Gly
1               5

(2) INFORMATION FOR SEQ ID NO:68:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:68:

GATCGACCAT GGCTCTGCTC GGACACTCTC TG                                32

(2) INFORMATION FOR SEQ ID NO:69:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:69:

CGATCGAAGC TTATTACACC AGCTCCTCGG GGTGGC                            36

(2) INFORMATION FOR SEQ ID NO:70:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:70:

GATCGACCAT GGCTCAACTC CATAGCGGCC TT                                32

(2) INFORMATION FOR SEQ ID NO:71:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:71:

CGATCGAAGC TTATTAGCTC AAGCAGCCTG CCAGCT                            36

(2) INFORMATION FOR SEQ ID NO:72:

```
    (i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:72:

GATCGACCAT GGCTCTTTTC CTCTACCAGG GG                                 32

(2) INFORMATION FOR SEQ ID NO:73:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:73:

CGATCGAAGC TTATTAGCCG CTATGGAGTT GGCTCA                             36

(2) INFORMATION FOR SEQ ID NO:74:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:74:

GATCGACCAT GGCTCTCTAC CAGGGGCTCC TG                                 32

(2) INFORMATION FOR SEQ ID NO:75:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:75:

CGATCGAAGC TTATTAGAAA AGGCCGCTAT GGAGTT                             36

(2) INFORMATION FOR SEQ ID NO:76:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:76:

GATCGACCAT GGCTGCCCTG GAAGGGATAT CC                                 32
```

(2) INFORMATION FOR SEQ ID NO:77:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:77:

CGATCGAAGC TTATTACTGC AGGAGCCCCT GGTAGA                                  36

(2) INFORMATION FOR SEQ ID NO:78:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:78:

GATCGACCAT GGCTGACTTT GCCACCACCA TC                                      32

(2) INFORMATION FOR SEQ ID NO:79:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:79:

CGATCGAAGC TTATTAGGCG ACGTCCAGCT GCAGTG                                  36

(2) INFORMATION FOR SEQ ID NO:80:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:80:

GATCGACCAT GGCTATCTGG CAGCAGATGG AA                                      32

(2) INFORMATION FOR SEQ ID NO:81:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:81:

CGATCGAAGC TTATTAGGTG GTGGCAAAGT CGGCGA                                  36

(2) INFORMATION FOR SEQ ID NO:82:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:82:

GATCGACCAT GGCTCAGCAG ATGGAAGAAC TG                          32

(2) INFORMATION FOR SEQ ID NO:83:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:83:

CGATCGAAGC TTATTACCAG ATGGTGGTGG CAAAGT                    36

(2) INFORMATION FOR SEQ ID NO:84:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:84:

CATGGCTTTG TTAGGACATT CTTTAGGTAT TCCATGGGCT CCTCTGAGCT        50

(2) INFORMATION FOR SEQ ID NO:85:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:85:

CAGAGGAGCC CATGGAATAC CTAAAGAATG TCCTAACAAA                40

(2) INFORMATION FOR SEQ ID NO:86:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:86:

ATGGCTCTGC TCGGACACTC TCTGGGCATC CCCTGGGCTC CCCTGAGCTC CTGCCCCAGC    60

```
CAGGCCCTGC AGCTGGCAGG CTGCTTGAGC CAACTCCATA GCGGCCTTTT CCTCTACCAG      120

GGGCTCCTGC AGGCCCTGGA AGGGATATCC CCCGAGTTGG GTCCCACCTT GGACACACTG      180

CAGCTGGACG TCGCCGACTT TGCCACCACC ATCTGGCAGC AGATGGAAGA ACTGGGAATG      240

GCCCCTGCCC TGCAGCCCAC CCAGGGTGCC ATGCCGGCCT TCGCCTCTGC TTTCCAGCGC      300

CGGGCAGGAG GGGTCCTGGT TGCTAGCCAT CTGCAGAGCT TCCTGGAGGT GTCGTACCGC      360

GTTCTACGCC ACCTTGCGCA GCCCACACCA TTGGGCCCTG CCAGCTCCCT GCCCCAGAGC      420

TTCCTGCTCA AGTCTTTAGA GCAAGTGAGA AAGATCCAGG GCGATGGCGC AGCGCTCCAG      480

GAGAAGCTGT GTGCCACCTA CAAGCTGTGC CACCCCGAGG AGCTGGTGTA ATAA           534
```

(2) INFORMATION FOR SEQ ID NO:87:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:87:

```
ATGGCTCAAC TCCATAGCGG CCTTTTCCTC TACCAGGGGC TCCTGCAGGC CCTGGAAGGG       60

ATATCCCCCG AGTTGGGTCC CACCTTGGAC ACACTGCAGC TGGACGTCGC CGACTTTGCC      120

ACCACCATCT GGCAGCAGAT GGAAGAACTG GGAATGGCCC TGCCCTGCA GCCCACCCAG       180

GGTGCCATGC CGGCCTTCGC CTCTGCTTTC AGCGCCGGG CAGGAGGGGT CCTGGTTGCT       240

AGCCATCTGC AGAGCTTCCT GGAGGTGTCG TACCGCGTTC TACGCCACCT TGCGCAGCCC      300

ACACCATTGG GCCCTGCCAG CTCCCTGCCC CAGAGCTTCC TGCTCAAGTC TTTAGAGCAA      360

GTGAGAAAGA TCCAGGGCGA TGGCGCAGCG CTCCAGGAGA AGCTGTGTGC CACCTACAAG      420

CTGTGCCACC CCGAGGAGCT GGTGCTGCTC GGACACTCTC TGGGCATCCC CTGGGCTCCC      480

CTGAGCTCCT GCCCCAGCCA GGCCCTGCAG CTGGCAGGCT GCTTGAGCTA ATAA           534
```

(2) INFORMATION FOR SEQ ID NO:88:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:88:

```
ATGGCTCTTT TCCTCTACCA GGGGCTCCTG CAGGCCCTGG AAGGGATATC CCCCGAGTTG       60

GTCCCACCT TGGACACACT GCAGCTGGAC GTCGCCGACT TGCCACCAC CATCTGGCAG        120

CAGATGGAAG AACTGGGAAT GGCCCCTGCC CTGCAGCCCA CCCAGGGTGC CATGCCGGCC      180

TTCGCCTCTG CTTTCAGCG CCGGGCAGGA GGGGTCCTGG TTGCTAGCCA TCTGCAGAGC       240

TTCCTGGAGG TGTCGTACCG CGTTCTACGC CACCTTGCGC AGCCCACACC ATTGGGCCCT      300

GCCAGCTCCC TGCCCCAGAG CTTCCTGCTC AAGTCTTTAG AGCAAGTGAG AAAGATCCAG      360

GGCGATGGCG CAGCGCTCCA GGAGAAGCTG TGTGCCACCT ACAAGCTGTG CCACCCCGAG      420

GAGCTGGTGC TGCTCGGACA CTCTCTGGGC ATCCCCTGGG CTCCCCTGAG CTCCTGCCCC      480
```

AGCCAGGCCC TGCAGCTGGC AGGCTGCTTG AGCCAACTCC ATAGCGGCTA ATAA        534

(2) INFORMATION FOR SEQ ID NO:89:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:89:

ATGGCTCTCT ACCAGGGGCT CCTGCAGGCC CTGGAAGGGA TATCCCCCGA GTTGGGTCCC        60

ACCTTGGACA CACTGCAGCT GGACGTCGCC GACTTTGCCA CCACCATCTG GCAGCAGATG        120

GAAGAACTGG GAATGGCCCC TGCCCTGCAG CCCACCCAGG GTGCCATGCC GGCCTTCGCC        180

TCTGCTTTCC AGCGCCGGGC AGGAGGGGTC CTGGTTGCTA GCCATCTGCA GAGCTTCCTG        240

GAGGTGTCGT ACCGCGTTCT ACGCCACCTT GCGCAGCCCA CACCATTGGG CCCTGCCAGC        300

TCCCTGCCCC AGAGCTTCCT GCTCAAGTCT TTAGAGCAAG TGAGAAAGAT CCAGGGCGAT        360

GGCGCAGCGC TCCAGGAGAA GCTGTGTGCC ACCTACAAGC TGTGCCACCC CGAGGAGCTG        420

GTGCTGCTCG GACACTCTCT GGGCATCCCC TGGGCTCCCC TGAGCTCCTG CCCCAGCCAG        480

GCCCTGCAGC TGGCAGGCTG CTTGAGCCAA CTCCATAGCG GCCTTTTCTA ATAA        534

(2) INFORMATION FOR SEQ ID NO:90:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:90:

ATGGCTGCCC TGGAAGGGAT ATCCCCCGAG TTGGGTCCCA CCTTGGACAC ACTGCAGCTG        60

GACGTCGCCG ACTTTGCCAC CACCATCTGG CAGCAGATGG AAGAACTGGG AATGGCCCCT        120

GCCCTGCAGC CCACCCAGGG TGCCATGCCG GCCTTCGCCT CTGCTTTCCA GCGCCGGGCA        180

GGAGGGGTCC TGGTTGCTAG CCATCTGCAG AGCTTCCTGG AGGTGTCGTA CCGCGTTCTA        240

CGCCACCTTG CGCAGCCCAC ACCATTGGGC CCTGCCAGCT CCCTGCCCCA GAGCTTCCTG        300

CTCAAGTCTT TAGAGCAAGT GAGAAAGATC CAGGGCGATG GCGCAGCGCT CCAGGAGAAG        360

CTGTGTGCCA CCTACAAGCT GTGCCACCCC GAGGAGCTGG TGCTGCTCGG ACACTCTCTG        420

GGCATCCCCT GGGCTCCCCT GAGCTCCTGC CCCAGCCAGG CCCTGCAGCT GGCAGGCTGC        480

TTGAGCCAAC TCCATAGCGG CCTTTTCCTC TACCAGGGGC TCCTGCAGTA ATAA        534

(2) INFORMATION FOR SEQ ID NO:91:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:91:

```
ATGGCTGACT TTGCCACCAC CATCTGGCAG CAGATGGAAG AACTGGGAAT GGCCCCTGCC      60

CTGCAGCCCA CCCAGGGTGC CATGCCGGCC TTCGCCTCTG CTTTCCAGCG CCGGGCAGGA     120

GGGGTCCTGG TTGCTAGCCA TCTGCAGAGC TTCCTGGAGG TGTCGTACCG CGTTCTACGC     180

CACCTTGCGC AGCCCACACC ATTGGGCCCT GCCAGCTCCC TGCCCCAGAG CTTCCTGCTC     240

AAGTCTTTAG AGCAAGTGAG AAAGATCCAG GGCGATGGCG CAGCGCTCCA GGAGAAGCTG     300

TGTGCCACCT ACAAGCTGTG CCACCCCGAG GAGCTGGTGC TGCTCGGACA CTCTCTGGGC     360

ATCCCCTGGG CTCCCCTGAG CTCCTGCCCC AGCCAGGCCC TGCAGCTGGC AGGCTGCTTG     420

AGCCAACTCC ATAGCGGCCT TTTCCTCTAC CAGGGGCTCC TGCAGGCCCT GGAAGGGATA     480

TCCCCCGAGT TGGGTCCCAC CTTGGACACA CTGCAGCTGG ACGTCGCCTA ATAA           534
```

(2) INFORMATION FOR SEQ ID NO:92:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:92:

```
ATGGCTATCT GGCAGCAGAT GGAAGAACTG GGAATGGCCC CTGCCCTGCA GCCCACCCAG      60

GGTGCCATGC CGGCCTTCGC CTCTGCTTTC CAGCGCCGGG CAGGAGGGGT CCTGGTTGCT     120

AGCCATCTGC AGAGCTTCCT GGAGGTGTCG TACCGCGTTC TACGCCACCT TGCGCAGCCC     180

ACACCATTGG GCCCTGCCAG CTCCCTGCCC CAGAGCTTCC TGCTCAAGTC TTTAGAGCAA     240

GTGAGAAAGA TCCAGGGCGA TGGCGCAGCG CTCCAGGAGA AGCTGTGTGC CACCTACAAG     300

CTGTGCCACC CCGAGGAGCT GGTGCTGCTC GGACACTCTC TGGGCATCCC CTGGGCTCCC     360

CTGAGCTCCT GCCCCAGCCA GGCCCTGCAG CTGGCAGGCT GCTTGAGCCA ACTCCATAGC     420

GGCCTTTTCC TCTACCAGGG GCTCCTGCAG GCCCTGGAAG GGATATCCCC CGAGTTGGGT     480

CCCACCTTGG ACACACTGCA GCTGGACGTC GCCGACTTTG CCACCACCTA ATAA           534
```

(2) INFORMATION FOR SEQ ID NO:93:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:93:

```
ATGGCTCAGC AGATGGAAGA ACTGGGAATG GCCCCTGCCC TGCAGCCCAC CCAGGGTGCC      60

ATGCCGGCCT TCGCCTCTGC TTTCCAGCGC CGGGCAGGAG GGGTCCTGGT TGCTAGCCAT     120

CTGCAGAGCT TCCTGGAGGT GTCGTACCGC GTTCTACGCC ACCTTGCGCA GCCCACACCA     180

TTGGGCCCTG CCAGCTCCCT GCCCCAGAGC TTCCTGCTCA AGTCTTTAGA GCAAGTGAGA     240

AAGATCCAGG GCGATGGCGC AGCGCTCCAG GAGAAGCTGT GTGCCACCTA CAAGCTGTGC     300

CACCCCGAGG AGCTGGTGCT GCTCGGACAC TCTCTGGGCA TCCCCTGGGC TCCCCTGAGC     360

TCCTGCCCCA GCCAGGCCCT GCAGCTGGCA GGCTGCTTGA GCCAACTCCA TAGCGGCCTT     420
```

```
TTCCTCTACC AGGGGCTCCT GCAGGCCCTG GAAGGGATAT CCCCCGAGTT GGGTCCCACC    480

TTGGACACAC TGCAGCTGGA CGTCGCCGAC TTTGCCACCA CCATCTGGTA ATAA          534
```

(2) INFORMATION FOR SEQ ID NO:94:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (synthetic)"

(xi) SEQUENCE DESCRIPTION: SEQ ID NO:94:

```
ATGGCTTTGT TAGGACATTC TTTAGGTATT CCATGGGCTC CTCTGAGCTC CTGCCCCAGC    60

CAGGCCCTGC AGCTGGCAGG CTGCTTGAGC CAACTCCATA GCGGCCTTTT CCTCTACCAG   120

GGGCTCCTGC AGGCCCTGGA AGGGATATCC CCCGAGTTGG GTCCCACCTT GGACACACTG   180

CAGCTGGACG TCGCCGACTT TGCCACCACC ATCTGGCAGC AGATGGAAGA ACTGGGAATG   240

GCCCCTGCCC TGCAGCCCAC CCAGGGTGCC ATGCCGGCCT TCGCCTCTGC TTTCCAGCGC   300

CGGGCAGGAG GGGTCCTGGT TGCTAGCCAT CTGCAGAGCT TCCTGGAGGT GTCGTACCGC   360

GTTCTACGCC ACCTTGCGCA GCCCACACCA TTGGGCCCTG CCAGCTCCCT GCCCCAGAGC   420

TTCCTGCTCA GTCTTTAGA GCAAGTGAGA AAGATCCAGG GCGATGGCGC AGCGCTCCAG    480

GAGAAGCTGT GTGCCACCTA CAAGCTGTGC CACCCCGAGG AGCTGGTGTA ATAA          534
```

(2) INFORMATION FOR SEQ ID NO:95:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:95:

```
Leu Leu Gly His Ser Leu Gly Ile Pro Trp Ala Pro Leu Ser Ser Cys
1               5                   10                  15

Pro Ser Gln Ala Leu Gln Leu Ala Gly Cys Leu Ser Gln Leu His Ser
            20                  25                  30

Gly Leu Phe Leu Tyr Gln Gly Leu Leu Gln Ala Leu Glu Gly Ile Ser
        35                  40                  45

Pro Glu Leu Gly Pro Thr Leu Asp Thr Leu Gln Leu Asp Val Ala Asp
    50                  55                  60

Phe Ala Thr Thr Ile Trp Gln Gln Met Glu Glu Leu Gly Met Ala Pro
65                  70                  75                  80

Ala Leu Gln Pro Thr Gln Gly Ala Met Pro Ala Phe Ala Ser Ala Phe
                85                  90                  95

Gln Arg Arg Ala Gly Gly Val Leu Val Ala Ser His Leu Gln Ser Phe
            100                 105                 110

Leu Glu Val Ser Tyr Arg Val Leu Arg His Leu Ala Gln Pro Thr Pro
        115                 120                 125

Leu Gly Pro Ala Ser Ser Leu Pro Gln Ser Phe Leu Leu Lys Ser Leu
    130                 135                 140

Glu Gln Val Arg Lys Ile Gln Gly Asp Gly Ala Ala Leu Gln Glu Lys
145                 150                 155                 160
```

Leu Cys Ala Thr Tyr Lys Leu Cys His Pro Glu Glu Leu Val
                165                 170

(2) INFORMATION FOR SEQ ID NO:96:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:96:

Gln Leu His Ser Gly Leu Phe Leu Tyr Gln Gly Leu Leu Gln Ala Leu
1               5                   10                  15

Glu Gly Ile Ser Pro Glu Leu Gly Pro Thr Leu Asp Thr Leu Gln Leu
                20                  25                  30

Asp Val Ala Asp Phe Ala Thr Thr Ile Trp Gln Gln Met Glu Glu Leu
            35                  40                  45

Gly Met Ala Pro Ala Leu Gln Pro Thr Gln Gly Ala Met Pro Ala Phe
        50                  55                  60

Ala Ser Ala Phe Gln Arg Arg Ala Gly Gly Val Leu Val Ala Ser His
65                  70                  75                  80

Leu Gln Ser Phe Leu Glu Val Ser Tyr Arg Val Leu Arg His Leu Ala
                85                  90                  95

Gln Pro Thr Pro Leu Gly Pro Ala Ser Ser Leu Pro Gln Ser Phe Leu
                100                 105                 110

Leu Lys Ser Leu Glu Gln Val Arg Lys Ile Gln Gly Asp Gly Ala Ala
            115                 120                 125

Leu Gln Glu Lys Leu Cys Ala Thr Tyr Lys Leu Cys His Pro Glu Glu
        130                 135                 140

Leu Val Leu Leu Gly His Ser Leu Gly Ile Pro Trp Ala Pro Leu Ser
145                 150                 155                 160

Ser Cys Pro Ser Gln Ala Leu Gln Leu Ala Gly Cys Leu Ser
                165                 170

(2) INFORMATION FOR SEQ ID NO:97:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:97:

Leu Phe Leu Tyr Gln Gly Leu Leu Gln Ala Leu Glu Gly Ile Ser Pro
1               5                   10                  15

Glu Leu Gly Pro Thr Leu Asp Thr Leu Gln Leu Asp Val Ala Asp Phe
                20                  25                  30

Ala Thr Thr Ile Trp Gln Gln Met Glu Glu Leu Gly Met Ala Pro Ala
            35                  40                  45

Leu Gln Pro Thr Gln Gly Ala Met Pro Ala Phe Ala Ser Ala Phe Gln
        50                  55                  60

Arg Arg Ala Gly Gly Val Leu Val Ala Ser His Leu Gln Ser Phe Leu
65                  70                  75                  80

Glu Val Ser Tyr Arg Val Leu Arg His Leu Ala Gln Pro Thr Pro Leu
                85                  90                  95

```
Gly Pro Ala Ser Ser Leu Pro Gln Ser Phe Leu Leu Lys Ser Leu Glu
            100                 105                 110

Gln Val Arg Lys Ile Gln Gly Asp Gly Ala Ala Leu Gln Glu Lys Leu
            115                 120                 125

Cys Ala Thr Tyr Lys Leu Cys His Pro Glu Glu Leu Val Leu Leu Gly
            130                 135                 140

His Ser Leu Gly Ile Pro Trp Ala Pro Leu Ser Ser Cys Pro Ser Gln
145                 150                 155                 160

Ala Leu Gln Leu Ala Gly Cys Leu Ser Gln Leu His Ser Gly
            165                 170
```

(2) INFORMATION FOR SEQ ID NO:98:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:98:

```
Leu Tyr Gln Gly Leu Leu Gln Ala Leu Glu Gly Ile Ser Pro Glu Leu
1                   5                   10                  15

Gly Pro Thr Leu Asp Thr Leu Gln Leu Asp Val Ala Asp Phe Ala Thr
            20                  25                  30

Thr Ile Trp Gln Gln Met Glu Glu Leu Gly Met Ala Pro Ala Leu Gln
            35                  40                  45

Pro Thr Gln Gly Ala Met Pro Ala Phe Ala Ser Ala Phe Gln Arg Arg
            50                  55                  60

Ala Gly Gly Val Leu Val Ala Ser His Leu Gln Ser Phe Leu Glu Val
65                  70                  75                  80

Ser Tyr Arg Val Leu Arg His Leu Ala Gln Pro Thr Pro Leu Gly Pro
            85                  90                  95

Ala Ser Ser Leu Pro Gln Ser Phe Leu Leu Lys Ser Leu Glu Gln Val
            100                 105                 110

Arg Lys Ile Gln Gly Asp Gly Ala Ala Leu Gln Glu Lys Leu Cys Ala
            115                 120                 125

Thr Tyr Lys Leu Cys His Pro Glu Glu Leu Val Leu Leu Gly His Ser
            130                 135                 140

Leu Gly Ile Pro Trp Ala Pro Leu Ser Ser Cys Pro Ser Gln Ala Leu
145                 150                 155                 160

Gln Leu Ala Gly Cys Leu Ser Gln Leu His Ser Gly Leu Phe
            165                 170
```

(2) INFORMATION FOR SEQ ID NO:99:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:99:

```
Ala Leu Glu Gly Ile Ser Pro Glu Leu Gly Pro Thr Leu Asp Thr Leu
1                   5                   10                  15

Gln Leu Asp Val Ala Asp Phe Ala Thr Thr Ile Trp Gln Gln Met Glu
```

```
                  20                  25                  30
Glu Leu Gly Met Ala Pro Ala Leu Gln Pro Thr Gln Gly Ala Met Pro
             35                  40                  45
Ala Phe Ala Ser Ala Phe Gln Arg Arg Ala Gly Gly Val Leu Val Ala
 50                  55                  60
Ser His Leu Gln Ser Phe Leu Glu Val Ser Tyr Arg Val Leu Arg His
 65                  70                  75                  80
Leu Ala Gln Pro Thr Pro Leu Gly Pro Ala Ser Ser Leu Pro Gln Ser
                 85                  90                  95
Phe Leu Leu Lys Ser Leu Glu Gln Val Arg Lys Ile Gln Gly Asp Gly
                100                 105                 110
Ala Ala Leu Gln Glu Lys Leu Cys Ala Thr Tyr Lys Leu Cys His Pro
            115                 120                 125
Glu Glu Leu Val Leu Leu Gly His Ser Leu Gly Ile Pro Trp Ala Pro
130                 135                 140
Leu Ser Ser Cys Pro Ser Gln Ala Leu Gln Leu Ala Gly Cys Leu Ser
145                 150                 155                 160
Gln Leu His Ser Gly Leu Phe Leu Tyr Gln Gly Leu Leu Gln
                165                 170
```

(2) INFORMATION FOR SEQ ID NO:100:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:100:

```
Asp Phe Ala Thr Thr Ile Trp Gln Gln Met Glu Glu Leu Gly Met Ala
 1               5                  10                  15
Pro Ala Leu Gln Pro Thr Gln Gly Ala Met Pro Ala Phe Ala Ser Ala
                20                  25                  30
Phe Gln Arg Arg Ala Gly Gly Val Leu Val Ala Ser His Leu Gln Ser
             35                  40                  45
Phe Leu Glu Val Ser Tyr Arg Val Leu Arg His Leu Ala Gln Pro Thr
 50                  55                  60
Pro Leu Gly Pro Ala Ser Ser Leu Pro Gln Ser Phe Leu Leu Lys Ser
 65                  70                  75                  80
Leu Glu Gln Val Arg Lys Ile Gln Gly Asp Gly Ala Ala Leu Gln Glu
                 85                  90                  95
Lys Leu Cys Ala Thr Tyr Lys Leu Cys His Pro Glu Glu Leu Val Leu
                100                 105                 110
Leu Gly His Ser Leu Gly Ile Pro Trp Ala Pro Leu Ser Ser Cys Pro
            115                 120                 125
Ser Gln Ala Leu Gln Leu Ala Gly Cys Leu Ser Gln Leu His Ser Gly
            130                 135                 140
Leu Phe Leu Tyr Gln Gly Leu Leu Gln Ala Leu Glu Gly Ile Ser Pro
145                 150                 155                 160
Glu Leu Gly Pro Thr Leu Asp Thr Leu Gln Leu Asp Val Ala
                165                 170
```

(2) INFORMATION FOR SEQ ID NO:101:

(i) SEQUENCE CHARACTERISTICS:

(A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:101:

Ile Trp Gln Gln Met Glu Glu Leu Gly Met Ala Pro Ala Leu Gln Pro
1               5                   10                  15

Thr Gln Gly Ala Met Pro Ala Phe Ala Ser Ala Phe Gln Arg Arg Ala
            20                  25                  30

Gly Gly Val Leu Val Ala Ser His Leu Gln Ser Phe Leu Glu Val Ser
        35                  40                  45

Tyr Arg Val Leu Arg His Leu Ala Gln Pro Thr Pro Leu Gly Pro Ala
50                  55                  60

Ser Ser Leu Pro Gln Ser Phe Leu Leu Lys Ser Leu Glu Gln Val Arg
65                  70                  75                  80

Lys Ile Gln Gly Asp Gly Ala Ala Leu Gln Glu Lys Leu Cys Ala Thr
                85                  90                  95

Tyr Lys Leu Cys His Pro Glu Glu Leu Val Leu Leu Gly His Ser Leu
                100                 105                 110

Gly Ile Pro Trp Ala Pro Leu Ser Ser Cys Pro Ser Gln Ala Leu Gln
            115                 120                 125

Leu Ala Gly Cys Leu Ser Gln Leu His Ser Gly Leu Phe Leu Tyr Gln
130                 135                 140

Gly Leu Leu Gln Ala Leu Glu Gly Ile Ser Pro Glu Leu Gly Pro Thr
145                 150                 155                 160

Leu Asp Thr Leu Gln Leu Asp Val Ala Asp Phe Ala Thr Thr
                165                 170

(2) INFORMATION FOR SEQ ID NO:102:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:102:

Gln Gln Met Glu Glu Leu Gly Met Ala Pro Ala Leu Gln Pro Thr Gln
1               5                   10                  15

Gly Ala Met Pro Ala Phe Ala Ser Ala Phe Gln Arg Arg Ala Gly Gly
            20                  25                  30

Val Leu Val Ala Ser His Leu Gln Ser Phe Leu Glu Val Ser Tyr Arg
        35                  40                  45

Val Leu Arg His Leu Ala Gln Pro Thr Pro Leu Gly Pro Ala Ser Ser
50                  55                  60

Leu Pro Gln Ser Phe Leu Leu Lys Ser Leu Glu Gln Val Arg Lys Ile
65                  70                  75                  80

Gln Gly Asp Gly Ala Ala Leu Gln Glu Lys Leu Cys Ala Thr Tyr Lys
                85                  90                  95

Leu Cys His Pro Glu Glu Leu Val Leu Leu Gly His Ser Leu Gly Ile
                100                 105                 110

Pro Trp Ala Pro Leu Ser Ser Cys Pro Ser Gln Ala Leu Gln Leu Ala
            115                 120                 125

```
Gly Cys Leu Ser Gln Leu His Ser Gly Leu Phe Leu Tyr Gln Gly Leu
        130                 135                 140

Leu Gln Ala Leu Glu Gly Ile Ser Pro Glu Leu Gly Pro Thr Leu Asp
145                 150                 155                 160

Thr Leu Gln Leu Asp Val Ala Asp Phe Ala Thr Thr Ile Trp
                165                 170
```

(2) INFORMATION FOR SEQ ID NO:103:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:103:

```
Leu Leu Gly His Ser Leu Gly Ile Pro Trp Ala Pro Leu Ser Ser Cys
1               5                   10                  15

Pro Ser Gln Ala Leu Gln Leu Ala Gly Cys Leu Ser Gln Leu His Ser
            20                  25                  30

Gly Leu Phe Leu Tyr Gln Gly Leu Leu Gln Ala Leu Glu Gly Ile Ser
        35                  40                  45

Pro Glu Leu Gly Pro Thr Leu Asp Thr Leu Gln Leu Asp Val Ala Asp
    50                  55                  60

Phe Ala Thr Thr Ile Trp Gln Gln Met Glu Glu Leu Gly Met Ala Pro
65                  70                  75                  80

Ala Leu Gln Pro Thr Gln Gly Ala Met Pro Ala Phe Ala Ser Ala Phe
                85                  90                  95

Gln Arg Arg Ala Gly Gly Val Leu Val Ala Ser His Leu Gln Ser Phe
            100                 105                 110

Leu Glu Val Ser Tyr Arg Val Leu Arg His Leu Ala Gln Pro Thr Pro
        115                 120                 125

Leu Gly Pro Ala Ser Ser Leu Pro Gln Ser Phe Leu Leu Lys Ser Leu
    130                 135                 140

Glu Gln Val Arg Lys Ile Gln Gly Asp Gly Ala Ala Leu Gln Glu Lys
145                 150                 155                 160

Leu Cys Ala Thr Tyr Lys Leu Cys His Pro Glu Glu Leu Val
                165                 170
```

(2) INFORMATION FOR SEQ ID NO:104:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:104:

```
CAGAGCTTCC TGCTCAAGTC TTTAGAGCAA GTGAGGAAGA TCCAGGGCGA TGGCGCAGCG      60

CTCCAGGAGA AGCTGTGTGC CACCTACAAG CTGTGCCACC CCGAGGAGCT GGTGCTGCTC     120

GGACACTCTC TGGGCATCCC CTGGGCTCCC CTGAGCTCCT GCCCCAGCCA GGCCCTGCAG     180

CTGGCAGGCT GCTTGAGCCA ACTCCATAGC GGCCTTTTCC TCTACCAGGG GCTCCTGCAG     240

GCCCTGGAAG GGATATCCCC CGAGTTGGGT CCCACCTTGG ACACACTGCA GCTGGACGTC     300
```

```
GCCGACTTTG CCACCACCAT CTGGCAGCAG ATGGAAGAAC TGGGAATGGC CCCTGCCCTG      360

CAGCCCACCC AGGGTGCCAT GCCGGCCTTC GCCTCTGCTT TCCAGCGCCG GGCAGGAGGG      420

GTCCTGGTTG CTAGCCATCT GCAGAGCTTC CTGGAGGTGT CGTACCGCGT TCTACGCCAC      480

CTTGCGCAGC CCGACATGGC TACACCATTA GGCCCTGCCA GCTCCCTGCC C              531
```

(2) INFORMATION FOR SEQ ID NO:105:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:105:

```
GAACTGGGAA TGGCCCCTGC CCTGCAGCCC ACCCAGGGTG CCATGCCGGC CTTCGCCTCT       60

GCTTTCCAGC GCCGGGCAGG AGGGGTCCTG GTTGCTAGCC ATCTGCAGAG CTTCCTGGAG      120

GTGTCGTACC GCGTTCTACG CCACCTTGCG CAGCCCGACA TGGCTACACC ATTAGGCCCT      180

GCCAGCTCCC TGCCCCAGAG CTTCCTGCTC AAGTCTTTAG AGCAAGTGAG GAAGATCCAG      240

GGCGATGGCG CAGCGCTCCA GGAGAAGCTG TGTGCCACCT ACAAGCTGTG CCACCCCGAG      300

GAGCTGGTGC TGCTCGGACA CTCTCTGGGC ATCCCCTGGG CTCCCCTGAG CTCCTGCCCC      360

AGCCAGGCCC TGCAGCTGGC AGGCTGCTTG AGCCAACTCC ATAGCGGCCT TTTCCTCTAC      420

CAGGGGCTCC TGCAGGCCCT GGAAGGGATA TCCCCCGAGT TGGGTCCCAC CTTGGACACA      480

CTGCAGCTGG ACGTCGCCGA CTTTGCCACC ACCATCTGGC AGCAGATGGA A              531
```

(2) INFORMATION FOR SEQ ID NO:106:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:106:

```
GGAATGGCCC CTGCCCTGCA GCCCACCCAG GGTGCCATGC CGGCCTTCGC CTCTGCTTTC       60

CAGCGCCGGG CAGGAGGGGT CCTGGTTGCT AGCCATCTGC AGAGCTTCCT GGAGGTGTCG      120

TACCGCGTTC TACGCCACCT TGCGCAGCCC GACATGGCTA CACCATTAGG CCCTGCCAGC      180

TCCCTGCCCC AGAGCTTCCT GCTCAAGTCT TTAGAGCAAG TGAGGAAGAT CCAGGGCGAT      240

GGCGCAGCGC TCCAGGAGAA GCTGTGTGCC ACCTACAAGC TGTGCCACCC CGAGGAGCTG      300

GTGCTGCTCG GACACTCTCT GGGCATCCCC TGGGCTCCCC TGAGCTCCTG CCCCAGCCAG      360

GCCCTGCAGC TGGCAGGCTG CTTGAGCCAA CTCCATAGCG GCCTTTTCCT CTACCAGGGG      420

CTCCTGCAGG CCCTGGAAGG GATATCCCCC GAGTTGGGTC CCACCTTGGA CACACTGCAG      480

CTGGACGTCG CCGACTTTGC CACCACCATC TGGCAGCAGA TGGAAGAACT G              531
```

(2) INFORMATION FOR SEQ ID NO:107:

(i) SEQUENCE CHARACTERISTICS:
        (A) LENGTH: 531 base pairs
        (B) TYPE: nucleic acid
        (C) STRANDEDNESS: unknown (D) TOPOLOGY: unknown (ii) MOLECULE TYPE: other nucleic acid
            (A) DESCRIPTION: /desc = "synthetic"

(xi) SEQUENCE DESCRIPTION: SEQ ID NO:107:

| | | | | | |
|---|---|---|---|---|---|
| TTCCTGCTCA | AGTCTTTAGA | GCAAGTGAGG | AAGATCCAGG | GCGATGGCGC | AGCGCTCCAG | 60 |
| GAGAAGCTGT | GTGCCACCTA | CAAGCTGTGC | CACCCCGAGG | AGCTGGTGCT | GCTCGGACAC | 120 |
| TCTCTGGGCA | TCCCCTGGGC | TCCCCTGAGC | TCCTGCCCCA | GCCAGGCCCT | GCAGCTGGCA | 180 |
| GGCTGCTTGA | GCCAACTCCA | TAGCGGCCTT | TTCCTCTACC | AGGGGCTCCT | GCAGGCCCTG | 240 |
| GAAGGGATAT | CCCCCGAGTT | GGGTCCCACC | TTGGACACAC | TGCAGCTGGA | CGTCGCCGAC | 300 |
| TTTGCCACCA | CCATCTGGCA | GCAGATGGAA | GAACTGGGAA | TGGCCCCTGC | CCTGCAGCCC | 360 |
| ACCCAGGGTG | CCATGCCGGC | CTTCGCCTCT | GCTTTCCAGC | GCCGGGCAGG | AGGGGTCCTG | 420 |
| GTTGCTAGCC | ATCTGCAGAG | CTTCCTGGAG | GTGTCGTACC | GCGTTCTACG | CCACCTTGCG | 480 |
| CAGCCCGACA | TGGCTACACC | ATTAGGCCCT | GCCAGCTCCC | TGCCCCAGAG C | | 531 |

(2) INFORMATION FOR SEQ ID NO:108:

(i) SEQUENCE CHARACTERISTICS:
            (A) LENGTH: 531 base pairs
            (B) TYPE: nucleic acid
            (C) STRANDEDNESS: unknown
            (D) TOPOLOGY: unknown (ii) MOLECULE TYPE: other nucleic acid
            (A) DESCRIPTION: /desc = "synthetic"

(xi) SEQUENCE DESCRIPTION: SEQ ID NO:108:

| | | | | | |
|---|---|---|---|---|---|
| AGCTTCCTGG | AGGTGTCGTA | CCGCGTTCTA | CGCCACCTTG | CGCAGCCCGA | CATGGCTACA | 60 |
| CCATTAGGCC | CTGCCAGCTC | CCTGCCCCAG | AGCTTCCTGC | TCAAGTCTTT | AGAGCAAGTG | 120 |
| AGGAAGATCC | AGGGCGATGG | CGCAGCGCTC | CAGGAGAAGC | TGTGTGCCAC | CTACAAGCTG | 180 |
| TGCCACCCCG | AGGAGCTGGT | GCTGCTCGGA | CACTCTCTGG | GCATCCCCTG | GGCTCCCCTG | 240 |
| AGCTCCTGCC | CCAGCCAGGC | CCTGCAGCTG | GCAGGCTGCT | TGAGCCAACT | CCATAGCGGC | 300 |
| CTTTTCCTCT | ACCAGGGGCT | CCTGCAGGCC | CTGGAAGGGA | TATCCCCCGA | GTTGGGTCCC | 360 |
| ACCTTGGACA | CACTGCAGCT | GGACGTCGCC | GACTTTGCCA | CCACCATCTG | GCAGCAGATG | 420 |
| GAAGAACTGG | GAATGGCCCC | TGCCCTGCAG | CCCACCCAGG | GTGCCATGCC | GGCCTTCGCC | 480 |
| TCTGCTTTCC | AGCGCCGGGC | AGGAGGGGTC | CTGGTTGCTA | GCCATCTGCA G | | 531 |

(2) INFORMATION FOR SEQ ID NO:109:

(i) SEQUENCE CHARACTERISTICS:
            (A) LENGTH: 531 base pairs
            (B) TYPE: nucleic acid
            (C) STRANDEDNESS: unknown
            (D) TOPOLOGY: unknown (ii) MOLECULE TYPE: other nucleic acid
            (A) DESCRIPTION: /desc = "synthetic"

(xi) SEQUENCE DESCRIPTION: SEQ ID NO:109:

| | | | | | |
|---|---|---|---|---|---|
| AGCTTCCTGG | AGGTGTCGTA | CCGCGTTCTA | CGCCACCTTG | CGCAGCCCGA | CATGGCTACA | 60 |
| CCATTAGGCC | CTGCCAGCTC | CCTGCCCCAG | AGCTTCCTGC | TCAAGTCTTT | AGAGCAAGTG | 120 |
| AGGAAGATCC | AGGGCGATGG | CGCAGCGCTC | CAGGAGAAGC | TGTGTGCCAC | CTACAAGCTG | 180 |
| TGCCACCCCG | AGGAGCTGGT | GCTGCTCGGA | CACTCTCTGG | GCATCCCCTG | GGCTCCCCTG | 240 |

```
AGCTCCTGCC CCAGCCAGGC CCTGCAGCTG GCAGGCTGCT TGAGCCAACT CCATAGCGGC      300

CTTTTCCTCT ACCAGGGGCT CCTGCAGGCC CTGGAAGGGA TATCCCCCGA GTTGGGTCCC      360

ACCTTGGACA CACTGCAGCT GGACGTCGCC GACTTTGCCA CCACCATCTG GCAGCAGATG      420

GAAGAACTGG GAATGGCCCC TGCCCTGCAG CCCACCCAGG GTGCCATGCC GGCCTTCGCC      480

TCTGCTTTCC AGCGCCGGGC AGGAGGGGTC CTGGTTGCTA GCCATCTGCA G              531
```

(2) INFORMATION FOR SEQ ID NO:110:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:110:

```
TTAGGCCCTG CCAGCTCCCT GCCCCAGAGC TTCCTGCTCA AGTCTTTAGA GCAAGTGAGG       60

AAGATCCAGG GCGATGGCGC AGCGCTCCAG GAGAAGCTGT GTGCCACCTA CAAGCTGTGC      120

CACCCCGAGG AGCTGGTGCT GCTCGGACAC TCTCTGGGCA TCCCCTGGGC TCCCCTGAGC      180

TCCTGCCCCA GCCAGGCCCT GCAGCTGGCA GGCTGCTTGA GCCAACTCCA TAGCGGCCTT      240

TTCCTCTACC AGGGGCTCCT GCAGGCCCTG GAAGGGATAT CCCCCGAGTT GGGTCCCACC      300

TTGGACACAC TGCAGCTGGA CGTCGCCGAC TTTGCCACCA CCATCTGGCA GCAGATGGAA      360

GAACTGGGAA TGGCCCCTGC CCTGCAGCCC ACCCAGGGTG CCATGCCGGC CTTCGCCTCT      420

GCTTTCCAGC GCCGGGCAGG AGGGGTCCTG GTTGCTAGCC ATCTGCAGAG CTTCCTGGAG      480

GTGTCGTACC GCGTTCTACG CCACCTTGCG CAGCCCGACA TGGCTACACC A              531
```

(2) INFORMATION FOR SEQ ID NO:111:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:111:

```
CTGCTCGGAC ACTCTCTGGG CATCCCCTGG GCTCCCCTGA GCTCCTGCCC CAGCCAGGCC       60

CTGCAGCTGG CAGGCTGCTT GAGCCAACTC CATAGCGGCC TTTTCCTCTA CCAGGGGCTC      120

CTGCAGGCCC TGGAAGGGAT ATCCCCCGAG TTGGGTCCCA CCTTGGACAC ACTGCAGCTG      180

GACGTCGCCG ACTTTGCCAC CACCATCTGG CAGCAGATGG AAGAACTGGG AATGGCCCCT      240

GCCCTGCAGC CCACCCAGGG TGCCATGCCG GCCTTCGCCT CTGCTTTCCA GCGCCGGGCA      300

GGAGGGGTCC TGGTTGCTAG CCATCTGCAG AGCTTCCTGG AGGTGTCGTA CCGCGTTCTA      360

CGCCACCTTG CGCAGCCCGA CATGGCTACA CCATTAGGCC CTGCCAGCTC CCTGCCCCAG      420

AGCTTCCTGC TCAAGTCTTT AGAGCAAGTG AGGAAGATCC AGGGCGATGG CGCAGCGCTC      480

CAGGAGAAGC TGTGTGCCAC CTACAAGCTG TGCCACCCCG AGGAGCTGGT G              531
```

(2) INFORMATION FOR SEQ ID NO:112:

(i) SEQUENCE CHARACTERISTICS:
        (A) LENGTH: 531 base pairs (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:112:

```
CCCCTGAGCT CCTGCCCCAG CCAGGCCCTG CAGCTGGCAG GCTGCTTGAG CCAACTCCAT      60

AGCGGCCTTT TCCTCTACCA GGGGCTCCTG CAGGCCCTGG AAGGGATATC CCCCGAGTTG     120

GGTCCCACCT TGGACACACT GCAGCTGGAC GTCGCCGACT TGCCACCAC  CATCTGGCAG     180

CAGATGGAAG AACTGGGAAT GGCCCCTGCC CTGCAGCCCA CCCAGGGTGC CATGCCGGCC     240

TTCGCCTCTG CTTTCCAGCG CCGGGCAGGA GGGGTCCTGG TTGCTAGCCA TCTGCAGAGC     300

TTCCTGGAGG TGTCGTACCG CGTTCTACGC CACCTTGCGC AGCCCGACAT GGCTACACCA     360

TTAGGCCCTG CCAGCTCCCT GCCCCAGAGC TTCCTGCTCA AGTCTTTAGA GCAAGTGAGG     420

AAGATCCAGG GCGATGGCGC AGCGCTCCAG GAGAAGCTGT GTGCCACCTA CAAGCTGTGC     480

CACCCCGAGG AGCTGGTGCT GCTCGGACAC TCTCTGGGCA TCCCCTGGGC T             531
```

(2) INFORMATION FOR SEQ ID NO:113:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:113:

```
CAGGCCCTGC AGCTGGCAGG CTGCTTGAGC CAACTCCATA GCGGCCTTTT CCTCTACCAG      60

GGGCTCCTGC AGGCCCTGGA AGGGATATCC CCCGAGTTGG GTCCCACCTT GGACACACTG     120

CAGCTGGACG TCGCCGACTT TGCCACCACC ATCTGGCAGC AGATGGAAGA ACTGGGAATG     180

GCCCCTGCCC TGCAGCCCAC CCAGGGTGCC ATGCCGGCCT TCGCCTCTGC TTTCCAGCGC     240

CGGGCAGGAG GGGTCCTGGT TGCTAGCCAT CTGCAGAGCT TCCTGGAGGT GTCGTACCGC     300

GTTCTACGCC ACCTTGCGCA GCCCGACATG GCTACACCAT TAGGCCCTGC CAGCTCCCTG     360

CCCCAGAGCT TCCTGCTCAA GTCTTTAGAG CAAGTGAGGA AGATCCAGGG CGATGGCGCA     420

GCGCTCCAGG AGAAGCTGTG TGCCACCTAC AAGCTGTGCC ACCCCGAGGA GCTGGTGCTG     480

CTCGGACACT CTCTGGGCAT CCCCTGGGCT CCCCTGAGCT CCTGCCCCAG C             531
```

(2) INFORMATION FOR SEQ ID NO:114:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:114:

```
CTGCAGCTGG CAGGCTGCTT GAGCCAACTC CATAGCGGCC TTTTCCTCTA CCAGGGGCTC      60

CTGCAGGCCC TGGAAGGGAT ATCCCCCGAG TTGGGTCCCA CCTTGGACAC ACTGCAGCTG     120

GACGTCGCCG ACTTTGCCAC CACCATCTGG CAGCAGATGG AAGAACTGGG AATGGCCCCT     180
```

```
GCCCTGCAGC CCACCCAGGG TGCCATGCCG GCCTTCGCCT CTGCTTTCCA GCGCCGGGCA      240

GGAGGGGTCC TGGTTGCTAG CCATCTGCAG AGCTTCCTGG AGGTGTCGTA CCGCGTTCTA      300

CGCCACCTTG CGCAGCCCGA CATGGCTACA CCATTAGGCC CTGCCAGCTC CCTGCCCCAG      360

AGCTTCCTGC TCAAGTCTTT AGAGCAAGTG AGGAAGATCC AGGGCGATGG CGCAGCGCTC      420

CAGGAGAAGC TGTGTGCCAC CTACAAGCTG TGCCACCCCG AGGAGCTGGT GCTGCTCGGA      480

CACTCTCTGG GCATCCCCTG GGCTCCCCTG AGCTCCTGCC CCAGCCAGGC C               531
```

(2) INFORMATION FOR SEQ ID NO:115:

(i) SEQUENCE CHARACTERISTICS:
        (A) LENGTH: 531 base pairs
        (B) TYPE: nucleic acid
        (C) STRANDEDNESS: unknown
        (D) TOPOLOGY: unknown (ii) MOLECULE TYPE: other nucleic acid
        (A) DESCRIPTION: /desc = "synthetic"

(xi) SEQUENCE DESCRIPTION: SEQ ID NO:115:

```
CTGGCAGGCT GCTTGAGCCA ACTCCATAGC GGCCTTTTCC TCTACCAGGG GCTCCTGCAG       60

GCCCTGGAAG GGATATCCCC CGAGTTGGGT CCCACCTTGG ACACACTGCA GCTGGACGTC      120

GCCGACTTTG CCACCACCAT CTGGCAGCAG ATGGAAGAAC TGGGAATGGC CCCTGCCCTG      180

CAGCCCACCC AGGGTGCCAT GCCGGCCTTC GCCTCTGCTT TCCAGCGCCG GGCAGGAGGG      240

GTCCTGGTTG CTAGCCATCT GCAGAGCTTC CTGGAGGTGT CGTACCGCGT TCTACGCCAC      300

CTTGCGCAGC CCGACATGGC TACACCATTA GGCCCTGCCA GCTCCCTGCC CCAGAGCTTC      360

CTGCTCAAGT CTTTAGAGCA AGTGAGGAAG ATCCAGGGCG ATGGCGCAGC GCTCCAGGAG      420

AAGCTGTGTG CCACCTACAA GCTGTGCCAC CCCGAGGAGC TGGTGCTGCT CGGACACTCT      480

CTGGGCATCC CCTGGGCTCC CCTGAGCTCC TGCCCCAGCC AGGCCCTGCA G               531
```

(2) INFORMATION FOR SEQ ID NO:116:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:116:

```
Gln Ser Phe Leu Leu Lys Ser Leu Glu Gln Val Arg Lys Ile Gln Gly
1               5                  10                  15

Asp Gly Ala Ala Leu Gln Glu Lys Leu Cys Ala Thr Tyr Lys Leu Cys
                20                  25                  30

His Pro Glu Glu Leu Val Leu Leu Gly His Ser Leu Gly Ile Pro Trp
            35                  40                  45

Ala Pro Leu Ser Ser Cys Pro Ser Gln Ala Leu Gln Leu Ala Gly Cys
        50                  55                  60

Leu Ser Gln Leu His Ser Gly Leu Phe Leu Tyr Gln Gly Leu Leu Gln
65                  70                  75                  80

Ala Leu Glu Gly Ile Ser Pro Glu Leu Gly Pro Thr Leu Asp Thr Leu
                85                  90                  95

Gln Leu Asp Val Ala Asp Phe Ala Thr Thr Ile Trp Gln Gln Met Glu
            100                 105                 110

Glu Leu Gly Met Ala Pro Ala Leu Gln Pro Thr Gln Gly Ala Met Pro
```

-continued

```
            115                 120                 125
Ala Phe Ala Ser Ala Phe Gln Arg Arg Ala Gly Gly Val Leu Val Ala
        130                 135                 140

Ser His Leu Gln Ser Phe Leu Glu Val Ser Tyr Arg Val Leu Arg His
145                 150                 155                 160

Leu Ala Gln Pro Asp Met Ala Thr Pro Leu Gly Pro Ala Ser Ser Leu
                165                 170                 175

Pro
```

(2) INFORMATION FOR SEQ ID NO:117:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:117:

```
Glu Leu Gly Met Ala Pro Ala Leu Gln Pro Thr Gln Gly Ala Met Pro
1               5                   10                  15

Ala Phe Ala Ser Ala Phe Gln Arg Arg Ala Gly Gly Val Leu Val Ala
                20                  25                  30

Ser His Leu Gln Ser Phe Leu Glu Val Ser Tyr Arg Val Leu Arg His
            35                  40                  45

Leu Ala Gln Pro Asp Met Ala Thr Pro Leu Gly Pro Ala Ser Ser Leu
        50                  55                  60

Pro Gln Ser Phe Leu Leu Lys Ser Leu Glu Gln Val Arg Lys Ile Gln
65                  70                  75                  80

Gly Asp Gly Ala Ala Leu Gln Glu Lys Leu Cys Ala Thr Tyr Lys Leu
                85                  90                  95

Cys His Pro Glu Glu Leu Val Leu Leu Gly His Ser Leu Gly Ile Pro
            100                 105                 110

Trp Ala Pro Leu Ser Ser Cys Pro Ser Gln Ala Leu Gln Leu Ala Gly
        115                 120                 125

Cys Leu Ser Gln Leu His Ser Gly Leu Phe Leu Tyr Gln Gly Leu Leu
    130                 135                 140

Gln Ala Leu Glu Gly Ile Ser Pro Glu Leu Gly Pro Thr Leu Asp Thr
145                 150                 155                 160

Leu Gln Leu Asp Val Ala Asp Phe Ala Thr Thr Ile Trp Gln Gln Met
                165                 170                 175

Glu
```

(2) INFORMATION FOR SEQ ID NO:118:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:118:

```
Gly Met Ala Pro Ala Leu Gln Pro Thr Gln Gly Ala Met Pro Ala Phe
1               5                   10                  15

Ala Ser Ala Phe Gln Arg Arg Ala Gly Gly Val Leu Val Ala Ser His
                20                  25                  30
```

```
Leu Gln Ser Phe Leu Glu Val Ser Tyr Arg Val Leu Arg His Leu Ala
            35                  40                  45

Gln Pro Asp Met Ala Thr Pro Leu Gly Pro Ala Ser Ser Leu Pro Gln
 50                  55                  60

Ser Phe Leu Leu Lys Ser Leu Glu Gln Val Arg Lys Ile Gln Gly Asp
 65                  70                  75                  80

Gly Ala Ala Leu Gln Glu Lys Leu Cys Ala Thr Tyr Lys Leu Cys His
                 85                  90                  95

Pro Glu Glu Leu Val Leu Leu Gly His Ser Leu Gly Ile Pro Trp Ala
                100                 105                 110

Pro Leu Ser Ser Cys Pro Ser Gln Ala Leu Gln Leu Ala Gly Cys Leu
            115                 120                 125

Ser Gln Leu His Ser Gly Leu Phe Leu Tyr Gln Gly Leu Leu Gln Ala
    130                 135                 140

Leu Glu Gly Ile Ser Pro Glu Leu Gly Pro Thr Leu Asp Thr Leu Gln
145                 150                 155                 160

Leu Asp Val Ala Asp Phe Ala Thr Thr Ile Trp Gln Gln Met Glu Glu
                165                 170                 175

Leu (2) INFORMATION FOR SEQ ID NO:119:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:119:

Phe Leu Leu Lys Ser Leu Glu Gln Val Arg Lys Ile Gln Gly Asp Gly
 1               5                  10                  15

Ala Ala Leu Gln Glu Lys Leu Cys Ala Thr Tyr Lys Leu Cys His Pro
                20                  25                  30

Glu Glu Leu Val Leu Leu Gly His Ser Leu Gly Ile Pro Trp Ala Pro
            35                  40                  45

Leu Ser Ser Cys Pro Ser Gln Ala Leu Gln Leu Ala Gly Cys Leu Ser
 50                  55                  60

Gln Leu His Ser Gly Leu Phe Leu Tyr Gln Gly Leu Leu Gln Ala Leu
 65                  70                  75                  80

Glu Gly Ile Ser Pro Glu Leu Gly Pro Thr Leu Asp Thr Leu Gln Leu
                 85                  90                  95

Asp Val Ala Asp Phe Ala Thr Thr Ile Trp Gln Gln Met Glu Glu Leu
                100                 105                 110

Gly Met Ala Pro Ala Leu Gln Pro Thr Gln Gly Ala Met Pro Ala Phe
            115                 120                 125

Ala Ser Ala Phe Gln Arg Arg Ala Gly Gly Val Leu Val Ala Ser His
    130                 135                 140

Leu Gln Ser Phe Leu Glu Val Ser Tyr Arg Val Leu Arg His Leu Ala
145                 150                 155                 160

Gln Pro Asp Met Ala Thr Pro Leu Gly Pro Ala Ser Ser Leu Pro Gln
                165                 170                 175

Ser
```

(2) INFORMATION FOR SEQ ID NO:120:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:120:

```
Ser Phe Leu Glu Val Ser Tyr Arg Val Leu Arg His Leu Ala Gln Pro
  1               5                  10                  15

Asp Met Ala Thr Pro Leu Gly Pro Ala Ser Ser Leu Pro Gln Ser Phe
             20                  25                  30

Leu Leu Lys Ser Leu Glu Gln Val Arg Lys Ile Gln Gly Asp Gly Ala
         35                  40                  45

Ala Leu Gln Glu Lys Leu Cys Ala Thr Tyr Lys Leu Cys His Pro Glu
 50                  55                  60

Glu Leu Val Leu Leu Gly His Ser Leu Gly Ile Pro Trp Ala Pro Leu
 65                  70                  75                  80

Ser Ser Cys Pro Ser Gln Ala Leu Gln Leu Ala Gly Cys Leu Ser Gln
                 85                  90                  95

Leu His Ser Gly Leu Phe Leu Tyr Gln Gly Leu Leu Gln Ala Leu Glu
                100                 105                 110

Gly Ile Ser Pro Glu Leu Gly Pro Thr Leu Asp Thr Leu Gln Leu Asp
            115                 120                 125

Val Ala Asp Phe Ala Thr Thr Ile Trp Gln Gln Met Glu Glu Leu Gly
130                 135                 140

Met Ala Pro Ala Leu Gln Pro Thr Gln Gly Ala Met Pro Ala Phe Ala
145                 150                 155                 160

Ser Ala Phe Gln Arg Arg Ala Gly Gly Val Leu Val Ala Ser His Leu
                165                 170                 175

Gln
```

(2) INFORMATION FOR SEQ ID NO:121:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:121:

```
Glu Gln Val Arg Lys Ile Gln Gly Asp Gly Ala Ala Leu Gln Glu Lys
  1               5                  10                  15

Leu Cys Ala Thr Tyr Lys Leu Cys His Pro Glu Glu Leu Val Leu Leu
             20                  25                  30

Gly His Ser Leu Gly Ile Pro Trp Ala Pro Leu Ser Ser Cys Pro Ser
         35                  40                  45

Gln Ala Leu Gln Leu Ala Gly Cys Leu Ser Gln Leu His Ser Gly Leu
 50                  55                  60

Phe Leu Tyr Gln Gly Leu Leu Gln Ala Leu Glu Gly Ile Ser Pro Glu
 65                  70                  75                  80

Leu Gly Pro Thr Leu Asp Thr Leu Gln Leu Asp Val Ala Asp Phe Ala
                 85                  90                  95

Thr Thr Ile Trp Gln Gln Met Glu Glu Leu Gly Met Ala Pro Ala Leu
```

```
                100               105                110
Gln Pro Thr Gln Gly Ala Met Pro Ala Phe Ala Ser Ala Phe Gln Arg
            115                 120                 125

Arg Ala Gly Gly Val Leu Val Ala Ser His Leu Gln Ser Phe Leu Glu
    130                 135                 140

Val Ser Tyr Arg Val Leu Arg His Leu Ala Gln Pro Asp Met Ala Thr
145                 150                 155                 160

Pro Leu Gly Pro Ala Ser Ser Leu Pro Gln Ser Phe Leu Leu Lys Ser
                165                 170                 175

Leu (2) INFORMATION FOR SEQ ID NO:122:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:122:

Leu Gly Pro Ala Ser Ser Leu Pro Gln Ser Phe Leu Leu Lys Ser Leu
1               5                   10                  15

Glu Gln Val Arg Lys Ile Gln Gly Asp Gly Ala Ala Leu Gln Glu Lys
            20                  25                  30

Leu Cys Ala Thr Tyr Lys Leu Cys His Pro Glu Glu Leu Val Leu Leu
            35                  40                  45

Gly His Ser Leu Gly Ile Pro Trp Ala Pro Leu Ser Ser Cys Pro Ser
        50                  55                  60

Gln Ala Leu Gln Leu Ala Gly Cys Leu Ser Gln Leu His Ser Gly Leu
65                  70                  75                  80

Phe Leu Tyr Gln Gly Leu Leu Gln Ala Leu Glu Gly Ile Ser Pro Glu
                85                  90                  95

Leu Gly Pro Thr Leu Asp Thr Leu Gln Leu Asp Val Ala Asp Phe Ala
            100                 105                 110

Thr Thr Ile Trp Gln Gln Met Glu Glu Leu Gly Met Ala Pro Ala Leu
            115                 120                 125

Gln Pro Thr Gln Gly Ala Met Pro Ala Phe Ala Ser Ala Phe Gln Arg
            130                 135                 140

Arg Ala Gly Gly Val Leu Val Ala Ser His Leu Gln Ser Phe Leu Glu
145                 150                 155                 160

Val Ser Tyr Arg Val Leu Arg His Leu Ala Gln Pro Asp Met Ala Thr
                165                 170                 175

Pro (2) INFORMATION FOR SEQ ID NO:123:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:123:

Leu Leu Gly His Ser Leu Gly Ile Pro Trp Ala Pro Leu Ser Ser Cys
1               5                   10                  15
```

```
Pro Ser Gln Ala Leu Gln Leu Ala Gly Cys Leu Ser Gln Leu His Ser
            20                  25                  30

Gly Leu Phe Leu Tyr Gln Gly Leu Leu Gln Ala Leu Glu Gly Ile Ser
            35                  40                  45

Pro Glu Leu Gly Pro Thr Leu Asp Thr Leu Gln Leu Asp Val Ala Asp
 50                      55                  60

Phe Ala Thr Thr Ile Trp Gln Gln Met Glu Glu Leu Gly Met Ala Pro
 65                  70                  75                  80

Ala Leu Gln Pro Thr Gln Gly Ala Met Pro Ala Phe Ala Ser Ala Phe
                85                  90                  95

Gln Arg Arg Ala Gly Gly Val Leu Val Ala Ser His Leu Gln Ser Phe
            100                 105                 110

Leu Glu Val Ser Tyr Arg Val Leu Arg His Leu Ala Gln Pro Asp Met
            115                 120                 125

Ala Thr Pro Leu Gly Pro Ala Ser Ser Leu Pro Gln Ser Phe Leu Leu
 130                 135                 140

Lys Ser Leu Glu Gln Val Arg Lys Ile Gln Gly Asp Gly Ala Ala Leu
145                 150                 155                 160

Gln Glu Lys Leu Cys Ala Thr Tyr Lys Leu Cys His Pro Glu Glu Leu
            165                 170                 175

Val (2) INFORMATION FOR SEQ ID NO:124:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:124:

Pro Leu Ser Ser Cys Pro Ser Gln Ala Leu Gln Leu Ala Gly Cys Leu
 1               5                  10                  15

Ser Gln Leu His Ser Gly Leu Phe Leu Tyr Gln Gly Leu Leu Gln Ala
            20                  25                  30

Leu Glu Gly Ile Ser Pro Glu Leu Gly Pro Thr Leu Asp Thr Leu Gln
            35                  40                  45

Leu Asp Val Ala Asp Phe Ala Thr Thr Ile Trp Gln Gln Met Glu Glu
 50                  55                  60

Leu Gly Met Ala Pro Ala Leu Gln Pro Thr Gln Gly Ala Met Pro Ala
 65                  70                  75                  80

Phe Ala Ser Ala Phe Gln Arg Arg Ala Gly Gly Val Leu Val Ala Ser
                85                  90                  95

His Leu Gln Ser Phe Leu Glu Val Ser Tyr Arg Val Leu Arg His Leu
            100                 105                 110

Ala Gln Pro Asp Met Ala Thr Pro Leu Gly Pro Ala Ser Ser Leu Pro
            115                 120                 125

Gln Ser Phe Leu Leu Lys Ser Leu Glu Gln Val Arg Lys Ile Gln Gly
 130                 135                 140

Asp Gly Ala Ala Leu Gln Glu Lys Leu Cys Ala Thr Tyr Lys Leu Cys
145                 150                 155                 160

His Pro Glu Glu Leu Val Leu Leu Gly His Ser Leu Gly Ile Pro Trp
            165                 170                 175
```

Ala (2) INFORMATION FOR SEQ ID NO:125:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:125:

```
Gln Ala Leu Gln Leu Ala Gly Cys Leu Ser Gln Leu His Ser Gly Leu
1               5                   10                  15

Phe Leu Tyr Gln Gly Leu Leu Gln Ala Leu Glu Gly Ile Ser Pro Glu
            20                  25                  30

Leu Gly Pro Thr Leu Asp Thr Leu Gln Leu Asp Val Ala Asp Phe Ala
                35                  40                  45

Thr Thr Ile Trp Gln Gln Met Glu Glu Leu Gly Met Ala Pro Ala Leu
        50                  55                  60

Gln Pro Thr Gln Gly Ala Met Pro Ala Phe Ala Ser Ala Phe Gln Arg
65                  70                  75                  80

Arg Ala Gly Gly Val Leu Val Ala Ser His Leu Gln Ser Phe Leu Glu
                85                  90                  95

Val Ser Tyr Arg Val Leu Arg His Leu Ala Gln Pro Asp Met Ala Thr
            100                 105                 110

Pro Leu Gly Pro Ala Ser Ser Leu Pro Gln Ser Phe Leu Leu Lys Ser
                115                 120                 125

Leu Glu Gln Val Arg Lys Ile Gln Gly Asp Gly Ala Ala Leu Gln Glu
            130                 135                 140

Lys Leu Cys Ala Thr Tyr Lys Leu Cys His Pro Glu Glu Leu Val Leu
145                 150                 155                 160

Leu Gly His Ser Leu Gly Ile Pro Trp Ala Pro Leu Ser Ser Cys Pro
                165                 170                 175

Ser
```

(2) INFORMATION FOR SEQ ID NO:126:

(i) SEQUENCE CHARACTERISTICS:
        (A) LENGTH: 177 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:126:

```
Leu Gln Leu Ala Gly Cys Leu Ser Gln Leu His Ser Gly Leu Phe Leu
1               5                   10                  15

Tyr Gln Gly Leu Leu Gln Ala Leu Glu Gly Ile Ser Pro Glu Leu Gly
            20                  25                  30

Pro Thr Leu Asp Thr Leu Gln Leu Asp Val Ala Asp Phe Ala Thr Thr
                35                  40                  45

Ile Trp Gln Gln Met Glu Glu Leu Gly Met Ala Pro Ala Leu Gln Pro
        50                  55                  60

Thr Gln Gly Ala Met Pro Ala Phe Ala Ser Ala Phe Gln Arg Arg Ala
65                  70                  75                  80

Gly Gly Val Leu Val Ala Ser His Leu Gln Ser Phe Leu Glu Val Ser
```

```
                      85                  90                  95
Tyr Arg Val Leu Arg His Leu Ala Gln Pro Asp Met Ala Thr Pro Leu
                100                 105                 110
Gly Pro Ala Ser Ser Leu Pro Gln Ser Phe Leu Leu Lys Ser Leu Glu
                115                 120                 125
Gln Val Arg Lys Ile Gln Gly Asp Gly Ala Ala Leu Gln Glu Lys Leu
    130                 135                 140
Cys Ala Thr Tyr Lys Leu Cys His Pro Glu Glu Leu Val Leu Leu Gly
145                 150                 155                 160
His Ser Leu Gly Ile Pro Trp Ala Pro Leu Ser Ser Cys Pro Ser Gln
                165                 170                 175
Ala
```

(2) INFORMATION FOR SEQ ID NO:127:

(i) SEQUENCE CHARACTERISTICS:
  (A) LENGTH: 177 amino acids
  (B) TYPE: amino acid
  (C) STRANDEDNESS: unknown
  (D) TOPOLOGY: unknown (ii) MOLECULE TYPE: peptide (xi) SEQUENCE DESCRIPTION: SEQ ID NO:127:

```
Leu Ala Gly Cys Leu Ser Gln Leu His Ser Gly Leu Phe Leu Tyr Gln
1               5                   10                  15
Gly Leu Leu Gln Ala Leu Glu Gly Ile Ser Pro Glu Leu Gly Pro Thr
                20                  25                  30
Leu Asp Thr Leu Gln Leu Asp Val Ala Asp Phe Ala Thr Thr Ile Trp
            35                  40                  45
Gln Gln Met Glu Glu Leu Gly Met Ala Pro Ala Leu Gln Pro Thr Gln
        50                  55                  60
Gly Ala Met Pro Ala Phe Ala Ser Ala Phe Gln Arg Arg Ala Gly Gly
65                  70                  75                  80
Val Leu Val Ala Ser His Leu Gln Ser Phe Leu Glu Val Ser Tyr Arg
                85                  90                  95
Val Leu Arg His Leu Ala Gln Pro Asp Met Ala Thr Pro Leu Gly Pro
                100                 105                 110
Ala Ser Ser Leu Pro Gln Ser Phe Leu Leu Lys Ser Leu Glu Gln Val
                115                 120                 125
Arg Lys Ile Gln Gly Asp Gly Ala Ala Leu Gln Glu Lys Leu Cys Ala
    130                 135                 140
Thr Tyr Lys Leu Cys His Pro Glu Glu Leu Val Leu Leu Gly His Ser
145                 150                 155                 160
Leu Gly Ile Pro Trp Ala Pro Leu Ser Ser Cys Pro Ser Gln Ala Leu
                165                 170                 175
Gln
```

(2) INFORMATION FOR SEQ ID NO:128:

(i) SEQUENCE CHARACTERISTICS:
  (A) LENGTH: 177 amino acids
  (B) TYPE: amino acid
  (C) STRANDEDNESS: unknown
  (D) TOPOLOGY: unknown (ii) MOLECULE TYPE: peptide (xi) SEQUENCE DESCRIPTION: SEQ ID NO:128:

```
His Leu Ala Gln Pro Asp Met Ala Thr Pro Leu Gly Pro Ala Ser Ser
1               5                   10                  15

Leu Pro Gln Ser Phe Leu Leu Lys Ser Leu Glu Gln Val Arg Lys Ile
            20                  25                  30

Gln Gly Asp Gly Ala Ala Leu Gln Glu Lys Leu Cys Ala Thr Tyr Lys
            35                  40                  45

Leu Cys His Pro Glu Glu Leu Val Leu Leu Gly His Ser Leu Gly Ile
        50                  55                  60

Pro Trp Ala Pro Leu Ser Ser Cys Pro Ser Gln Ala Leu Gln Leu Ala
65                  70                  75                  80

Gly Cys Leu Ser Gln Leu His Ser Gly Leu Phe Leu Tyr Gln Gly Leu
                85                  90                  95

Leu Gln Ala Leu Glu Gly Ile Ser Pro Glu Leu Gly Pro Thr Leu Asp
                100                 105                 110

Thr Leu Gln Leu Asp Val Ala Asp Phe Ala Thr Thr Ile Trp Gln Gln
            115                 120                 125

Met Glu Glu Leu Gly Met Ala Pro Ala Leu Gln Pro Thr Gln Gly Ala
        130                 135                 140

Met Pro Ala Phe Ala Ser Ala Phe Gln Arg Arg Ala Gly Gly Val Leu
145                 150                 155                 160

Val Ala Ser His Leu Gln Ser Phe Leu Glu Val Ser Tyr Arg Val Leu
                165                 170                 175

Arg
```

(2) INFORMATION FOR SEQ ID NO:129:

(i) SEQUENCE CHARACTERISTICS:
  (A) LENGTH: 531 base pairs
  (B) TYPE: nucleic acid
  (C) STRANDEDNESS: unknown
  (D) TOPOLOGY: unknown (ii) MOLECULE TYPE: other nucleic acid
  (A) DESCRIPTION: /desc = "synthetic"

(xi) SEQUENCE DESCRIPTION: SEQ ID NO:129:

```
CACCTTGCGC AGCCCGACAT GGCTACACCA TTAGGCCCTG CCAGCTCCCT GCCCCAGAGC      60

TTCCTGCTCA AGTCTTTAGA GCAAGTGAGG AAGATCCAGG GCGATGGCGC AGCGCTCCAG     120

GAGAAGCTGT GTGCCACCTA CAAGCTGTGC CACCCCGAGG AGCTGGTGCT GCTCGGACAC     180

TCTCTGGGCA TCCCCTGGGC TCCCCTGAGC TCCTGCCCCA GCCAGGCCCT GCAGCTGGCA     240

GGCTGCTTGA GCCAACTCCA TAGCGGCCTT TTCCTCTACC AGGGGCTCCT GCAGGCCCTG     300

GAAGGGATAT CCCCCGAGTT GGGTCCCACC TTGGACACAC TGCAGCTGGA CGTCGCCGAC     360

TTTGCCACCA CCATCTGGCA GCAGATGGAA GAACTGGGAA TGGCCCCTGC CCTGCAGCCC     420

ACCCAGGGTG CCATGCCGGC CTTCGCCTCT GCTTTCCAGC GCCGGGCAGG AGGGGTCCTG     480

GTTGCTAGCC ATCTGCAGAG CTTCCTGGAG GTGTCGTACC GCGTTCTACG C             531
```

G-CSF RECEPTOR AGONISTS

The present application is a divisional of application Ser. No. 08/833,167 filed on Apr. 4, 1997, now U.S. Pat. No. 6,100,070, which is a Continuation in Part of Ser. No. PCT/US96/15935, filed Oct. 4, 1996 and which claims priority under 35 U.S.C. §119(e) of U.S. provisional application Ser. No. 60/004,382 filed Sep. 27, 1995. The noted applications are incorporated herein by reference.

FIELD OF THE INVENTION

The present invention relates to human G-CSF receptor agonists with activity on hematopoietic cell differentiation and expansion.

BACKGROUND OF THE INVENTION

The human blood-forming (hematopoietic) system replaces a variety of white blood cells (including neutrophils, macrophages, and basophils/mast cells), red blood cells (erythrocytes) and clot-forming cells (megakaryocytes/platelets). The hematopoietic systems of the average male has been estimated to produce on the order of $4.5 \times 10^{11}$ granulocytes and erythrocytes every year, which is equivalent to an annual replacement of total body weight (Dexter et al., *BioEssays*, 2;154–158, 1985).

It is believed that small amounts of certain hematopoietic growth factors account for the differentiation of a small number of progenitor "stem cells" into the variety of blood cell lines, for the tremendous proliferation of those lines, and for the ultimate differentiation of mature blood cells from those lines. Because the hematopoietic growth factors are present in extremely small amounts, the detection and identification of these factors has relied upon an array of assays which as yet only distinguish among the different factors on the basis of stimulative effects on cultured cells under artificial conditions.

U.S. Pat. No. 4,999,291 discloses DNA and methods for making G-CSF the disclosure of which is incorporated herein by reference in it entirety.

U.S. Pat. No. 4,810,643 relates to DNA and methods of making G-CSF and Cys to Ser substitution variants of G-CSF.

Kuga et al. (*Biochem.+Biophys. Res. Comm.* 159:103–111, 1989) made a series of G-CSF variants to partially define the structure-function relationship. Kuga et al. found that internal and C-terminal deletions abolished activity, while N-terminal deletions of up to 11 amino acids and amino acid substitutions at positions 1, 2 and 3 were active.

Watanabe et al. (*Anal. Biochem.* 195:38–44, 1991) made a variant to study G-CSF receptor binding in which amino acids 1 and 3 were changed to Tyr for radioiodination of the protein. Watanabe et al. found this $Tyr^1$, $Tyr^3$ G-CSF variant to be active.

WO 95/27732 describes, but does not show that the molecule has biological activity, a circularly permuted G-CSF ligand with a breakpoint at positions 68/69 creating a circularly permuted G-CSF ligand with a new N-terminus at the original position 69 of G-CSF and a new C-terminus at the original position 68 of G-CSF. WO 95/27732 also discloses circularly permuted GM-CSF, IL-2 and IL-4.

Rearrangement of Protein Sequences

In evolution, rearrangements of DNA sequences serve an important role in generating a diversity of protein structure and function. Gene duplication and exon shuffling provide an important mechanism to rapidly generate diversity and thereby provide organisms with a competitive advantage, especially since the basal mutation rate is low (Doolittle, *Protein Science* 1:191–200, 1992).

The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., *Proc. Natl. Acad. Sci. U.S.A.* 76:3218–3222, 1979; Teather & Erfle, *J. Bacteriol.* 172: 3837–3841, 1990; Schimming et al., *Eur. J. Biochem.* 204: 13–19, 1992; Yamiuchi and Minamikawa, *FEBS Lett.* 260:127–130, 1991: MacGregor et al., *FEBS Lett.* 378:263–266, 1996). The first in vitro application of this type of rearrangement to proteins was described by Goldenberg and Creighton (*J. Mol. Biol.* 165:407–413, 1983). A new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus, and the new sequence continues with the same sequence as the original until it reaches a point that is at or near the amino acid that was N-terminal to the breakpoint site of the original sequence, this residue forming the new C-terminus of the chain.

This approach has been applied to proteins which range in size from 58 to 462 amino acids (Goldenberg & Creighton, *J. Mol. Biol.* 165:407–413, 1983; Li & Coffino, *Mol. Cell. Biol.* 13:2377–2383, 1993). The proteins examined have represented a broad range of structural classes, including proteins that contain predominantly α-helix (interleukin-4; Kreitman et al., *Cytokine* 7:311–318, 1995), β-sheet (interleukin-1; Horlick et al., *Protein Eng.* 5:427–431, 1992), or mixtures of the two (yeast phosphoribosyl anthranilate isomerase; Luger et al., *Science* 243:206–210, 1989). Broad categories of protein function are represented in these sequence reorganization studies:

| Enzymes | |
|---|---|
| T4 lysozyme | Zhang et al., Biochemistry 32:12311–12318 (1993); Zhang et al., Nature Struct. Biol. 1:434–438 (1995) |
| dihydrofolate reductase | Buchwalder et al., Biochemistry 31:1621–1630 (1994); Protasova et al., Prot. Eng. 7:1373–1377 (1995) |
| ribonuclease T1 | Mullins et al., J. Am. Chem. Soc. 116:5529–5533 (1994); Garrett et al., Protein Science 5:204–211 (1996) |
| Bacillus β-glucanse | Hahn et al., Proc. Natl. Acad. Sci. U.S.A. 91:10417–10421 (1994) |
| aspartate transcarbamoylase | Yang & Schachman, Proc. Natl. Acad. Sci. U.S.A. 90:11980–11984 (1993) |
| phosphoribosyl anthranilate isomerase | Luger et al., Science 243:206–210 (1989); Luger et al., Prot. Eng. 3:249–258 (1990) |
| pepsin/pepsinogen | Lin et al., Protein Science 4:159–166 (1995) |
| glyceraldehyde-3-phosphate dehydrogenase | Vignais et al., Protein Science 4:994–1000 (1995) |
| ornithine decarboxylase | Li & Coffino, Mol. Cell. Biol. 13:2377–2383 (1993) |
| yeast | Ritco-Vonsovici et al., Biochemistry |

| -continued | |
|---|---|
| phosphoglycerate dehydrogenase Enzyme Inhibitor | 34:16543–16551 (1995) |
| basic pancreatic trypsin inhibitor Cytokines | Goldenberg & Creighton, J. Mol. Biol. 165:407–413 (1983) |
| interleukin-1β | Horlick et al., Protein Eng. 5:427–431 (1992) |
| interleukin-4 Tyrosine Kinase Recognition Domain | Kreitman et al., Cytokine 7:311–318 (1995) |
| α-spectrin SH3 domain Transmembrane Protein | Viguera, et al., J. Mol. Biol. 247:670–681 (1995) |
| omp A Chimeric Protein | Koebnik & Krämer, J. Mol. Biol. 250:617–626 (1995) |
| interleukin-4-Pseudomonas exotoxin fusion molecule | Kreitman et al., Proc. Natl. Acad. Sci. U.S.A. 91:6889–6893 (1994). |

The results of these studies have been highly variable. In many cases substantially lower activity, solubility or thermodynamic stability were observed (E. coli dihydrofolate reductase, aspartate transcarbamoylase, phosphoribosyl anthranilate isomerase, glyceraldehyde-3-phosphate dehydrogenase, ornithine decarboxylase, omp A, yeast phosphoglycerate dehydrogenase). In other cases, the sequence rearranged protein appeared to have many nearly identical properties as its natural counterpart (basic pancreatic trying inhibitor, T4 lysozyme, ribonuclease T1, Bacillus-βglucanase, interleukin-1β α-spectrin SH3 domain, pepsinogen, interleukin-4). In exceptional cases, an unexpected improvement over some properties of the natural sequence was observed, e.g., the solubility and refolding rate for rearranged α-spectrin SH3 domain sequences, and the receptor affinity and anti-tumor activity of transposed interleukin-4-Pseudomonas exotoxin fusion molecule (Kreitman et al., Proc. Natl. Acad. Sci. U.S.A. 91:6889–6893, 1994; Kreitman et al., Cancer Res. 55:3357–3363, 1995).

The primary motivation for these types of studies has been to study the role of short-range and long-range interactions in protein folding and stability. Sequence rearrangements of this type convert a subset of interactions that are long-range in the original sequence into short-range interactions in the new sequence, and vice versa. The fact that many of these sequence rearrangements are able to attain a conformation with at least some activity is persuasive evidence that protein folding occurs by multiple folding pathways (Viguera, et al., J. Mol. Biol. 247:670–681, 1995). In the case of the SH3 domain of α-spectrin, choosing new termini at locations that corresponded to β-hairpin turns resulted in proteins with slightly less stability, but which were nevertheless able to fold.

The positions of the internal breakpoints used in the studies cited here are found exclusively on the surface of proteins, and are distributed throughout the linear sequence without any obvious bias towards the ends or the middle (the variation in the relative distance from the original N-terminus to the breakpoint is ca. 10 to 80% of the total sequence length). The linkers connecting the original N- and C-termini in these studies have ranged from 0 to 9 residues. In one case (Yang & Schachman, Proc. Natl. Acad. Sci. U.S.A. 90:11980–11984, 1993), a portion of sequence has been deleted from the original C-terminal segment, and the connection made from the truncated C-terminus to the original N-terminus. Flexible hydrophilic residues such as Gly and Ser are frequently used in the linkers. Viguera, et al.(J. Mol. Biol. 247:670–681, 1995) compared joining the original N- and C- termini with 3- or 4-residue linkers; the 3-residue linker was less thermodynamically stable. Protasova et al. (Protein Eng. 7:1373–1377, 1994) used 3- or 5-residue linkers in connecting the original N-termini of E. coli dihydrofolate reductase; only the 3-residue linker produced protein in good yield.

SUMMARY OF THE INVENTION

The modified human G-CSF receptor agonists of the present invention can be represented by the Formula:

$$X^1-(L)_a-X^2$$

wherein;

a is 0 or 1;

$X^1$ is a peptide comprising an amino acid sequence corresponding to the sequence of residues n+1 through J;

$X^2$ is a peptide comprising an amino acid sequence corresponding to the sequence of residues 1 through n;

n is an integer ranging from 1 to J-1; and

L is a linker.

In the formula above the constituent amino acids residues of human G-CSF are numbered sequentially 1 through J from the amino to the carboxyl terminus. A pair of adjacent amino acids within this protein may be numbered n and n+1 respectively where n is an integer ranging from 1 to J-1. The residue n+1 becomes the new N-terminus of the new G-CSF receptor agonist and the residue n becomes the new C-terminus of the new G-CSF receptor agonist.

The present invention relates to novel G-CSF receptor agonists of the following formula:

```
  1                             10              (SEQ ID NO:1)
Xaa Xaa Xaa Gly Pro Ala Ser Ser Leu Pro Gln Ser Xaa

20
Leu Leu Xaa Xaa Xaa Glu Gln Val Xaa Lys Xaa Gln Gly Xaa Gly 30                              40
Ala Xaa Leu Gln Glu Xaa Leu Xaa Ala Thr Tyr Lys Leu Xaa Xaa

50
Xaa Glu Xaa Xaa Val Xaa Xaa Gly His Ser Xaa Gly Ile Pro Trp
```

-continued

```
    60                                      70
Ala Pro Leu Ser Ser Xaa Pro Ser Xaa Ala Leu Xaa Leu Ala Gly

80
Xaa Leu Ser Gln Leu His Ser Gly Leu Phe Leu Tyr Gln Gly Leu 90                                      100
Leu Gln Ala Leu Glu Gly Ile Ser Pro Glu Leu Gly Pro Thr Leu

110
Xaa Thr Leu Gln Xaa Asp Val Ala Asp Phe Ala Xaa Thr Ile Trp 120                                     130
Gln Gln Met Glu Xaa Xaa Gly Met Ala Pro Ala Leu Gln Pro Thr

140
Gln Gly Ala Met Pro Ala Phe Ala Ser Ala Xaa Gln Xaa Xaa Ala 150                                     160
Gly Gly Val Leu Val Ala Ser Xaa Leu Gln Xaa Phe Leu Xaa Xaa

170
Ser Tyr Arg Val Leu Xaa Xaa Leu Ala Gln Pro
``` wherein
Xaa at position 1 is Thr, Ser, Arg, Tyr or Gly;
Xaa at position 2 is Pro or Leu;
Xaa at position 3 is Leu, Arg, Tyr or Ser;
Xaa at position 13 is Phe, Ser, His, Thr or Pro;
Xaa at position 16 is Lys, Pro, Ser, Thr or His;
Xaa at position 17 is Cys, Ser, Gly, Ala, Ile, Tyr or Arg;
Xaa at position 18 is Leu, Thr, Pro, His, Ile or Cys;
Xaa at position 22 is Arg, Tyr, Ser, Thr or Ala;
Xaa at position 24 is Ile, Pro, Tyr or Leu;
Xaa at position 27 is Asp, or Gly;
Xaa at position 30 is Ala, Ile, Leu or Gly;
Xaa at position 34 is Lys or Ser;
Xaa at position 36 is Cys or Ser;
Xaa at position 42 is Cys or Ser;
Xaa at position 43 is His, Thr, Gly, Val, Lys, Trp, Ala, Arg, Cys, or Leu;
Xaa at position 44 is Pro, Gly, Arg, Asp, Val, Ala, His, Trp, Gln, or Thr;
Xaa at position 46 is Glu, Arg, Phe, Arg, Ile or Ala;
Xaa at position 47 is Leu or Thr;
Xaa at position 49 is Leu, Phe, Arg or Ser;
Xaa at position 50 is Leu, Ile, His, Pro or Tyr;
Xaa at position 54 is Leu or His;
Xaa at position 64 is Cys or Ser;
Xaa at position 67 is Gln, Lys, Leu or Cys;
Xaa at position 70 is Gln, Pro, Leu, Arg or Ser;
Xaa at position 74 is Cys or Ser;
Xaa at position 104 is Asp, Gly or Val;
Xaa at position 108 is Leu, Ala, Val, Arg, Trp, Gln or Gly;
Xaa at position 115 is Thr, His, Leu or Ala;
Xaa at position 120 is Gln, Gly, Arg, Lys or His
Xaa at position 123 is Glu, Arg, Phe or Thr
Xaa at position 144 is Phe, His, Arg, Pro, Leu, Gln or Glu;
Xaa at position 146 is Arg or Gln;
Xaa at position 147 is Arg or Gln;
Xaa at position 156 is His, Gly or Ser.
Xaa at position 159 is Ser, Arg, Thr, Tyr, Val or Gly;
Xaa at position 162 is Glu, Leu, Gly or Trp;
Xaa at position 163 is Val, Gly, Arg or Ala;
Xaa at position 169 is Arg, Ser, Leu, Arg or Cys;
Xaa at position 170 is His, Arg or Ser;

wherein optionally 1–11 amino acids from the N-terminus and 1–5 from the C-terminus can be deleted; and wherein the N-terminus is joined to the C-terminus directly or through a linker capable of joining the N-terminus to the C-terminus and having new C- and N-termini at amino acids;

| | | |
|---|---|---|
| 38–39 | 62–63 | 123–124 |
| 39–40 | 63–64 | 124–125 |
| 40–41 | 64–65 | 125–126 |
| 41–42 | 65–66 | 126–127 |
| 42–43 | 66–67 | 127–128 |
| 43–44 | 67–68 | 128–129 |
| 45–46 | 68–69 | 129–130 |
| 48–49 | 69–70 | 130–131 |
| 49–50 | 70–71 | 131–132 |
| 52–53 | 71–72 | 132–133 |
| 53–54 | 91–92 | 133–134 |
| 54–55 | 92–93 | 134–135 |
| 55–56 | 93–94 | 135–136 |
| 56–57 | 94–95 | 136–137 |
| 57–58 | 95–96 | 137–138 |
| 58–59 | 96–97 | 138–139 |
| 59–60 | 97–98 | 139–140 |
| 60–61 | 98–99 | 140–141 |
| 61–62 | 99–100 | 141–142 |
| | | or 142–143. |

The G-CSF receptor agonists of the present invention may contain amino acid substitutions, deletions and/or insertions and may also have amino acid deletions at either/or both the N- and C- termini.

The more preferred breakpoints at which new C-terminus and N-terminus can be made are; 38-39, 39-40, 40-41, 41-42, 48-49, 53-54, 54-55, 55-56, 56-57, 57-58, 58-59, 59-60, 60-61, 61-62, 62-63, 64-65, 65-66, 66-67, 67-68, 68-69, 69-70, 96-97, 125-126, 126-127, 127-128, 128-129, 129-130, 130-131, 131-132, 132-133, 133-134, 134-135, 135-136, 136-137, 137-138, 138-139, 139-140, 140-141 and 141-142.

The most preferred breakpoints at which new C-terminus and N-terminus can be made are; 38-39, 48-49, 96-97, 125-126, 132-133 and 141-142.

A preferred embodiment of the present invention the linker (L) joining the N-terminus to the C-terminus is a polypeptide selected from the group consisting of:

GlyGlyGlySer (SEQ ID NO:2);

GlyGlyGlySerGlyGlyGlySer (SEQ ID NO:61);

GlyGlyGlySerGlyGlyGlySerGlyGlyGlySer (SEQ ID NO:62);

SerGlyGlySerGlyGlySer (SEQ ID NO:63);
GluPheGlyAsnMet (SEQ ID NO:64);
GluPheGlyGlyAsnMet (SEQ ID NO:65);
GluPheGlyGlyAsnGlyGlyAsnMet (SEQ ID NO:66); and
GlyGlySerAspMetAlaGly (SEQ ID NO:67).

The present invention also includes a human G-CSF receptor agonist polypeptide, comprising a modified G-CSF amino acid sequence of the Formula:

```
1                            10                     (SEQ ID NO:1)
Xaa Xaa Xaa Gly Pro Ala Ser Ser Leu Pro Gln Ser Xaa

20
Leu Leu Xaa Xaa Xaa Glu Gln Val Xaa Lys Xaa Gln Gly Xaa Gly 30                          40
Ala Xaa Leu Gln Glu Xaa Leu Xaa Ala Thr Tyr Lys Leu Xaa Xaa

50
Xaa Glu Xaa Xaa Val Xaa Xaa Gly His Ser Xaa Gly Ile Pro Trp 60                              70
Ala Pro Leu Ser Ser Xaa Pro Ser Xaa Ala Leu Xaa Leu Ala Gly

80
Xaa Leu Ser Gln Leu His Ser Gly Leu Phe Leu Tyr Gln Gly Leu 90                              100
Leu Gln Ala Leu Glu Gly Ile Ser Pro Glu Leu Gly Pro Thr Leu

110
Xaa Thr Leu Gln Xaa Asp Val Ala Asp Phe Ala Xaa Thr Ile Trp 120                             130
Gln Gln Met Glu Xaa Xaa Gly Met Ala Pro Ala Leu Gln Pro Thr

140
Gln Gly Ala Met Pro Ala Phe Ala Ser Ala Xaa Gln Xaa Xaa Ala 150                             160
Gly Gly Val Leu Val Ala Ser Xaa Leu Gln Xaa Phe Leu Xaa Xaa

170
Ser Tyr Arg Val Leu Xaa Xaa Leu Ala Gln Pro
``` wherein
Xaa at position 1 is Thr, Ser, Arg, Tyr or Gly;
Xaa at position 2 is Pro or Leu;
Xaa at position 3 is Leu, Arg, Tyr or Ser;
Xaa at position 13 is Phe, Ser, His, Thr or Pro;
Xaa at position 16 is Lys, Pro, Ser, Thr or His;
Xaa at position 17 is Cys, Ser, Gly, Ala, Ile, Tyr or Arg;
Xaa at position 18 is Leu, Thr, Pro, His, Ile or Cys;
Xaa at position 22 is Arg, Tyr, Ser, Thr or Ala;
Xaa at position 24 is Ile, Pro, Tyr or Leu;
Xaa at position 27 is Asp, or Gly;
Xaa at position 30 is Ala, Ile, Leu or Gly;
Xaa at position 34 is Lys or Ser;
Xaa at position 36 is Cys or Ser;
Xaa at position 42 is Cys or Ser;
Xaa at position 43 is His, Thr, Gly, Val, Lys, Trp, Ala, Arg, Cys, or Leu;
Xaa at position 44 is Pro, Gly, Arg, Asp, Val, Ala, His, Trp, Gln, or Thr;
Xaa at position 46 is Glu, Arg, Phe, Arg, Ile or Ala;
Xaa at position 47 is Leu or Thr;
Xaa at position 49 is Leu, Phe, Arg or Ser;
Xaa at position 50 is Leu, Ile, His, Pro or Tyr;
Xaa at position 54 is Leu or His;
Xaa at position 64 is Cys or Ser;
Xaa at position 67 is Gln, Lys, Leu or Cys;
Xaa at position 70 is Gln, Pro, Leu, Arg or Ser;
Xaa at position 74 is Cys or Ser;
Xaa at position 104 is Asp, Gly or Val;
Xaa at position 108 is Leu, Ala, Val, Arg, Trp, Gln or Gly;
Xaa at position 115 is Thr, His, Leu or Ala;
Xaa at position 120 is Gln, Gly, Arg, Lys or His
Xaa at position 123 is Glu, Arg, Phe or Thr
Xaa at position 144 is Phe, His, Arg, Pro, Leu, Gln or Glu;
Xaa at position 146 is Arg or Gln;
Xaa at position 147 is Arg or Gln;
Xaa at position 156 is His, Gly or Ser;
Xaa at position 159 is Ser, Arg, Thr, Tyr, Val or Gly;
Xaa at position 162 is Glu, Leu, Gly or Trp;
Xaa at position 163 is Val, Gly, Arg or Ala;
Xaa at position 169 is Arg, Ser, Leu, Arg or Cys;
Xaa at position 170 is His, Arg or Ser;
wherein optionally 1–11 amino acids from the N-terminus and 1–5 from the C-terminus can be deleted;
wherein the N-terminus is joined to the C-terminus directly or through a linker capable of joining the N-terminus to the C-terminus and having new C- and N-terminus at amino acids;.
2–3
10–11
12–13
18–19
122–123
158–159
169–170.

The present invention also encompasses recombinant human G-CSF receptor agonists co-administered or sequentially with one or more additional colony stimulating factors (CSF) including, cytokines, lymphokines, interleukins, hematopoietic growth factors which include but are not limited to GM-CSF, c-mpl ligand (also known as TPO or MGDF), M-CSF, erythropoietin (EPO), IL-1, IL-4, IL-2, IL-3, IL-5, IL 6, IL-7, IL-8, IL-9, IL-10, IL-11, IL-12, IL-13, IL-15, LIF, flt3/flk2 ligand, human growth hormone, B-cell growth factor, B-cell differentiation factor, eosinophil differentiation factor and stem cell factor (SCF) also known as steel factor or c-kit ligand (herein collectively referred to as "colony stimulating factors" or "CSF"). These co-administered mixtures may be characterized by having the usual activity of both of the peptides or the mixture may be further characterized by having a biological or physiological activity greater than simply the additive function of the presence of the G-CSF receptor agonists or the second colony stimulating factor alone. The co-administration may also provide an enhanced effect on the activity or an activity different from that expected by the presence of the G-CSF ligand or the second colony stimulating factor. The co-administration may also have an improved activity profile which may include reduction of undesirable biological activities associated with native human G-CSF. In addition to the list above, IL-3 variants taught in WO 94/12639 and WO 94/12638 can be co-administered with the polypeptides of the present invention.

In addition, it is envisioned that in vitro uses would include the ability to stimulate bone marrow and blood cell activation and growth before the expanded cells are infused into patients.

DETAILED DESCRIPTION OF THE INVENTION

Figure 1:
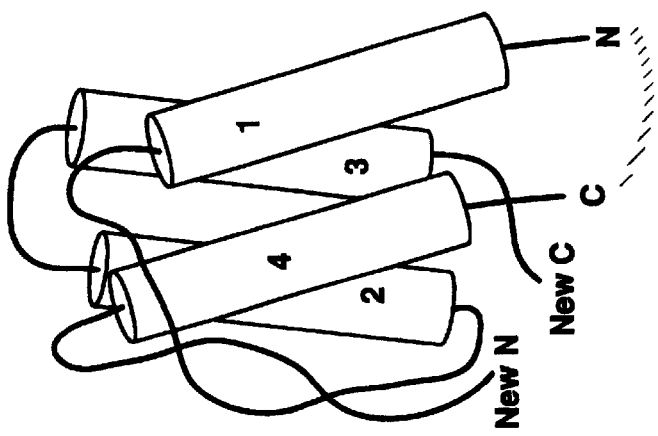
FIG. 1 schematically illustrates the sequence rearrangement of a protein. The N-terminus (N) and the C-terminus (C) of the native protein are joined through a linker, or joined directly. The protein is opened at a breakpoint creating a new N-terminus (new N) and a new C-terminus (new-C) resulting in a protein with a new linear amino acid sequence. A rearranged molecule may be synthesized de novo as linear molecule and not go through the steps of joining the original N-terminus and the C-terminus and opening of the protein at the breakpoint.
Figure 1:
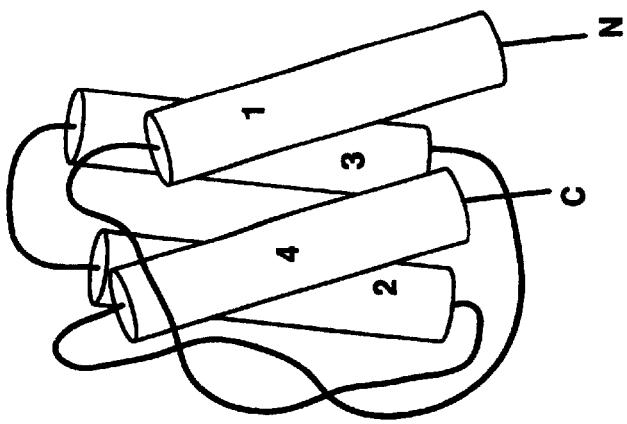

Receptor agonists of the present invention may be useful in the treatment of diseases characterized by decreased levels of granulocytes of the hematopoietic system.

A G-CSF receptor agonist may be useful in the treatment or prevention of neutropenia. Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anti-convulsants such as phenytoin or carbamazepine, anti-thyroids such as propylthiouracil and methimazole and diuretics. G-CSF receptor agonists may be useful in preventing or treating the bone marrow suppression or hematopoietic deficiencies which often occur in patients treated with these drugs.

Hematopoietic deficiencies may also occur as a result of viral, microbial or parasitic infections and as a result of treatment for renal disease or renal failure, e.g., dialysis. The present peptide may be useful in treating such hematopoietic deficiency.

Another aspect of the present invention provides plasmid DNA vectors for use in the method of expression of these novel G-CSF receptor agonists. These vectors contain the novel DNA sequences described above which code for the novel polypeptides of the invention. Appropriate vectors which can transform host cells capable of expressing the G-CSF receptor agonists include expression vectors comprising nucleotide sequences coding for the G-CSF receptor agonists joined to transcriptional and translational regulatory sequences which are selected according to the host cells used. Vectors incorporating modified sequences as described above are included in the present invention and are useful in the production of the modified G-CSF receptor agonist polypeptides. The vector employed in the method also contains selected regulatory sequences in operative association with the DNA coding sequences of the invention and capable of directing the replication and expression thereof in selected host cells.

As another aspect of the present invention, there is provided a novel method for producing the novel family of human G-CSF receptor agonists. The method of the present invention involves culturing suitable cells or cell line, which has been transformed with a vector containing a DNA sequence coding for expression of the novel G-CSF receptor agonist polypeptide. Suitable cells or cell lines may include various strains of bacteria such as *E. coli,* yeast, mammalian cells, or insect cells may be utilized as host cells in the method of the present invention.

Other aspects of the present invention are methods and therapeutic compositions for treating the conditions referred to above. Such compositions comprise a therapeutically effective amount of one or more of the G-CSF receptor agonists of the present invention in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 0.5–150 µg/kg of non-glycosylated G-CSF receptor agonists protein per kilogram of body weight. Dosages would be adjusted relative to the activity of a given receptor agonist and it would not be unreasonable to note that dosage regimens may include doses as low as 0.1 microgram and as high as 1 milligram per kilogram of body weight per day. In addition, there may exist specific circumstances where dosages of G-CSF receptor agonist would be adjusted higher or lower than the range of 0.5–150 micrograms per kilogram of body weight. These include co-administration with other CSF or growth factors; co-administration with chemotherapeutic drugs and/or radiation; the use of glycosylated G-CSF receptor agonists; and various patient-related issues mentioned earlier in this section. As indicated above, the therapeutic method and compositions may also include co-administration with other human factors. A non-exclusive list of other appropriate hematopoietins, CSFs and interleukins for simultaneous or serial co-administration with the polypeptides of the present invention includes GM-CSF, c-mpl ligand (also known as TPO or MGDF), M-CSF, erythropoietin (EPO), IL-1, IL-4, IL-2, IL-3, IL-5, IL 6, IL-7, IL-8, IL-9, IL-10, IL-11, IL-12, IL-13, IL-15, LIF, flt3/flk2 ligand, human growth hormone, B-cell growth factor, B-cell differentiation factor, eosinophil differentiation factor and stem cell factor (SCF) also known as steel factor or c-kit ligand (herein collectively referred to as "colony stimulating factors"), or combinations thereof. In addition to the list above, IL-3 variants taught in WO 94/12639 and WO 94/12638 can be co-administered with the polypeptides of the present invention.

The G-CSF receptor agonists of the present invention may be useful in the mobilization of hematopoietic progenitors and stem cells in peripheral blood. Peripheral blood derived progenitors have been shown to be effective in reconstituting patients in the setting of autologous marrow transplantation. Hematopoietic growth factors, including G-CSF and GM-CSF, have been shown to enhance the number of circulating progenitors and stem cells in the peripheral blood. This has simplified the procedure for peripheral stem cell collection and dramatically decreased the cost of the procedure by decreasing the number of pheresis required. The G-CSF receptor agonist of the present invention may be useful in mobilization of stem cells and further enhance the efficacy of peripheral stem cell transplantation.

The G-CSF receptor agonists of the present invention may also be useful in the ex vivo expansion of hematopoietic progenitors. Colony stimulating factors (CSFs), such as G-CSF, have been administered alone, co-administered with other CSFs, or in combination with bone marrow transplants subsequent to high dose chemotherapy to treat the neutropenia and which is often the result of such treatment. However the period of severe neutropenia may not be totally eliminated. The myeloid lineage, which is comprised of monocytes (macrophages), granulocytes (including neutrophils) and megakaryocytes, is critical in preventing infections and bleeding which can be life-threatening. Neutropenia may also be the result of disease, genetic disorders, drugs, toxins, radiation and many therapeutic treatments such as conventional oncology therapy.

Bone marrow transplants have been used to treat this patient population. However, several problems are associated with the use of bone marrow to reconstitute a compromised hematopoietic system including: 1) the number of stem cells in bone marrow or other tissues, such as spleen or peripheral blood, is limited, 2) Graft Versus Host Disease, 3) graft rejection and 4) possible contamination with tumor cells. Stem cells and progenitor cells make up a very small percentage of the nucleated cells in the bone marrow, spleen and peripheral blood. It is clear that a dose response exists such that a greater number of multipotential hematopoietic progenitors will enhance hematopoietic recovery. Therefore, the in vitro expansion of stem cells should enhance hematopoietic recovery and patient survival. Bone marrow from an allogeneic donor has been used to provide bone marrow for transplant. However, Graft Versus Host Disease and graft rejection limit bone marrow transplantation even in recipients with HLA-matched sibling donors. An alternative to allogeneic bone marrow transplants is autologous bone marrow transplants. In autologous bone marrow transplants, some of the patient's own marrow is harvested prior to myeloablative therapy, e.g. high dose chemotherapy, and is transplanted back into the patient afterwards. Autologous transplants eliminate the risk of Graft Versus Host Disease and graft rejection. However, autologous bone marrow transplants still present problems in terms of the limited number of stems cells in the marrow and possible contamination with tumor cells. The limited number of multipotential hematopoietic progenitors may be overcome by ex-vivo expansion of the multipotential hematopoietic progenitors. In addition, stem cells can be specifically isolated based on the presence of specific surface antigens such as CD34+ in order to decrease tumor cell contamination of the marrow graft.

The following patents contain further details on separating stem cells, CD34+ cells, culturing the cells with hematopoietic factors, the use of the cells for the treatment of patients with hematopoietic disorders and the use of hematopoietic factors for cell expansion and gene therapy.

U.S. Pat. No. 5,061,620 relates to compositions comprising human hematopoietic stem cells provided by separating the stem cells from dedicated cells.

U.S. Pat. No. 5,199,942 describes a method for autologous hematopoietic cell transplantation comprising: (1) obtaining hematopoietic progenitor cells from a patient; (2) ex-vivo expansion of cells with a growth factor selected from the group consisting of IL-3, flt3 ligand, c-kit ligand, GM CSF, IL-1, GM-CSF/IL-3 fusion protein and combinations thereof; (3) administering cellular preparation to a patient.

U.S. Pat. No. 5,240,856 relates to a cell separator that includes an apparatus for automatically controlling the cell separation process.

WO 91/16116 describes devices and methods for selectively isolating and separating target cells from a mixture of cells.

WO 91/18972 describes methods for in vitro culturing of bone marrow, by incubating suspension of bone marrow cells, using a hollow fiber bioreactor.

WO 92/18615 relates to a process for maintaining and expanding bone marrow cells, in a culture medium containing specific mixtures of cytokines, for use in transplants.

WO 93/08268 describes a method for selectively expanding stem cells, comprising the steps of (a) separating CD34+ stem cells from other cells and (b) incubating the separated cells in a selective medium, such that the stem cells are selectively expanded.

WO 93/18136 describes a process for in vitro support of mammalian cells derived from peripheral blood.

WO 93/18648 relates to a composition comprising human neutrophil precursor cells with a high content of myeloblasts and promyelocytes for treating genetic or acquired neutropenia.

WO 94/08039 describes a method of enrichment for human hematopoietic stem cells by selection for cells which express c-kit protein.

WO 94/11493 describes a stem cell population that are CD34+ and small in size, which are isolated using a counterflow elutriation method.

WO 94/27698 relates to a method combining immunoaffinity separation and continuous flow centrifugal separation for the selective separation of a nucleated heterogeneous cell population from a heterogeneous cell mixture.

WO 94/25848 describes a cell separation apparatus for collection and manipulation of target cells.

The long term culturing of highly enriched CD34+ precursors of hematopoietic progenitor cells from human bone marrow in cultures containing IL-1α, IL-3, IL-6 or GM-CSF is discussed in Brandt et al (*J. Clin. Invest.* 86:932–941, 1990).

One aspect of the present invention provides a method for selective ex-vivo expansion of stem cells. The term "stem cell" refers to the multipotential hematopoietic cells as well as early myeloid progenitor and precursors cells which can be isolated from bone marrow, spleen or peripheral blood. The term "expansion" refers to the proliferation and differentiation of the cells. The present invention provides a method for selective ex-vivo expansion of stem cells, comprising the steps of; (a) separating stem cells from other cells, (b) culturing the separated stem cells with a selective medium which contains a G-CSF receptor agonist and optionally a second colony stimulating factor, and (c) harvesting the cultured stems cells. Stem cells, as well as committed progenitor cells destined to become neutrophils, erythrocytes, platelets, etc., may be distinguished from most other cells by the presence or absence of particular progenitor marker antigens, such as CD34, that are present on the surface of these cells and/or by morphological characteristics. The phenotype for a highly enriched human stem cell fraction is reported as CD34+, Thy-1+ and lin-, but it is to be understood that the present invention is not limited to the expansion of this stem cell population. The CD34+ enriched human stem cell fraction can be separated by a number of reported methods, including affinity columns or beads, magnetic beads or flow cytometry using antibodies directed to surface antigens such as the CD34+. Further, physical separation methods such as counterflow elutriation may be used to enrich hematopoietic progenitors. The CD34+ progenitors are heterogeneous, and may be divided into several subpopulations characterized by the presence or absence of co-expression of different lineage associated cell surface associated molecules. The most immature progenitor cells do not express any known lineage associated markers, such as HLA-DR or CD38, but they may express CD90(thy-1). Other surface antigens such as CD33, CD38, CD41, CD71, HLA-DR or c-kit can also be used to selectively isolate hematopoietic progenitors. The separated cells can be incubated in selected medium in a culture flask, sterile bag or in hollow fibers. Various colony stimulating factors may be utilized in order to selectively expand cells. Representative factors that have been utilized for ex-vivo expansion of bone marrow include, c-kit ligand, IL-3, G-CSF, GM-CSF, IL-1, IL-6, IL-11, flt-3 ligand or combinations thereof. The proliferation of the stem cells can be monitored by enumerating the number of stem cells and other cells, by standard techniques (e.g. hemacytometer, CFU, LTCIC) or by flow cytometry prior and subsequent to incubation.

Several methods for ex-vivo expansion of stem cells have been reported utilizing a number of selection methods and expansion using various colony stimulating factors including c-kit ligand (Brandt et al., *Blood* 83:1507–1514, 1994; McKenna et al., *Blood* 86:3413–3420, 1995), IL-3 (Brandt et al., *Blood* 83:1507–1514, 1994; Sato et al., *Blood* 82:3600–3609, 1993), G-CSF (Sato et al., *Blood* 82:3600–3609, 1993), GM-CSF (Sato et al., *Blood* 82:3600–3609, 1993), IL-1 (Muench et al., *Blood* 81:3463–3473, 1993), IL-6 (Sato et al., *Blood* 82:3600–3609, 1993), IL-11 (Lemoli et al., *Exp. Hem.* 21:1668–1672, 1993; Sato et al., *Blood* 82:3600–3609, 1993), flt-3 ligand (McKenna et al., *Blood* 86:3413 3420, 1995) and/or combinations thereof (Brandt et al., *Blood* 83:1507 1514, 1994; Haylock et al., *Blood* 80:1405–1412, 1992, Koller et al., *Biotechnology* 11:358–363, 1993; Lemoli et al., *Exp. Hem.* 21:1668–1672, 1993), McKenna et al., *Blood* 86:3413–3420, 1995; Muench et al., *Blood* 81:3463–3473, 1993; Patchen et al., *Biotherapy* 7:13–26, 1994; Sato et al., *Blood* 82:3600–3609, 1993; Smith et al., *Exp. Hem.* 21:870–877, 1993; Steen et al., *Stem Cells* 12:214–224, 1994; Tsujino et al., *Exp. Hem.* 21:1379–1386, 1993). Among the individual colony stimulating factors, hIL-3 has been shown to be one of the most potent in expanding peripheral blood CD34+ cells (Sato et al., *Blood* 82:3600–3609, 1993; Kobayashi et al., *Blood* 73:1836–1841, 1989). However, no single factor has been shown to be as effective as the combination of multiple factors. The present invention provides methods for ex vivo expansion that utilize novel G-CSF receptor agonists.

Another aspect of the invention provides methods of sustaining and/or expanding hematopoietic precursor cells which includes inoculating the cells into a culture vessel which contains a culture medium that has been conditioned by exposure to a stromal cell line such as HS-5 (WO 96/02662, Roecklein and Torok-Strob, *Blood* 85:997–1105, 1995) that has been supplemented with a G-CSF receptor agonist of the present invention.

Another projected clinical use of growth factors has been in the in vitro activation of hematopoietic progenitors and stem cells for gene therapy. Due to the long life-span of hematopoietic progenitor cells and the distribution of their daughter cells throughout the entire body, hematopoietic progenitor cells are good candidates for ex vivo gene transfection. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy. Potential applications of gene therapy (review Crystal, *Science* 270:404–410, 1995) include; 1) the treatment of many congenital metabolic disorders and immunodeficiencies (Kay and Woo, *Trends Genet.* 10:253–257, 1994), 2) neurological disorders (Friedmann, *Trends Genet.* 10:210–214, 1994), 3) cancer (Culver and Blaese, *Trends Genet.* 10:174–178, 1994) and 4) infectious diseases (Gilboa and Smith, *Trends Genet.* 10:139–144, 1994).

There are a variety of methods, known to those with skill in the art, for introducing genetic material into a host cell. A number of vectors, both viral and non-viral have been developed for transferring therapeutic genes into primary cells. Viral based vectors include; 1) replication deficient recombinant retrovirus (Boris-Lawrie and Temin, *Curr. Opin. Genet. Dev.* 3:102–109, 1993; Boris-Lawrie and Temin, *Annal. New York Acad. Sci.* 716:59–71, 1994; Miller, *Current Top. Microbiol. Immunol.* 158:1–24, 1992) and replication-deficient recombinant adenovirus (Berkner, *Bio-*

Techniques 6:616–629, 1988; Berkner, *Current Top. Microbiol. Immunol.* 158:39–66, 1992; Brody and Crystal, *Annal. New York Acad. Sci.* 716:90–103, 1994). Non-viral based vectors include protein/DNA complexes (Cristiano et al., *PNAS USA.* 90:2122–2126, 1993; Curiel et al., *PNAS USA* 88:8850–8854, 1991; Curiel, *Annal. New York Acad. Sci.* 716:36–58, 1994), electroporation and liposome mediated delivery such as cationic liposomes (Farhood et al., *Annal. New York Acad. Sci.* 716:23–35, 1994).

The present invention provides an improvement to the existing methods of expanding hematopoietic cells, into which new genetic material has been introduced, in that it provides methods utilizing G-CSF receptor agonists that may have improved biological activity and/or physical properties.

Determination of the Linker

The length of the amino acid sequence of the linker can be selected empirically or with guidance from structural information, or by using a combination of the two approaches.

When no structural information is available, a small series of linkers can be prepared for testing using a design whose length is varied in order to span a range from 0 to 50 Å and whose sequence is chosen in order to be consistent with surface exposure (hydrophilicity, Hopp & Woods, *Mol. Immunol.* 20: 483–489, 1983; Kyte & Doolittle, *J. Mol. Biol.* 157:105–132, 1982; solvent exposed surface area, Lee & Richards, *J. Mol. Biol.* 55:379–400, 1971) and the ability to adopt the necessary conformation without deranging the configuration of the c-mpl receptor agonist (conformationally flexible; Karplus & Schulz, *Naturwissenschaften* 72:212–213, (1985). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser (SEQ ID NO:2) repeated n times, where n is 1, 2, 3 or 4. Those skilled in the art will recognize that there are many such sequences that vary in length or composition that can serve as linkers with the primary consideration being that they be neither excessively long nor short (cf., Sandhu, *Critical Rev. Biotech.* 12: 437–462, 1992); if they are too long, entropy effects will likely destabilize the three-dimensional fold, and may also make folding kinetically impractical, and if they are too short, they will likely destabilize the molecule because of torsional or steric strain.

Those skilled in the analysis of protein structural information will recognize that using the distance between the chain ends, defined as the distance between the c-alpha carbons, can be used to define the length of the sequence to be used, or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser (SEQ ID NO:2) cassette approach mentioned above; or optionally a combination of the original sequence and new sequence having the appropriate total length may be used.

Determination of the Amino and Carboxyl Termini of G-CSF Receptor Agonists

Sequences of G-CSF receptor agonists capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence.

It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein crystals or nuclear magnetic resonance spectroscopy of protein solutions. Examples of structural information that are relevant to the identification of breakpoint regions include the location and type of protein secondary structure (alpha and 3–10 helices, parallel and anti-parallel beta sheets, chain reversals and turns, and loops; Kabsch & Sander, *Biopolymers* 22: 2577–2637, 1983; the degree of solvent exposure of amino acid residues, the extent and type of interactions of residues with one another (Chothia, *Ann. Rev. Biochem.* 53:537–572; 1984) and the static and dynamic distribution of conformations along the polypeptide chain (Alber & Mathews, *Methods Enzymol.* 154: 511–533, 1987). In some cases additional information is known about solvent exposure of residues; one example is a site of post-translational attachment of carbohydrate which is necessarily on the surface of the protein. When experimental structural information is not available, or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile & Salvatore, *Eur. J. Biochem.* 218:603–621, 1993) Thus using either the experimentally derived structural information or predictive methods (e.g., Srinivisan & Rose *Proteins: Struct., Funct. & Genetics,* 22: 81–99, 1995) the parental amino acid sequence is inspected to classify regions according to whether or not they are integral to the maintenance of secondary and tertiary structure. The occurrence of sequences within regions that are known to be involved in periodic secondary structure (alpha and 3–10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region.

TABLE 1

| | OLIGONUCLEOTIDES |
|---|---|
| L-11start.seq | GCTCTGAGAG CCGCCAGAGC CGCCAGAGGG CTGCGCAAGG TGGCGTAGAA CGCG (SEQ ID NO: 3) |
| L-11stop.seq | CAGCCCTCTG GCGGCTCTGG CGGCTCTCAG AGCTTCCTGC TCAAGTCTTT AGAG (SEQ ID NO: 4) |
| BlstartP.seq | GGGCTGCGCA AGGTGGCG (SEQ ID NO: 5) |
| blstopP.seq | ACACCATTGG GCCCTGCCAG C (SEQ ID NO: 6) |
| 39start.seq | GATCGACCAT GGCTTACAAG CTGTGCCACC CC (SEQ ID NO: 7) |
| 38stop.Seq | CGATCGAAGC TTATTAGGTG GCACACAGCT TCTCCT (SEQ ID NO: 8) |
| 97start.seq | GATCGACCAT GGCTCCCGAG TTGGGTCCCA CC (SEQ ID NO: 9) |
| 96stop.Seq | CGATCGAAGC TTATTAGGAT ATCCCTTCCA GGGCCT (SEQ ID NO: 10) |
| 126start.seq | GATCGACCAT GGCTATGGCC CCTGCCCTGC AG (SEQ ID NO: 11) |
| 125stop.Seq | CGATCGAAGC TTATTATCCC AGTTCTTCCA TCTGCT (SEQ ID NO: 12) |
| 133start.seq | GATCGACCAT GGCTACCCAG GGTGCCATGC CG (SEQ ID NO: 13) |
| 132stop.seq | CGATCGAAGC TTATTAGGGC TGCAGGGCAG GGGCCA (SEQ ID NO: 14) |
| 142start.seq | GATCGACCAT GGCTTCTGCT TTCCAGCGCC GG (SEQ ID NO: 15) |
| 141stop.Seq | CGATCGAAGC TTATTAGGCG AAGGCCGGCA TGGCAC (SEQ ID NO: 16) |
| 96for.Seq | ATATCCATGG CTCCGGAACT GGGTCCAACT CTG (SEQ ID NO: 17) |
| 96rev.Seq | ACCTCCAGGA AGCTCTGCAG ATGG (SEQ ID NO: 18) |
| 125for.seq | TATATCCATG GCTATGGCTC CAGCTCTGCA ACCAACTCAA GGTGCAATGC CAGCATTTGC ATCTG (SEQ ID NO: 19) |
| 125rev.seq | GATGGCTAGC AACCAGAACA CCACCTGCAC GACGTTGAAA AGCAGATGCA AATGCTGGCA TTG (SEQ ID NO: 20) |
| 132for.seq | TATATCCATG GCTACTCAAG GTGCTATGCC AGCTTTTGCT TCTGCTTTTC AACGTCG (SEQ ID NO: 21) |

TABLE 1-continued

| | OLIGONUCLEOTIDES |
|---|---|
| 132rev.seq | GCAGATGGCT AGCAACCAGA ACACCACCTG CACGACGTTG AAAAGCAGAA GCAAAAGC (SEQ ID NO: 22) |
| 141for.seq | CATGGCTTCT GCTTTTCAAC GTCGTGCAGG TGGTGTTCTG GTTG (SEQ ID NO: 23) |
| 141rev.seq | CTAGCAACCA GAACACCACC TGCACGACGT TGAAAAGCAG AAGC (SEQ ID NO: 24) |
| 49start.seq | GATCGACCAT GGCTCTGCTC GGACACTCTC TG (SEQ ID NO: 68) |
| 48stop.seq | CGATCGAAGC TTATTACACC AGCTCCTCGG GGTGGC (SEQ ID NO: 69) |
| 77start.seq | GATCGACCAT GGCTCAACTC CATAGCGGCC TT (SEQ ID NO: 70) |
| 76stop.seq | CGATCGAAGC TTATTAGCTC AAGCAGCCTG CCAGCT (SEQ ID NO: 71) |
| 82start.seq | GATCGACCAT GGCTCTTTTC CTCTACCAGG GG (SEQ ID NO: 72) |
| 81stop.seq | CGATCGAAGC TTATTAGCCG CTATGGAGTT GGCTCA (SEQ ID NO: 73) |
| 84start.seq | GATCGACCAT GGCTCTCTAC CAGGGGCTCC TG (SEQ ID NO: 74) |
| 83stop.seq | CGATCGAAGC TTATTAGAAA AGGCCGCTAT GGAGTT (SEQ ID NO: 75) |
| 91start.seq | GATCGACCAT GGCTGCCCTG AAGGGATAT CC (SEQ ID NO: 76) |
| 90stop.seq | CGATCGAAGC TTATTACTGC AGGAGCCCCT GGTAGA (SEQ ID NO: 77) |
| 112start.seq | GATCGACCAT GGCTGACTTT GCCACCACCA TC (SEQ ID NO: 78) |
| 111stop.seq | CGATCGAAGC TTATTAGGCG ACGTCCAGCT GCAGTG (SEQ ID NO: 79) |
| 117start.seq | GATCGACCAT GGCTATCTGG CAGCAGATGG AA (SEQ ID NO: 80) |
| 116stop.seq | CGATCGAAGC TTATTAGGTG GTGGCAAAGT CGGCGA (SEQ ID NO: 81) |
| 119start.seq | GATCGACCAT GGCTCAGCAG ATGGAAGAAC TG (SEQ ID NO: 82) |
| 118stop.seq | CGATCGAAGC TTATTACCAG ATGGTGGTGG CAAAGT (SEQ ID NO: 83) |
| Z4849at.for | CATGGCTTTG TTAGGACATT CTTTAGGTAT TCCATGGGCT CCTCTGAGCT (SEQ ID NO: 84) |
| Z4849at.rev | CAGAGGAGCC CATGGAATAC CTAAAGAATG TCCTAACAAA GC (SEQ ID NO: 85) |

TABLE 2

DNA sequences pMON3485.Seq
```
  1 ATGGCTTACA AGCTGTGCCA CCCCGAGGAG CTGGTGCTGC TCGGACACTC   (SEQ ID NO:25)

51 TCTGGGCATC CCCTGGGCTC CCCTGAGCTC CTGCCCCAGC CAGGCCCTGC

101 AGCTGGCAGG CTGCTTGAGC CAACTCCATA GCGGCCTTTT CCTCTACCAG

151 GGGCTCCTGC AGGCCCTGGA AGGGATATCC CCCGAGTTGG GTCCCACCTT

201 GGACACACTG CAGCTGGACG TCGCCGACTT TGCCACCACC ATCTGGCAGC

251 AGATGGAAGA ACTGGGAATG GCCCCTGCCC TGCAGCCCAC CCAGGGTGCC
```

TABLE 2-continued

DNA sequences

```
301 ATGCCGGCCT TCGCCTCTGC TTTCCAGCGC CGGGCAGGAG GGGTCCTGGT
351 TGCTAGCCAT CTGCAGAGCT TCCTGGAGGT GTCGTACCGC GTTCTACGCC
401 ACCTTGCGCA GCCCTCTGGC GGCTCTGGCG GCTCTCAGAG CTTCCTGCTC
451 AAGTCTTTAG AGCAAGTGAG GAAGATCCAG GGCGATGGCG CAGCGCTCCA
501 GGAGAAGCTG TGTGCCACCT AATAA
``` pMON3486.Seq

```
  1 ATGGCTCCCG AGTTGGGTCC CACCTTGGAC ACACTGCAGC TGGACGTCGC   (SEQ ID NO:26)
 51 CGACTTTGCC ACCACCATCT GGCAGCAGAT GGAAGAACTG GGAATGGCCC
101 CTGCCCTGCA GCCCACCCAG GGTGCCATGC CGGCCTTCGC CTCTGCTTTC
151 CAGCGCCGGG CAGGAGGGGT CCTGGTTGCT AGCCATCTGC AGAGCTTCCT
201 GGAGGTGTCG TACCGCGTTC TACGCCACCT TGCGCAGCCC TCTGGCGGCT
251 CTGGCGGCTC TCAGAGCTTC CTGCTCAAGT CTTTAGAGCA AGTGAGGAAG
301 ATCCAGGGCG ATGGCGCAGC GCTCCAGGAG AAGCTGTGTG CCACCTACAA
351 GCTGTGCCAC CCCGAGGAGC TGGTGCTGCT CGGACACTCT CTGGGCATCC
401 CCTGGGCTCC CCTGAGCTCC TGCCCCAGCC AGGCCCTGCA GCTGGCAGGC
451 TGCTTGAGCC AACTCCATAG CGGCCTTTTC CTCTACCAGG GGCTCCTGCA
501 GGCCCTGGAA GGGATATCCT AATAA
``` pMON3487.Seq

```
  1 ATGGCTATGG CCCCTGCCCT GCAGCCCACC CAGGGTGCCA TGCCGGCCTT   (SEQ ID NO:27)
 51 CGCCTCTGCT TTCCAGCGCC GGGCAGGAGG GGTCCTGGTT GCTAGCCATC
101 TGCAGAGCTT CCTGGAGGTG TCGTACCGCG TTCTACGCCA CCTTGCGCAG
151 CCCTCTGGCG GCTCTGGCGG CTCTCAGAGC TTCCTGCTCA AGTCTTTAGA
201 GCAAGTGAGG AAGATCCAGG GCGATGGCGC AGCGCTCCAG GAGAAGCTGT
251 GTGCCACCTA CAAGCTGTGC ACCCCGAGG AGCTGGTGCT GCTCGGACAC
301 TCTCTGGGCA TCCCCTGGGC TCCCCTGAGC TCCTGCCCCA GCCAGGCCCT
351 GCAGCTGGCA GGCTGCTTGA GCCAACTCCA TAGCGGCCTT TTCCTCTACC
401 AGGGGCTCCT GCAGGCCCTG GAAGGGATAT CCCCGAGTT GGGTCCCACC
451 TTGGACACAC TGCAGCTGGA CGTCGCCGAC TTTGCCACCA CCATCTGGCA
501 GCAGATGGAA GAACTGGGAT AATAA
``` pMON3488.Seq

```
  1 ATGGCTACCC AGGGTGCCAT GCCGGCCTTC GCCTCTGCTT TCCAGCGCCG   (SEQ ID NO:28)
 51 GGCAGGAGGG GTCCTGGTTG CTAGCCATCT GCAGAGCTTC CTGGAGGTGT
101 CGTACCGCGT TCTACGCCAC CTTGCGCAGC CCTCTGGCGG CTCTGGCGGC
151 TCTCAGAGCT TCCTGCTCAA GTCTTTAGAG CAAGTGAGGA AGATCCAGGG
201 CGATGGCGCA GCGCTCCAGG AGAAGCTGTG TGCCACCTAC AAGCTGTGCC
251 ACCCCGAGGA GCTGGTGCTG CTCGGACACT CTCTGGGCAT CCCCTGGGCT
301 CCCCTGAGCT CCTGCCCCAG CCAGGCCCTG CAGCTGGCAG GCTGCTTGAG
351 CCAACTCCAT AGCGGCCTTT TCCTCTACCA GGGGCTCCTG CAGGCCCTGG
```

TABLE 2-continued

DNA sequences

```
401 AAGGGATATC CCCCGAGTTG GGTCCCACCT TGGACACACT GCAGCTGGAC
451 GTCGCCGACT TTGCCACCAC CATCTGGCAG CAGATGGAAG AACTGGGAAT
501 GGCCCCTGCC CTGCAGCCCT AATAA
``` pMON3489.Seq

```
  1 ATGGCTTCTG CTTTCCAGCG CCGGGCAGGA GGGGTCCTGG TTGCTAGCCA   (SEQ ID NO:29)
 51 TCTGCAGAGC TTCCTGGAGG TGTCGTACCG CGTTCTACGC CACCTTGCGC
101 AGCCCTCTGG CGGCTCTGGC GGCTCTCAGA GCTTCCTGCT CAAGTCTTTA
151 GAGCAAGTGA GGAAGATCCA GGGCGATGGC GCAGCGCTCC AGGAGAAGCT
201 GTGTGCCACC TACAAGCTGT GCCACCCCGA GGAGCTGGTG CTGCTCGGAC
251 ACTCTCTGGG CATCCCCTGG GCTCCCCTGA CTCCTGCCC CAGCCAGGCC
301 CTGCAGCTGG CAGGCTGCTT GAGCCAACTC CATAGCGGCC TTTTCCTCTA
351 CCAGGGGCTC CTGCAGGCCC TGGAAGGGAT ATCCCCCGAG TTGGGTCCCA
401 CCTTGGACAC ACTGCAGCTG GACGTCGCCG ACTTTGCCAC CACCATCTGG
451 CAGCAGATGG AAGAACTGGG AATGGCCCCT GCCCTGCAGC CCACCCAGGG
501 TGCCATGCCG GCCTTCGCCT AATAA
``` pMON3490.seq

```
  1 ATGGCTTACA AGCTGTGCCA CCCCGAGGAG CTGGTGCTGC TCGGACACTC   (SEQ ID NO:30)
 51 TCTGGGCATC CCCTGGGCTC CCCTGAGCTC CTGCCCCAGC CAGGCCCTGC
101 AGCTGGCAGG CTGCTTGAGC CAACTCCATA GCGGCCTTTT CCTCTACCAG
151 GGGCTCCTGC AGGCCCTGGA AGGGATATCC CCCGAGTTGG GTCCCACCTT
201 GGACACACTG CAGCTGGACG TCGCCGACTT TGCCACCACC ATCTGGCAGC
251 AGATGGAAGA ACTGGGAATG GCCCCTGCCC TGCAGCCCAC CCAGGGTGCC
301 ATGCCGGCCT TCGCCTCTGC TTTCCAGCGC GGGCAGGAG GGTCCTGGT
351 TGCTAGCCAT CTGCAGAGCT TCCTGGAGGT GTCGTACCGC GTTCTACGCC
401 ACCTTGCGCA GCCCACACCA TTGGGCCCTG CCAGCTCCCT GCCCCAGAGC
451 TTCCTGCTCA AGTCTTTAGA GCAAGTGAGA AAGATCCAGG GCGATGGCGC
501 AGCGCTCCAG GAGAAGCTGT GTGCCACCTA ATAA
``` pMON3491.seq

```
  1 ATGGCTCCCG AGTTGGGTCC CACCTTGGAC ACACTGCAGC TGGACGTCGC   (SEQ ID NO:31)
 51 CGACTTTGCC ACCACCATCT GGCAGCAGAT GGAAGAACTG GGAATGGCCC
101 CTGCCCTGCA GCCCACCCAG GGTGCCATGC CGGCCTTCGC CTCTGCTTTC
151 CAGCGCCGGG CAGGAGGGGT CCTGGTTGCT AGCCATCTGC AGAGCTTCCT
201 GGAGGTGTCG TACCGCGTTC TACGCCACCT TGCGCAGCCC ACACCATTGG
251 GCCCTGCCAG CTCCCTGCCC CAGAGCTTCC TGCTCAAGTC TTTAGAGCAA
301 GTGAGAAAGA TCCAGGGCGA TGGCGCAGCG CTCCAGGAGA AGCTGTGTGC
351 CACCTACAAG CTGTGCCACC CCGAGGAGCT GGTGCTGCTC GGACACTCTC
401 TGGGCATCCC CTGGGCTCCC CTGAGCTCCT GCCCCAGCCA GGCCCTGCAG
451 CTGGCAGGCT GCTTGAGCCA ACTCCATAGC GGCCTTTTCC TCTACCAGGG
501 GCTCCTGCAG GCCCTGGAAG GGATATCCTA ATAA
```

TABLE 2-continued
DNA sequences pMON3492.seq

```
  1 ATGGCTATGG CCCCTGCCCT GCAGCCCACC CAGGGTGCCA TGCCGGCCTT    (SEQ ID NO:32)
 51 CGCCTCTGCT TTCCAGCGCC GGGCAGGAGG GGTCCTGGTT GCTAGCCATC
101 TGCAGAGCTT CCTGGAGGTG TCGTACCGCG TTCTACGCCA CCTTGCGCAG
151 CCCACACCAT TGGGCCCTGC CAGCTCCCTG CCCCAGAGCT TCCTGCTCAA
201 GTCTTTAGAG CAAGTGAGAA AGATCCAGGG CGATGGCGCA GCGCTCCAGG
251 CCCACACCAT TGGGCCCTGC CAGCTCCCTG CCCCAGAGCT TCCTGCTCAA
301 CTCGGACACT CTCTGGGCAT CCCCTGGGCT CCCCTGAGCT CCTGCCCCAG
351 CCAGGCCCTG CAGCTGGCAG GCTGCTTGAG CCAACTCCAT AGCGGCCTTT
401 TCCTCTACCA GGGGCTCCTG CAGGCCCTGG AAGGGATATC CCCCGAGTTG
451 GGTCCCACCT TGGACACACT GCAGCTGGAC GTCGCCGACT TTGCCACCAC
501 CATCTGGCAG CAGATGGAAG AACTGGGATA ATAA
``` pMON3493.seq

```
  1 ATGGCTACCC AGGGTGCCAT GCCGGCCTTC GCCTCTGCTT TCCAGCGCCG    (SEQ ID NO:33)
 51 GGCAGGAGGG GTCCTGGTTG CTAGCCATCT GCAGAGCTTC CTGGAGGTGT
101 CGTACCGCGT TCTACGCCAC CTTGCGCAGC CCACACCATT GGGCCCTGCC
151 AGCTCCCTGC CCCAGAGCTT CCTGCTCAAG TCTTTAGAGC AAGTGAGAAA
201 GATCCAGGGC GATGGCGCAG CGCTCCAGGA GAAGCTGTGT GCCACCTACA
251 AGCTGTGCCA CCCCGAGGAG CTGGTGCTGC TCGGACACTC TCTGGGCATC
301 CCCTGGGCTC CCCTGAGCTC CTGCCCCAGC CAGGCCCTGC AGCTGGCAGG
351 CTGCTTGAGC CAACTCCATA GCGGCCTTTT CCTCTACCAG GGGCTCCTGC
401 AGGCCCTGGA AGGGATATCC CCCGAGTTGG GTCCCACCTT GGACACACTG
451 CAGCTGGACG TCGCCGACTT TGCCACCACC ATCTGGCAGC AGATGGAAGA
501 ACTGGGAATG GCCCCTGCCC TGCAGCCCTA ATAA
``` pMON3494.seq

```
  1 ATGGCTTCTG CTTTCCAGCG CCGGGCAGGA GGGGTCCTGG TTGCTAGCCA    (SEQ ID NO:34)
 51 TCTGCAGAGC TTCCTGGAGG TGTCGTACCG CGTTCTACGC CACCTTGCGC
101 AGCCCACACC ATTGGGCCCT GCCAGCTCCC TGCCCCAGAG CTTCCTGCTC
151 AAGTCTTTAG AGCAAGTGAG AAAGATCCAG GGCGATGGCG CAGCGCTCCA
201 GGAGAAGCTG TGTGCCACCT ACAAGCTGTG CCACCCCGAG GAGCTGGTGC
251 TGCTCGGACA CTCTCTGGGC ATCCCCTGGG CTCCCCTGAG CTCCTGCCCC
301 AGCCAGGCCC TGCAGCTGGC AGGCTGCTTG AGCCAACTCC ATAGCGGCCT
351 TTTCCTCTAC CAGGGGCTCC TGCAGGCCCT GGAAGGGATA TCCCCCGAGT
401 TGGGTCCCAC CTTGGACACA CTGCAGCTGG ACGTCGCCGA CTTTGCCACC
451 ACCATCTGGC AGCAGATGGA AGAACTGGGA ATGGCCCCTG CCCTGCAGCC
501 CACCCAGGGT GCCATGCCGG CCTTCGCCTA ATAA
``` pMON25181.seq

```
  1 ATGGCTCCGG AACTGGGTCC AACTCTGGAC ACACTGCAGC TGGACGTCGC    (SEQ ID NO:35)
```

TABLE 2-continued

| DNA sequences |
|---|

```
 51 CGACTTTGCC ACCACCATCT GGCAGCAGAT GGAAGAACTG GGAATGGCCC

101 CTGCCCTGCA GCCCACCCAG GGTGCCATGC CGGCCTTCGC CTCTGCTTTC

151 CAGCGCCGGG CAGGAGGGGT CCTGGTTGCT AGCCATCTGC AGAGCTTCCT

201 GGAGGTGTCG TACCGCGTTC TACGCCACCT TGCGCAGCCC ACACCATTGG

251 GCCCTGCCAG CTCCCTGCCC CAGAGCTTCC TGCTCAAGTC TTTAGAGCAA

301 GTGAGAAAGA TCCAGGGCGA TGGCGCAGCG CTCCAGGAGA AGCTGTGTGC

351 CACCTACAAG CTGTGCCACC CCGAGGAGCT GGTGCTGCTC GGACACTCTC

401 TGGGCATCCC CTGGGCTCCC CTGAGCTCCT GCCCCAGCCA GGCCCTGCAG

451 CTGGCAGGCT GCTTGAGCCA ACTCCATAGC GGCCTTTTCC TCTACCAGGG

501 GCTCCTGCAG GCCCTGGAAG GGATATCCTA A
``` pMON25182.seq

```
  1 ATGGCTATGG CTCCAGCTCT GCAACCAACT CAAGGTGCAA TGCCAGCATT    (SEQ ID NO:36)

51 TGCATCTGCT TTTCAACGTC GTGCAGGTGG TGTTCTGGTT GCTAGCCATC

101 TGCAGAGCTT CCTGGAGGTG TCGTACCGCG TTCTACGCCA CCTTGCGCAG

151 CCCACACCAT GGGCCCTGCA GCTCCCTG CCCCAGAGCT TCCTGCTCAA

201 GTCTTTAGAG CAAGTGAGAA AGATCCAGGG CGATGGCGCA GCGCTCCAGG

251 AGAAGCTGTG TGCCACCTAC AAGCTGTGCC ACCCCGAGGA GCTGGTGCTG

301 CTCGGACACT CTCTGGGCAT CCCCTGGGCT CCCCTGAGCT CCTGCCCCAG

351 CCAGGCCCTG CAGCTGGCAG GCTGCTTGAG CCAACTCCAT AGCGGCCTTT

401 TCCTCTACCA GGGGCTCCTG CAGGCCCTGG AAGGGATATC CCCGAGTTG

451 GGTCCCACCT GGACACACT GCAGCTGGAC GTCGCCGACT TTGCCACCAC

501 CATCTGGCAG CAGATGGAAG AACTGGGATA A
``` pMON25183.seq

```
  1 ATGGCTACTC AAGGTGCTAT GCCAGCTTTT GCTTCTGCTT TTCAACGTCG    (SEQ ID NO:37)

51 TGCAGGTGGT GTTCTGGTTG CTAGCCATCT GCAGAGCTTC CTGGAGGTGT

101 CGTACCGCGT TCTACGCCAC CTTGCGCAGC CCACACCATT GGGCCCTGCC

151 AGCTCCCTGC CCCAGAGCTT CCTGCTCAAG TCTTTAGAGC AAGTGAGAAA

201 GATCCAGGGC GATGGCGCAG CGCTCCAGGA GAAGCTGTGT GCCACCTACA

251 AGCTGTGCCA CCCCGAGGAG CTGGTGCTGC TCGGACACTC TCTGGGCATC

301 CCCTGGGCTC CCCTGAGCTC CTGCCCCAGC CAGGCCCTGC AGCTGGCAGG

351 CTGCTTGAGC CAACTCCATA GCGGCCTTTT CCTCTACCAG GGGCTCCTGC

401 AGGCCCTGGA AGGGATATCC CCGAGTTGG GTCCCACCTT GGACACACTG

451 CAGCTGGACG TCGCCGACTT TGCCACCACC ATCTGGCAGC AGATGGAAGA

501 ACTGGGAATG GCCCCTGCCC TGCAGCCCTA A
``` pMON25184.seq

```
  1 ATGGCTTCTG CTTTTCAACG TCGTGCAGGT GGTGTTCTGG TTGCTAGCCA    (SEQ ID NO:38)

51 TCTGCAGAGC TTCCTGGAGG TGTCGTACCG CGTTCTACGC CACCTTGCGC

101 AGCCCACACC ATTGGGCCCT GCCAGCTCCC TGCCCCAGAG CTTCCTGCTC

151 AAGTCTTTAG AGCAAGTGAG AAAGATCCAG GGCGATGGCG CAGCGCTCCA
```

TABLE 2-continued

DNA sequences

```
201 GGAGAAGCTG TGTGCCACCT ACAAGCTGTG CCACCCCGAG GAGCTGGTGC
251 TGCTCGGACA CTCTCTGGGC ATCCCCTGGG CTCCCCTGAG CTCCTGCCCC
301 AGCCAGGCCC TGCAGCTGGC AGGCTGCTTG AGCCAACTCC ATAGCGGCCT
351 TTTCCTCTAC CAGGGGCTCC TGCAGGCCCT GGAAGGGATA TCCCCCGAGT
401 TGGGTCCCAC CTTGGACACA CTGCAGCTGG ACGTCGCCGA CTTTGCCACC
451 ACCATCTGGC AGCAGATGGA AGAACTGGGA ATGGCCCCTG CCCTGCAGCC
501 CACCCAGGGT GCCATGCCGG CCTTCGCCTA A
``` pMON25185.seq

```
  1 ATGGCTCCGG AACTGGGTCC AACTCTGGAC ACACTGCAGC TGGACGTCGC   (SEQ ID NO:39)
 51 CGACTTTGCC ACCACCATCT GGCAGCAGAT GGAAGAACTG GGAATGGCCC
101 CTGCCCTGCA GCCCACCCAG GGTGCCATGC CGGCCTTCGC CTCTGCTTTC
151 CAGCGCCGGG CAGGAGGGGT CCTGGTTGCT AGCCATCTGC AGAGCTTCCT
201 GGAGGTGTCG TACCGCGTTC TACGCCACCT GCGCAGCCC TCTGGCGGCT
251 CTGGCGGCTC TCAGAGCTTC CTGCTCAAGT CTTTAGAGCA AGTGAGAAAG
301 ATCCAGGGCG ATGGCGCAGC GCTCCAGGAG AAGCTGTGTG CCACCTACAA
351 GCTGTGCCAC CCCGAGGAGC TGGTGCTGCT CGGACACTCT CTGGGCATCC
401 CCTGGGCTCC CCTGAGCTCC TGCCCCAGCC AGGCCCTGCA GCTGGCAGGC
451 TGCTTGAGCC AACTCCATAG CGGCCTTTTC CTCTACCAGG GGCTCCTGCA
501 GGCCCTGGAA GGGATATCCT AA
``` pMON25186.seq

```
  1 ATGGCTATGG CTCCAGCTCT GCAACCAACT CAAGGTGCAA TGCCAGCATT   (SEQ ID NO:40)
 51 TGCATCTGCT TTTCAACGTC GTGCAGGTGG TGTTCTGGTT GCTAGCCATC
101 TGCAGAGCTT CCTGGAGGTG TCGTACCGCG TTCTACGCCA CCTTGCGCAG
151 CCCTCTGGCG GCTCTGGCGG CTCTCAGAGC TTCCTGCTCA AGTCTTTAGA
201 GCAAGTGAGA AAGATCCAGG GCGATGGCGC AGCGCTCCAG GAGAAGCTGT
251 GTGCCACCTA CAAGCTGTGC ACCCCGAGG AGCTGGTGCT GCTCGGACAC
301 TCTCTGGGCA TCCCCTGGGC TCCCCTGAGC TCCTGCCCCA GCCAGGCCCT
351 GCAGCTGGCA GGCTGCTTGA GCCAACTCCA TAGCGGCCTT TTCCTCTACC
401 AGGGGCTCCT GCAGGCCCTG GAAGGGATAT CCCCCGAGTT GGGTCCCACC
451 TTGGACACAC TGCAGCTGGA CGTCGCCGAC TTTGCCACCA CCATCTGGCA
501 GCAGATGGAA GAACTGGGAT AA
``` pMON25187.seq

```
  1 ATGGCTACTC AAGGTGCTAT GCCAGCTTTT GCTTCTGCTT TTCAACGTCG   (SEQ ID NO:41)
 51 TGCAGGTGGT GTTCTGGTTG CTAGCCATCT GCAGAGCTTC CTGGAGGTGT
101 CGTACCGCGT TCTACGCCAC CTTGCGCAGC CCTCTGGCGG CTCTGGCGGC
151 TCTCAGAGCT TCCTGCTCAA GTCTTTAGAG CAAGTGAGAA AGATCCAGGG
201 CGATGGCGCA GCGCTCCAGG AGAAGCTGTG TGCCACCTAC AAGCTGTGCC
```

TABLE 2-continued

DNA sequences

251 ACCCCGAGGA GCTGGTGCTG CTCGGACACT CTCTGGGCAT CCCCTGGGCT

301 CCCCTGAGCT CCTGCCCCAG CCAGGCCCTG CAGCTGGCAG GCTGCTTGAG

351 CCAACTCCAT AGCGGCCTTT TCCTCTACCA GGGGCTCCTG CAGGCCCTGG

401 AAGGGATATC CCCCGAGTTG GGTCCCACCT TGGACACACT GCAGCTGGAC

451 GTCGCCGACT TTGCCACCAC CATCTGGCAG CAGATGGAAG AACTGGGAAT

501 GGCCCCTGCC CTGCAGCCCT AA pMON25188.seq

1 ATGGCTTCTG CTTTTCAACG TCGTGCAGGT GGTGTTCTGG TTGCTAGCCA  (SEQ ID NO:42)

51 TCTGCAGAGC TTCCTGGAGG TGTCGTACCG CGTTCTACGC CACCTTGCGC

101 AGCCCTCTGG CGGCTCTGGC GGCTCTCAGA GCTTCCTGCT CAAGTCTTTA

151 GAGCAAGTGA GAAAGATCCA GGGCGATGGC GCAGCGCTCC AGGAGAAGCT

201 GTGTGCCACC TACAAGCTGT GCCACCCCGA GGAGCTGGTG CTGCTCGGAC

251 ACTCTCTGGG CATCCCCTGG GCTCCCCTGA GCTCCTGCCC CAGCCAGGCC

301 CTGCAGCTGG CAGGCTGCTT GAGCCAACTC CATAGCGGCC TTTTCCTCTA

351 CCAGGGGCTC CTGCAGGCCC TGGAAGGGAT ATCCCCCGAG TTGGGTCCCA

401 CCTTGGACAC ACTGCAGCTG GACGTCGCCG ACTTTGCCAC CACCATCTGG

451 CAGCAGATGG AAGAACTGGG AATGGCCCCT GCCCTGCAGC CCACCCAGGG

501 TGCCATGCCG GCCTTCGCCT AA pMON3460.seq

1 ATGGCTCTGC TCGGACACTC TCTGGGCATC CCCTGGGCTC CCCTGAGCTC  (SEQ ID NO:86)

51 CTGCCCCAGC CAGGCCCTGC AGCTGGCAGG CTGCTTGAGC CAACTCCATA

101 GCGGCCTTTT CCTCTACCAG GGGCTCCTGC AGGCCCTGGA AGGGATATCC

151 CCCGAGTTGG GTCCCACCTT GGACACACTG CAGCTGGACG TCGCCGACTT

201 TGCCACCACC ATCTGGCAGC AGATGGAAGA ACTGGGAATG GCCCCTGCCC

251 TGCAGCCCAC CCAGGGTGCC ATGCCGGCCT TCGCCTCTGC TTTCCAGCGC

301 CGGGCAGGAG GGGTCCTGGT TGCTAGCCAT CTGCAGAGCT TCCTGGAGGT

351 GTCGTACCGC GTTCTACGCC ACCTTGCGCA GCCCACACCA TTGGGCCCTG

401 CCAGCTCCCT GCCCCAGAGC TTCCTGCTCA AGTCTTTAGA GCAAGTGAGA

451 AAGATCCAGG GCGATGGCGC AGCGCTCCAG GAGAAGCTGT GTGCCACCTA

501 CAAGCTGTGC CACCCCGAGG AGCTGGTGTA ATAA pMON3461.seq

1 ATGGCTCAAC TCCATAGCGG CCTTTTCCTC TACCAGGGGC TCCTGCAGGC  (SEQ ID NO:87)

51 CCTGGAAGGG ATATCCCCCG AGTTGGGTCC CACCTTGGAC ACACTGCAGC

101 TGGACGTCGC CGACTTTGCC ACCACCATCT GGCAGCAGAT GGAAGAACTG

151 GGAATGGCCC TGCCCTGCA GCCCACCCAG GGTGCCATGC CGGCCTTCGC

201 CTCTGCTTTC AGCGCCGGG CAGGAGGGGT CCTGGTTGCT AGCCATCTGC

251 AGAGCTTCCT GGAGGTGTCG TACCGCGTTC TACGCCACCT TGCGCAGCCC

301 ACACCATTGG GCCCTGCCAG CTCCCTGCCC CAGAGCTTCC TGCTCAAGTC

TABLE 2-continued

DNA sequences

351 TTTAGAGCAA GTGAGAAAGA TCCAGGGCGA TGGCGCAGCG CTCCAGGAGA

401 AGCTGTGTGC CACCTACAAG CTGTGCCACC CCGAGGAGCT GGTGCTGCTC

451 GGACACTCTC TGGGCATCCC CTGGGCTCCC CTGAGCTCCT GCCCCAGCCA

501 GGCCCTGCAG CTGGCAGGCT GCTTGAGCTA ATAA pMON3462.seq

1 ATGGCTCTTT TCCTCTACCA GGGGCTCCTG CAGGCCCTGG AAGGGATATC  (SEQ ID NO:88)

51 CCCCGAGTTG GGTCCCACCT TGGACACACT GCAGCTGGAC GTCGCCGACT

101 TTGCCACCAC CATCTGGCAG CAGATGGAAG AACTGGGAAT GGCCCCTGCC

151 CTGCAGCCCA CCCAGGGTGC CATGCCGGCC TTCGCCTCTG CTTTCCAGCG

201 CCGGGCAGGA GGGGTCCTGG TTGCTAGCCA TCTGCAGAGC TTCCTGGAGG

251 TGTCGTACCG CGTTCTACGC CACCTTGCGC AGCCCACACC ATTGGGCCCT

301 GCCAGCTCCC TGCCCCAGAG CTTCCTGCTC AAGTCTTTAG AGCAAGTGAG

351 AAAGATCCAG GGCGATGGCG CAGCGCTCCA GGAGAAGCTG TGTGCCACCT

401 ACAAGCTGTG CCACCCCGAG GAGCTGGTGC TGCTCGGACA CTCTCTGGGC

451 ATCCCCTGGG CTCCCCTGAG CTCCTGCCCC AGCCAGGCCC TGCAGCTGGC

501 AGGCTGCTTG AGCCAACTCC ATAGCGGCTA ATAA pMON3463.seq

1 ATGGCTCTCT ACCAGGGGCT CCTGCAGGCC CTGGAAGGGA TATCCCCCGA  (SEQ ID NO:89)

51 GTTGGGTCCC ACCTTGGACA CACTGCAGCT GGACGTCGCC GACTTTGCCA

101 CCACCATCTG GCAGCAGATG AAGAACTGG GAATGGCCCC TGCCCTGCAG

151 CCCACCCAGG GTGCCATGCC GGCCTTCGCC TCTGCTTTCC AGCGCCGGGC

201 AGGAGGGGTC CTGGTTGCTA GCCATCTGCA GAGCTTCCTG GAGGTGTCGT

251 ACCGCGTTCT ACGCCACCTT GCGCAGCCCA CACCATTGGG CCCTGCCAGC

301 TCCCTGCCCC AGAGCTTCCT GCTCAAGTCT TTAGAGCAAG TGAGAAAGAT

351 CCAGGGCGAT GGCGCAGCGC TCCAGGAGAA GCTGTGTGCC ACCTACAAGC

401 TGTGCCACCC CGAGGAGCTG GTGCTGCTCG GACACTCTCT GGGCATCCCC

451 TGGGCTCCCC TGAGCTCCTG CCCCAGCCAG GCCCTGCAGC TGGCAGGCTG

501 CTTGAGCCAA CTCCATAGCG GCCTTTTCTA ATAA pMON3464.seq

1 ATGGCTGCCC TGGAAGGGAT ATCCCCCGAG TTGGGTCCCA CCTTGGACAC  (SEQ ID NO:90)

51 ACTGCAGCTG GACGTCGCCG ACTTTGCCAC CACCATCTGG CAGCAGATGG

101 AAGAACTGGG AATGGCCCCT GCCCTGCAGC CCACCCAGGG TGCCATGCCG

151 GCCTTCGCCT CTGCTTTCCA GCGCCGGGCA GGAGGGGTCC TGGTTGCTAG

201 CCATCTGCAG AGCTTCCTGG AGGTGTCGTA CCGCGTTCTA CGCCACCTTG

251 CGCAGCCCAC CATTGGGC CCTGCCAGCT CCCTGCCCCA GAGCTTCCTG

301 CTCAAGTCTT TAGAGCAAGT GAGAAAGATC CAGGGCGATG GCGCAGCGCT

351 CCAGGAGAAG CTGTGTGCCA CCTACAAGCT GTGCCACCCC GAGGAGCTGG

TABLE 2-continued

DNA sequences

401 TGCTGCTCGG ACACTCTCTG GGCATCCCCT GGGCTCCCCT GAGCTCCTGC

451 CCCAGCCAGG CCCTGCAGCT GGCAGGCTGC TTGAGCCAAC TCCATAGCGG

501 CCTTTTCCTC TACCAGGGGC TCCTGCAGTA ATAA pMON3465.seq

1 ATGGCTGACT TTGCCACCAC CATCTGGCAG CAGATGGAAG AACTGGGAAT   (SEQ ID NO:91)

51 GGCCCCTGCC CTGCAGCCCA CCCAGGGTGC CATGCCGGCC TTCGCCTCTG

101 CTTTCCAGCG CCGGGCAGGA GGGGTCCTGG TTGCTAGCCA TCTGCAGAGC

151 TTCCTGGAGG TGTCGTACCG CGTTCTACGC CACCTTGCGC AGCCCACACC

201 ATTGGGCCCT GCCAGCTCCC TGCCCCAGAG CTTCCTGCTC AAGTCTTTAG

251 AGCAAGTGAG AAAGATCCAG GGCGATGGCG CAGCGCTCCA GGAGAAGCTG

301 TGTGCCACCT ACAAGCTGTG CCACCCCGAG GAGCTGGTGC TGCTCGGACA

351 CTCTCTGGGC ATCCCCTGGG CTCCCCTGAG CTCCTGCCCC AGCCAGGCCC

401 TGCAGCTGGC AGGCTGCTTG AGCCAACTCC ATAGCGGCCT TTTCCTCTAC

451 CAGGGGCTCC TGCAGGCCCT GGAAGGGATA TCCCCCGAGT TGGGTCCCAC

501 CTTGGACACA CTGCAGCTGG ACGTCGCCTA ATAA pMON3466.seq

1 ATGGCTATCT GGCAGCAGAT GGAAGAACTG GGAATGGCCC CTGCCCTGCA   (SEQ ID NO:92)

51 GCCCACCCAG GGTGCCATGC CGGCCTTCGC CTCTGCTTTC AGCGCCGGG

101 CAGGAGGGGT CCTGGTTGCT AGCCATCTGC AGAGCTTCCT GGAGGTGTCG

151 TACCGCGTTC TACGCCACCT GCGCAGCCC ACACCATTGG GCCCTGCCAG

201 CTCCCTGCCC CAGAGCTTCC TGCTCAAGTC TTTAGAGCAA GTGAGAAAGA

251 TCCAGGGCGA TGGCGCAGCG CTCCAGGAGA AGCTGTGTGC CACCTACAAG

301 CTGTGCCACC CCGAGGAGCT GGTGCTGCTC GGACACTCTC TGGGCATCCC

351 CTGGGCTCCC CTGAGCTCCT GCCCCAGCCA GGCCCTGCAG CTGGCAGGCT

401 GCTTGAGCCA ACTCCATAGC GGCCTTTTCC TCTACCAGGG GCTCCTGCAG

451 GCCCTGGAAG GGATATCCCC CGAGTTGGGT CCCACCTTGG ACACACTGCA

501 GCTGGACGTC GCCGACTTTG CCACCACCTA ATAA pMON3467.seq

1 ATGGCTCAGC AGATGGAAGA ACTGGGAATG GCCCCTGCCC TGCAGCCCAC   (SEQ ID NO:93)

51 CCAGGGTGCC ATGCCGGCCT TCGCCTCTGC TTTCCAGCGC CGGGCAGGAG

101 GGGTCCTGGT TGCTAGCCAT CTGCAGAGCT TCCTGGAGGT GTCGTACCGC

151 GTTCTACGCC ACCTTGCGCA GCCCACACCA TTGGGCCCTG CCAGCTCCCT

201 GCCCCAGAGC TTCCTGCTCA AGTCTTTAGA GCAAGTGAGA AAGATCCAGG

251 GCGATGGCGC AGCGCTCCAG GAGAAGCTGT GTGCCACCTA CAAGCTGTGC

301 CACCCCGAGG AGCTGGTGCT GCTCGGACAC TCTCTGGGCA TCCCCTGGGC

351 TCCCCTGAGC TCCTGCCCCA GCCAGGCCCT GCAGCTGGCA GGCTGCTTGA

401 GCCAACTCCA TAGCGGCCTT TTCCTCTACC AGGGGCTCCT GCAGGCCCTG

TABLE 2-continued

DNA sequences

451 GAAGGGATAT CCCCCGAGTT GGGTCCCACC TTGGACACAC TGCAGCTGGA
501 CGTCGCCGAC TTTGCCACCA CCATCTGGTA ATAA pMON3499.seq 1 ATGGCTTTGT TAGGACATTC TTTAGGTATT CCATGGGCTC CTCTGAGCTC   (SEQ ID NO:94)
 51 CTGCCCCAGC CAGGCCCTGC AGCTGGCAGG CTGCTTGAGC CAACTCCATA
101 GCGGCCTTTT CCTCTACCAG GGGCTCCTGC AGGCCCTGGA AGGGATATCC
151 CCCGAGTTGG GTCCCACCTT GGACACACTG CAGCTGGACG TCGCCGACTT
201 TGCCACCACC ATCTGGCAGC AGATGGAAGA ACTGGGAATG GCCCCTGCCC
251 TGCAGCCCAC CCAGGGTGCC ATGCCGGCCT TCGCCTCTGC TTTCCAGCGC
301 CGGGCAGGAG GGGTCCTGGT TGCTAGCCAT CTGCAGAGCT TCCTGGAGGT
351 GTCGTACCGC GTTCTACGCC ACCTTGCGCA GCCCACACCA TTGGGCCCTG
401 CCAGCTCCCT GCCCCAGAGC TTCCTGCTCA AGTCTTTAGA GCAAGTGAGA
451 AAGATCCAGG GCGATGGCGC AGCGCTCCAG GAGAAGCTGT GTGCCACCTA
501 CAAGCTGTGC CACCCCGAGG AGCTGGTGTA ATAA pG1110.Seq 1 CAGAGCTTCC TGCTCAAGTC TTTAGAGCAA GTGAGGAAGA TCCAGGGCGA   (SEQ ID NO:116)
 51 TGGCGCAGCG CTCCAGGAGA AGCTGTGTGC CACCTACAAG CTGTGCCACC
101 CCGAGGAGCT GGTGCTGCTC GGACACTCTC TGGGCATCCC CTGGGCTCCC
151 CTGAGCTCCT GCCCCAGCCA GGCCCTGCAG CTGGCAGGCT GCTTGAGCCA
201 ACTCCATAGC GGCCTTTTCC TCTACCAGGG GCTCCTGCAG GCCCTGGAAG
251 GGATATCCCC CGAGTTGGGT CCCACCTTGG ACACACTGCA GCTGGACGTC
301 GCCGACTTTG CCACCACCAT CTGGCAGCAG ATGGAAGAAC TGGGAATGGC
351 CCCTGCCCTG CAGCCCACCC AGGGTGCCAT GCCGGCCTTC GCCTCTGCTT
401 TCCAGCGCCG GGCAGGAGGG GTCCTGGTTG CTAGCCATCT GCAGAGCTTC
451 CTGGAGGTGT CGTACCGCGT TCTACGCCAC CTTGCGCAGC CCGACATGGC
501 TACACCATTA GGCCCTGCCA GCTCCCTGCC C pG123122.Seq 1 GAACTGGGAA TGGCCCCTGC CCTGCAGCCC ACCCAGGGTG CCATGCCGGC   (SEQ ID NO:117)
 51 CTTCGCCTCT GCTTTCCAGC GCCGGGCAGG AGGGGTCCTG GTTGCTAGCC
101 ATCTGCAGAG CTTCCTGGAG GTGTCGTACC GCGTTCTACG CCACCTTGCG
151 CAGCCCGACA TGGCTACACC ATTAGGCCCT GCCAGCTCCC TGCCCCAGAG
201 CTTCCTGCTC AAGTCTTTAG AGCAAGTGAG GAAGATCCAG GGCGATGGCG
251 CAGCGCTCCA GGAGAAGCTG TGTGCCACCT ACAAGCTGTG CCACCCCGAG
301 GAGCTGGTGC TGCTCGGACA CTCTCTGGGC ATCCCCTGGG CTCCCCTGAG
351 CTCCTGCCCC AGCCAGGCCC TGCAGCTGGC AGGCTGCTTG AGCCAACTCC
401 ATAGCGGCCT TTTCCTCTAC CAGGGGCTCC TGCAGGCCCT GGAAGGGATA
451 TCCCCCGAGT GGGTCCCAC CTTGGACACA CTGCAGCTGG ACGTCGCCGA TABLE 2-continued DNA sequences

501 CTTTGCCACC ACCATCTGGC AGCAGATGGA A pG125124.Seq

1 GGAATGGCCC CTGCCCTGCA GCCCACCCAG GGTGCCATGC CGGCCTTCGC    (SEQ ID NO:118)
 51 CTCTGCTTTC AGCGCCGGG CAGGAGGGGT CCTGGTTGCT AGCCATCTGC
101 AGAGCTTCCT GGAGGTGTCG TACCGCGTTC TACGCCACCT TGCGCAGCCC
151 GACATGGCTA CACCATTAGG CCCTGCCAGC TCCCTGCCCC AGAGCTTCCT
201 GCTCAAGTCT TTAGAGCAAG TGAGGAAGAT CCAGGGCGAT GGCGCAGCGC
251 TCCAGGAGAA GCTGTGTGCC ACCTACAAGC TGTGCCACCC CGAGGAGCTG
301 GTGCTGCTCG GACACTCTCT GGGCATCCCC TGGGCTCCCC TGAGCTCCTG
351 CCCCAGCCAG GCCCTGCAGC TGGCAGGCTG CTTGAGCCAA CTCCATAGCG
401 GCCTTTTCCT CTACCAGGGG CTCCTGCAGG CCCTGGAAGG GATATCCCCC
451 GAGTTGGGTC CACCTTGGA CACACTGCAG CTGGACGTCG CCGACTTTGC
501 CACCACCATC TGGCAGCAGA TGGAAGAACT G pG1312.Seq

1 TTCCTGCTCA AGTCTTTAGA GCAAGTGAGG AAGATCCAGG GCGATGGCGC    (SEQ ID NO:119)
 51 AGCGCTCCAG GAGAAGCTGT GTGCCACCTA CAAGCTGTGC CACCCCGAGG
101 AGCTGGTGCT GCTCGGACAC TCTCTGGGCA TCCCCTGGGC TCCCCTGAGC
151 TCCTGCCCCA GCCAGGCCCT GCAGCTGGCA GGCTGCTTGA GCCAACTCCA
201 TAGCGGCCTT TTCCTCTACC AGGGGCTCCT GCAGGCCCTG GAAGGGATAT
251 CCCCCGAGTT GGGTCCCACC TTGGACACAC TGCAGCTGGA CGTCGCCGAC
301 TTTGCCACCA CCATCTGGCA GCAGATGGAA GAACTGGGAA TGGCCCCTGC
351 CCTGCAGCCC ACCCAGGGTG CCATGCCGGC CTTCGCCTCT GCTTTCCAGC
401 GCCGGGCAGG AGGGGTCCTG GTTGCTAGCC ATCTGCAGAG CTTCCTGGAG
451 GTGTCGTACC GCGTTCTACG CCACCTTGCG CAGCCCGACA TGGCTACACC
501 ATTAGGCCCT GCCAGCTCCC TGCCCCAGAG C pG159158.Seq

1 AGCTTCCTGG AGGTGTCGTA CCGCGTTCTA CGCCACCTTG CGCAGCCCGA    (SEQ ID NO:120)
 51 CATGGCTACA CCATTAGGCC CTGCCAGCTC CCTGCCCCAG AGCTTCCTGC
101 TCAAGTCTTT AGAGCAAGTG AGGAAGATCC AGGGCGATGG CGCAGCGCTC
151 CAGGAGAAGC TGTGTGCCAC CTACAAGCTG TGCCACCCCG AGGAGCTGGT
201 GCTGCTCGGA CACTCTCTGG GCATCCCCTG GCTCCCCTG AGCTCCTGCC
251 CCAGCCAGGC CCTGCAGCTG GCAGGCTGCT TGAGCCAACT CCATAGCGGC
301 CTTTTCCTCT ACCAGGGGCT CCTGCAGGCC CTGGAAGGGA TATCCCCCGA
351 GTTGGGTCCC ACCTTGGACA CACTGCAGCT GGACGTCGCC GACTTTGCCA
401 CCACCATCTG GCAGCAGATG AAGAACTGG GAATGGCCCC TGCCCTGCAG
451 CCCACCCAGG GTGCCATGCC GGCCTTCGCC TCTGCTTTCC AGCGCCGGGC
501 AGGAGGGGTC CTGGTTGCTA GCCATCTGCA G pG1918.Seq

1 GAGCAAGTGA GGAAGATCCA GGGCGATGGC GCAGCGCTCC AGGAGAAGCT    (SEQ ID NO:121)

TABLE 2-continued

DNA sequences

```
 51 GTGTGCCACC TACAAGCTGT GCCACCCCGA GGAGCTGGTG CTGCTCGGAC
101 ACTCTCTGGG CATCCCCTGG GCTCCCCTGA GCTCCTGCCC CAGCCAGGCC
151 CTGCAGCTGG CAGGCTGCTT GAGCCAACTC CATAGCGGCC TTTTCCTCTA
201 CCAGGGGCTC CTGCAGGCCC TGGAAGGGAT ATCCCCCGAG TTGGGTCCCA
251 CCTTGGACAC ACTGCAGCTG GACGTCGCCG ACTTTGCCAC CACCATCTGG
301 CAGCAGATGG AAGAACTGGG AATGGCCCCT GCCCTGCAGC CCACCCAGGG
351 TGCCATGCCG GCCTTCGCCT CTGCTTTCCA GCGCCGGGCA GGAGGGGTCC
401 TGGTTGCTAG CCATCTGCAG AGCTTCCTGG AGGTGTCGTA CCGCGTTCTA
451 CGCCACCTTG CGCAGCCCGA CATGGCTACA CCATTAGGCC CTGCCAGCTC
501 CCTGCCCCAG AGCTTCCTGC TCAAGTCTTT A
``` pG32.Seq

```
  1 TTAGGCCCTG CCAGCTCCCT GCCCCAGAGC TTCCTGCTCA AGTCTTTAGA   (SEQ ID NO:122)
 51 GCAAGTGAGG AAGATCCAGG GCGATGGCGC AGCGCTCCAG GAGAAGCTGT
101 GTGCCACCTA CAAGCTGTGC CACCCCGAGG AGCTGGTGCT GCTCGGACAC
151 TCTCTGGGCA TCCCCTGGGC TCCCCTGAGC TCCTGCCCCA GCCAGGCCCT
201 GCAGCTGGCA GGCTGCTTGA GCCAACTCCA TAGCGGCCTT TTCCTCTACC
251 AGGGGCTCCT GCAGGCCCTG AAGGGATAT CCCCCGAGTT GGGTCCCACC
301 TTGGACACAC TGCAGCTGGA CGTCGCCGAC TTTGCCACCA CCATCTGGCA
351 GCAGATGGAA GAACTGGGAA TGGCCCCTGC CCTGCAGCCC ACCCAGGGTG
401 CCATGCCGGC CTTCGCCTCT GCTTTCCAGC GCCGGGCAGG AGGGGTCCTG
451 GTTGCTAGCC ATCTGCAGAG CTTCCTGGAG GTGTCGTACC GCGTTCTACG
501 CCACCTTGCG CAGCCCGACA TGGCTACACC A
``` pG4948.Seq

```
  1 CTGCTCGGAC ACTCTCTGGG CATCCCCTGG GCTCCCCTGA GCTCCTGCCC   (SEQ ID NO:123)
 51 CAGCCAGGCC CTGCAGCTGG CAGGCTGCTT GAGCCAACTC CATAGCGGCC
101 TTTTCCTCTA CCAGGGGCTC CTGCAGGCCC TGGAAGGGAT ATCCCCCGAG
151 TTGGGTCCCA CCTTGGACAC ACTGCAGCTG GACGTCGCCG ACTTTGCCAC
201 CACCATCTGG CAGCAGATGG AAGAACTGGG AATGGCCCCT GCCCTGCAGC
251 CCACCCAGGG TGCCATGCCG GCCTTCGCCT CTGCTTTCCA GCGCCGGGCA
301 GGAGGGGTCC TGGTTGCTAG CCATCTGCAG AGCTTCCTGG AGGTGTCGTA
351 CCGCGTTCTA CGCCACCTTG CGCAGCCCGA CATGGCTACA CCATTAGGCC
401 CTGCCAGCTC CCTGCCCCAG AGCTTCCTGC TCAAGTCTTT AGAGCAAGTG
451 AGGAAGATCC AGGGCGATGG CGCAGCGCTC CAGGAGAAGC TGTGTGCCAC
501 CTACAAGCTG TGCCACCCCG AGGAGCTGGT G
``` pG6059.Seq

```
  1 CCCCTGAGCT CCTGCCCCAG CCAGGCCCTG CAGCTGGCAG GCTGCTTGAG   (SEQ ID NO:124)
 51 CCAACTCCAT AGCGGCCTTT TCCTCTACCA GGGGCTCCTG CAGGCCCTGG
101 AAGGGATATC CCCCGAGTTG GGTCCCACCT GGACACACT GCAGCTGGAC
```

TABLE 2-continued

DNA sequences

```
151 GTCGCCGACT TTGCCACCAC CATCTGGCAG CAGATGGAAG AACTGGGAAT

201 GGCCCCTGCC CTGCAGCCCA CCCAGGGTGC CATGCCGGCC TTCGCCTCTG

251 CTTTCCAGCG CCGGGCAGGA GGGGTCCTGG TTGCTAGCCA TCTGCAGAGC

301 TTCCTGGAGG TGTCGTACCG CGTTCTACGC CACCTTGCGC AGCCCGACAT

351 GGCTACACCA TTAGGCCCTG CCAGCTCCCT GCCCCAGAGC TTCCTGCTCA

401 AGTCTTTAGA GCAAGTGAGG AAGATCCAGG GCGATGGCGC AGCGCTCCAG

451 GAGAAGCTGT GTGCCACCTA CAAGCTGTGC CACCCCGAGG AGCTGGTGCT

501 GCTCGGACAC TCTCTGGGCA TCCCCTGGGC T
``` pG6766.Seq

```
  1 CAGGCCCTGC AGCTGGCAGG CTGCTTGAGC CAACTCCATA GCGGCCTTTT    (SEQ ID NO:125)

51 CCTCTACCAG GGGCTCCTGC AGGCCCTGGA AGGGATATCC CCCGAGTTGG

101 GTCCCACCTT GGACACACTG CAGCTGGACG TCGCCGACTT TGCCACCACC

151 ATCTGGCAGC AGATGGAAGA ACTGGGAATG CCCCTGCCC TGCAGCCCAC

201 CCAGGGTGCC ATGCCGGCCT TCGCCTCTGC TTTCCAGCGC CGGGCAGGAG

251 GGGTCCTGGT TGCTAGCCAT CTGCAGAGCT TCCTGGAGGT GTCGTACCGC

301 GTTCTACGCC ACCTTGCGCA GCCCGACATG GCTACACCAT TAGGCCCTGC

351 CAGCTCCCTG CCCCAGAGCT TCCTGCTCAA GTCTTTAGAG CAAGTGAGGA

401 AGATCCAGGG CGATGGCGCA GCGCTCCAGG AGAAGCTGTG TGCCACCTAC

451 AAGCTGTGCC ACCCCGAGGA GCTGGTGCTG CTCGGACACT CTCTGGGCAT

501 CCCCTGGGCT CCCCTGAGCT CCTGCCCCAG C
``` pG6968.Seq

```
  1 CTGCAGCTGG CAGGCTGCTT GAGCCAACTC CATAGCGGCC TTTTCCTCTA    (SEQ ID NO:126)

51 CCAGGGGCTC CTGCAGGCCC TGGAAGGGAT ACCCCCGAG TTGGGTCCCA

101 CCTTGGACAC ACTGCAGCTG GACGTCGCCG ACTTTGCCAC CACCATCTGG

151 CAGCAGATGG AAGAACTGGG AATGGCCCCT GCCCTGCAGC CCACCCAGGG

201 TGCCATGCCG GCCTTCGCCT CTGCTTTCCA GCGCCGGGCA GGAGGGGTCC

251 TGGTTGCTAG CCATCTGCAG AGCTTCCTGG AGGTGTCGTA CCGCGTTCTA

301 CGCCACCTTG CGCAGCCCGA CATGGCTACA CCATTAGGCC CTGCCAGCTC

351 CCTGCCCCAG AGCTTCCTGC TCAAGTCTTT AGAGCAAGTG AGGAAGATCC

401 AGGGCGATGG CGCAGCGCTC CAGGAGAAGC TGTGTGCCAC CTACAAGCTG

451 TGCCACCCCG AGGAGCTGGT GCTGCTCGGA CACTCTCTGG GCATCCCCTG

501 GGCTCCCCTG AGCTCCTGCC CCAGCCAGGC C
``` pG7170.Seq

```
  1 CTGGCAGGCT GCTTGAGCCA ACTCCATAGC GGCCTTTTCC TCTACCAGGG    (SEQ ID NO:127)

51 GCTCCTGCAG GCCCTGGAAG GGATATCCCC CGAGTTGGGT CCCACCTTGG

101 ACACACTGCA GCTGGACGTC GCCGACTTTG CCACCACCAT CTGGCAGCAG

151 ATGGAAGAAC TGGGAATGGC CCCTGCCCTG CAGCCCACCC AGGGTGCCAT

201 GCCGGCCTTC GCCTCTGCTT TCCAGCGCCG GGCAGGAGGG GTCCTGGTTG

251 CTAGCCATCT GCAGAGCTTC CTGGAGGTGT CGTACCGCGT TCTACGCCAC
```

TABLE 2-continued

DNA sequences

```
301 CTTGCGCAGC CCGACATGGC TACACCATTA GGCCCTGCCA GCTCCCTGCC

351 CCAGAGCTTC CTGCTCAAGT CTTTAGAGCA AGTGAGGAAG ATCCAGGGCG

401 ATGGCGCAGC GCTCCAGGAG AAGCTGTGTG CCACCTACAA GCTGTGCCAC

451 CCCGAGGAGC TGGTGCTGCT CGGACACTCT CTGGGCATCC CCTGGGCTCC

501 CCTGAGCTCC TGCCCCAGCC AGGCCCTGCA G
``` pG170169-seq

```
  1 CACCTTGCGC AGCCCGACAT GGCTACACCA TTAGGCCCTG CCAGCTCCCT    (SEQ ID NO:129)

51 GCCCCAGAGC TTCCTGCTCA AGTCTTTAGA GCAAGTGAGG AAGATCCAGG

101 GCGATGGCGC AGCGCTCCAG GAGAAGCTGT GTGCCACCTA CAAGCTGTGC

151 CACCCCGAGG AGCTGGTGCT GCTCGGACAC TCTCTGGGCA TCCCCTGGGC

201 TCCCCTGAGC TCCTGCCCCA GCCAGGCCCT GCAGCTGGCA GGCTGCTTGA

251 GCCAACTCCA TAGCGGCCTT TTCCTCTACC AGGGGCTCCT GCAGGCCCTG

301 GAAGGGATAT CCCCCGAGTT GGGTCCCACC TTGGACACAC TGCAGCTGGA

351 CGTCGCCGAC TTTGCCACCA CCATCTGGCA GCAGATGGAA GAACTGGGAA

401 TGGCCCCTGC CCTGCAGCCC ACCCAGGGTG CCATGCCGGC CTTCGCCTCT

451 GCTTTCCAGC GCCGGGCAGG AGGGGTCCTG GTTGCTAGCC ATCTGCAGAG

501 CTTCCTGGAG GTGTCGTACC GCGTTCTACG C
```

TABLE 3

PROTEIN SEQUENCES pMON3485.Pep
(SEQ ID NO:43)

Tyr Lys Leu Cys His Pro Glu Glu Leu Val Leu Leu

Gly His Ser Leu Gly Ile Pro Trp Ala Pro Leu Ser

Ser Cys Pro Ser Gln Ala Leu Gln Leu Ala Gly Cys

Leu Ser Gln Leu His Ser Gly Leu Phe Leu Tyr Gln

Gly Leu Leu Gln Ala Leu Glu Gly Ile Ser Pro Glu

Leu Gly Pro Thr Leu Asp Thr Leu Gln Leu Asp Val

Ala Asp Phe Ala Thr Thr Ile Trp Gln Gln Met Glu

Glu Leu Gly Met Ala Pro Ala Leu Gln Pro Thr Gln

Gly Ala Met Pro Ala Phe Ala Ser Ala Phe Gln Arg

Arg Ala Gly Gly Val Leu Val Ala Ser His Leu Gln

Ser Phe Leu Glu Val Ser Tyr Arg Val Leu Arg His

Leu Ala Gln Pro Ser Gly Gly Ser Gly Gly Ser Gln

Ser Phe Leu Leu Lys Ser Leu Glu Gln Val Arg Lys

Ile Gln Gly Asp Gly Ala Ala Leu Gln Glu Lys Leu

Cys Ala Thr pMON3486.Pep
(SEQ ID NO:44)

Pro Glu Leu Gly Pro Thr Leu Asp Thr Leu Gln Leu

Asp Val Ala Asp Phe Ala Thr Thr Ile Trp Gln Gln

Met Glu Glu Leu Gly Met Ala Pro Ala Leu Gln Pro

Thr Gln Gly Ala Met Pro Ala Phe Ala Ser Ala Phe

Gln Arg Arg Ala Gly Gly Val Leu Val Ala Ser His

Leu Gln Ser Phe Leu Glu Val Ser Tyr Arg Val Leu

Arg His Leu Ala Gln Pro Ser Gly Gly Ser Gly Gly

Ser Gln Ser Phe Leu Leu Lys Ser Leu Glu Gln Val

Arg Lys Ile Gln Gly Asp Gly Ala Ala Leu Gln Glu

Lys Leu Cys Ala Thr Tyr Lys Leu Cys His Pro Glu

Glu Leu Val Leu Leu Gly His Ser Leu Gly Ile Pro

Trp Ala Pro Leu Ser Ser Cys Pro Ser Gln Ala Leu

Gln Leu Ala Gly Cys Leu Ser Gln Leu His Ser Gly

Leu Phe Leu Tyr Gln Gly Leu Leu Gln Ala Leu Glu

Gly Ile Ser pMON3487.Pep
(SEQ ID NO:45)

TABLE 3-continued
PROTEIN SEQUENCES

Met Ala Pro Ala Leu Gln Pro Thr Gln Gly Ala Met
Pro Ala Phe Ala Ser Ala Phe Gln Arg Arg Ala Gly
Gly Val Leu Val Ala Ser His Leu Gln Ser Phe Leu
Glu Val Ser Tyr Arg Val Leu Arg His Leu Ala Gln
Pro Ser Gly Gly Ser Gly Gly Ser Gln Ser Phe Leu
Leu Lys Ser Leu Glu Gln Val Arg Lys Ile Gln Gly
Asp Gly Ala Ala Leu Gln Glu Lys Leu Cys Ala Thr
Tyr Lys Leu Cys His Pro Glu Glu Leu Val Leu Leu
Gly His Ser Leu Gly Ile Pro Trp Ala Pro Leu Ser
Ser Cys Pro Ser Gln Ala Leu Gln Leu Ala Gly Cys
Leu Ser Gln Leu His Ser Gly Leu Phe Leu Tyr Gln
Gly Leu Leu Gln Ala Leu Glu Gly Ile Ser Pro Glu
Leu Gly Pro Thr Leu Asp Gln Met Glu Glu Leu Gly pMON3488.Pep
(SEQ ID NO:46)
Thr Gln Gly Ala Met Pro Ala Phe Ala Ser Ala Phe
Gln Arg Arg Ala Gly Gly Val Leu Val Ala Ser His
Leu Gln Ser Phe Leu Glu Val Ser Tyr Arg Val Leu
Arg His Leu Ala Gln Pro Ser Gly Gly Ser Gly Gly
Ser Gln Ser Phe Leu Leu Lys Ser Leu Glu Gln Val
Arg Lys Ile Gln Gly Asp Gly Ala Ala Leu Gln Glu
Lys Leu Cys Ala Thr Tyr Lys Leu Cys His Pro Glu
Glu Leu Val Leu Leu Gly His Ser Leu Gly Ile Pro
Trp Ala Pro Leu Ser Ser Cys Pro Ser Gln Ala Leu
Gln Leu Ala Gly Cys Leu Ser Gln Leu His Ser Gly
Leu Phe Leu Tyr Gln Gly Leu Leu Gln Ala Leu Glu
Gly Ile Ser Pro Glu Leu Gly Pro Thr Leu Asp Thr
Leu Gln Leu Asp Val Ala Asp Phe Ala Thr Thr Ile
Trp Gln Gln Met Glu Glu Leu Gly Met Ala Pro Ala
Leu Gln Pro pMON3489.Pep
(SEQ ID NO:47)
Ser Ala Phe Gln Arg Arg Ala Gly Gly Val Leu Val
Ala Ser His Leu Gln Ser Phe Leu Glu Val Ser Tyr
Arg Val Leu Arg His Leu Ala Gln Pro Ser Gly Gly
Ser Gly Gly Ser Gln Ser Phe Leu Leu Lys Ser Leu
Glu Gln Val Arg Lys Ile Gln Gly Asp Gly Ala Ala
Leu Gln Glu Lys Leu Cys Ala Thr Tyr Lys Leu Cys
His Pro Glu Glu Leu Val Leu Leu Gly His Ser Leu
Gly Ile Pro Trp Ala Pro Leu Ser Ser Cys Pro Ser

Gln Ala Leu Gln Leu Ala Gly Cys Leu Ser Gln Leu
His Ser Gly Leu Phe Leu Tyr Gln Gly Leu Leu Gln
Ala Leu Glu Gly Ile Ser Pro Glu Leu Gly Pro Thr
Leu Asp Thr Leu Gln Leu Asp Val Ala Asp Phe Ala
Thr Thr Ile Trp Gln Gln Met Glu Glu Leu Gly Met
Ala Pro Ala Leu Gln Pro Thr Gln Gly Ala Met Pro
Ala Phe Ala pMON3490.Pep
(SEQ ID NO:48)
Tyr Lys Leu Cys His Pro Glu Glu Leu Val Leu Leu
Gly His Ser Leu Gly Ile Pro Trp Ala Pro Leu Ser
Ser Cys Pro Ser Gln Ala Leu Gln Leu Ala Gly Cys
Leu Ser Gln Leu His Ser Gly Leu Phe Leu Tyr Gln
Gly Leu Leu Gln Ala Leu Glu Gly Ile Ser Pro Glu
Leu Gly Pro Thr Leu Asp Thr Leu Gln Leu Asp Val
Ala Asp Phe Ala Thr Thr Ile Trp Gln Gln Met Glu
Glu Leu Gly Met Ala Pro Ala Leu Gln Pro Thr Gln
Gly Ala Met Pro Ala Phe Ala Ser Ala Phe Gln Arg
Arg Ala Gly Gly Val Leu Val Ala Ser His Leu Gln
Ser Phe Leu Glu Val Ser Tyr Arg Val Leu Arg His
Leu Ala Gln Pro Thr Pro Leu Gly Pro Ala Ser Ser
Leu Pro Gln Ser Phe Leu Leu Lys Ser Leu Glu Gln
Val Arg Lys Ile Gln Gly Asp Gly Ala Ala Leu Gln
Glu Lys Leu Cys Ala Thr pMON3491.Pep
(SEQ ID NO:49)
Pro Glu Leu Gly Pro Thr Leu Asp Thr Leu Gln Leu
Asp Val Ala Asp Phe Ala Thr Thr Ile Trp Gln Gln
Met Glu Glu Leu Gly Met Ala Pro Ala Leu Gln Pro
Thr Gln Gly Ala Met Pro Ala Phe Ala Ser Ala Phe
Gln Arg Arg Ala Gly Gly Val Leu Val Ala Ser His
Leu Gln Ser Phe Leu Glu Val Ser Tyr Arg Val Leu
Arg His Leu Ala Gln Pro Thr Pro Leu Gly Pro Ala
Ser Ser Leu Pro Gln Ser Phe Leu Leu Lys Ser Leu
Glu Gln Val Arg Lys Ile Gln Gly Asp Gly Ala Ala
Leu Gln Glu Lys Leu Cys Ala Thr Tyr Lys Leu Cys
His Pro Glu Glu Leu Val Leu Leu Gly His Ser Leu
Gly Ile Pro Trp Ala Pro Leu Ser Ser Cys Pro Ser
Gln Ala Leu Gln Leu Ala Gly Cys Leu Ser Gln Leu

TABLE 3-continued
PROTEIN SEQUENCES

His Ser Gly Leu Phe Leu Tyr Gln Gly Leu Leu Gln

Ala Leu Glu Gly Ile Ser pMON3492.Pep
(SEQ ID NO:50)
Met Ala Pro Ala Leu Gln Pro Thr Gln Gly Ala Met

Pro Ala Phe Ala Ser Ala Phe Gln Arg Arg Ala Gly

Gly Val Leu Val Ala Ser His Leu Gln Ser Phe Leu

Glu Val Ser Tyr Arg Val Leu Arg His Leu Ala Gln

Pro Thr Pro Leu Gly Pro Ala Ser Ser Leu Pro Gln

Ser Phe Leu Leu Lys Ser Leu Glu Gln Val Arg Lys

Ile Gln Gly Asp Gly Ala Ala Leu Gln Glu Lys Leu

Cys Ala Thr Tyr Lys Leu Cys His Pro Glu Glu Leu

Val Leu Leu Gly His Ser Leu Gly Ile Pro Trp Ala

Pro Leu Ser Ser Cys Pro Ser Gln Ala Leu Gln Leu

Ala Gly Cys Leu Ser Gln Leu His Ser Gly Leu Phe

Leu Tyr Gln Gly Leu Leu Gln Ala Leu Glu Gly Ile

Ser Pro Glu Leu Gly Pro Thr Leu Asp Thr Leu Gln

Leu Asp Val Ala Asp Phe Ala Thr Thr Ile Trp Gln

Gln Met Glu Glu Leu Gly pMON3493.Pep
(SEQ ID NO:51)
Thr Gln Gly Ala Met Pro Ala Phe Ala Ser Ala Phe

Gln Arg Arg Ala Gly Gly Val Leu Val Ala Ser His

Leu Gln Ser Phe Leu Glu Val Ser Tyr Arg Val Leu

Arg His Leu Ala Gln Pro Thr Pro Leu Gly Pro Ala

Ser Ser Leu Pro Gln Ser Phe Leu Leu Lys Ser Leu

Glu Gln Val Arg Lys Ile Gln Gly Asp Gly Ala Ala

Leu Gln Glu Lys Leu Cys Ala Thr Tyr Lys Leu Cys

His Pro Glu Glu Leu Val Leu Leu Gly His Ser Leu

Gly Ile Pro Trp Ala Pro Leu Ser Ser Cys Pro Ser

Gln Ala Leu Gln Leu Ala Gly Cys Leu Ser Gln Leu

His Ser Gly Leu Phe Leu Tyr Gln Gly Leu Leu Gln

Ala Leu Glu Gly Ile Ser Pro Glu Leu Gly Pro Thr

Leu Asp Thr Leu Gln Leu Asp Val Ala Asp Phe Ala

Thr Thr Ile Trp Gln Gln Met Glu Glu Leu Gly Met

Ala Pro Ala Leu Gln Pro pMON3494.Pep
(SEQ ID NO:52)
Ser Ala Phe Gln Arg Arg Ala Gly Gly Val Leu Val

Ala Ser His Leu Gln Ser Phe Leu Glu Val Ser Tyr

Arg Val Leu Arg His Leu Ala Gln Pro Thr Pro Leu

Gly Pro Ala Ser Ser Leu Pro Gln Ser Phe Leu Leu

Lys Ser Leu Glu Gln Val Arg Lys Ile Gln Gly Asp

Gly Ala Ala Leu Gln Glu Lys Leu Cys Ala Thr Tyr

Lys Leu Cys His Pro Glu Glu Leu Val Leu Leu Gly

His Ser Leu Gly Ile Pro Trp Ala Pro Leu Ser Ser

Cys Pro Ser Gln Ala Leu Gln Leu Ala Gly Cys Leu

Ser Gln Leu His Ser Gly Leu Phe Leu Tyr Gln Gly

Leu Leu Gln Ala Leu Glu Gly Ile Ser Pro Glu Leu

Gly Pro Thr Leu Asp Thr Leu Gln Leu Asp Val Ala

Asp Phe Ala Thr Thr Ile Trp Gln Gln Met Glu Glu

Leu Gly Met Ala Pro Ala Leu Gln Pro Thr Gln Gly

Ala Met Pro Ala Phe Ala pMON25181.pep
(SEQ ID NO:53)
Pro Glu Leu Gly Pro Thr Leu Asp Thr Leu Gln Leu Asp Val Ala Asp Phe Ala Thr Thr Ile Trp Gln Gln Met Glu Glu Leu Gly Met Ala Pro Ala Leu Gln Pro Thr Gln Gly Ala Met Pro Ala Phe Ala Ser Ala Phe Gln Arg Arg Ala Gly Gly Val Leu Val Ala Ser His Leu Gln Ser Phe Leu Glu Val Ser Tyr Arg Val Leu Arg His Leu Ala Gln Pro Thr Pro Leu Gly Pro Ala Ser Ser Leu Pro Gln Ser Phe Leu Leu Lys Ser Leu Glu Gln Val Arg Lys Ile Gln Gly Asp Gly Ala Ala Leu Gln Glu Lys Leu Cys Ala Thr Tyr Lys Leu Cys His Pro Glu Glu Leu Val Leu Leu Gly His Ser Leu Gly Ile Pro Trp Ala Pro Leu Ser Ser Cys Pro Ser Gln Ala Leu Gln Leu Ala Gly Cys Leu Ser Gln Leu His Ser Gly Leu Phe Leu Tyr Gln Gly Leu Leu Gln Ala Leu Glu Gly Ile Ser pMON25182.pep
(SEQ ID NO:54)
Met Ala Pro Ala Leu Gln Pro Thr Gln Gly Ala Met Pro Ala Phe Ala Ser Ala Phe Gln Arg Arg Ala Gly Gly Val Leu Val Ala Ser His Leu Gln Ser Phe Leu Glu Val Ser Tyr Arg Val Leu Arg His Leu Ala Gln Pro Thr Pro Leu Gly Pro Ala Ser Ser Leu Pro Gln Ser Phe Leu Leu Lys Ser Leu Glu Gln Val Arg Lys Ile Gln Gly Asp Gly Ala Ala Leu Gln Glu Lys Leu Cys Ala Thr Tyr Lys Leu Cys His Pro Glu Glu Leu

TABLE 3-continued
PROTEIN SEQUENCES

Val Leu Leu Gly His Ser Leu Gly Ile Pro Trp Ala

Pro Leu Ser Ser Cys Pro Ser Gln Ala Leu Gln Leu

Ala Gly Cys Leu Ser Gln Leu His Ser Gly Leu Phe

Leu Tyr Gln Gly Leu Leu Gln Ala Leu Glu Gly Ile

Ser Pro Glu Leu Gly Pro Thr Leu Asp Thr Leu Gln

Leu Asp Val Ala Asp Phe Ala Thr Thr Ile Trp Gln

Gln Met Glu Glu Leu Gly pMON25183.pep (SEQ ID NO:55)

Thr Gln Gly Ala Met Pro Ala Phe Ala Ser Ala Phe

Gln Arg Arg Ala Gly Gly Val Leu Val Ala Ser His

Leu Gln Ser Phe Leu Glu Val Ser Tyr Arg Val Leu

Arg His Leu Ala Gln Pro Thr Pro Leu Gly Pro Ala

Ser Ser Leu Pro Gln Ser Phe Leu Leu Lys Ser Leu

Glu Gln Val Arg Lys Ile Gln Gly Asp Gly Ala Ala

Leu Gln Glu Lys Leu Cys Ala Thr Tyr Lys Leu Cys

His Pro Glu Glu Leu Val Leu Leu Gly His Ser Leu

Gly Ile Pro Trp Ala Pro Leu Ser Ser Cys Pro Ser

Gln Ala Leu Gln Leu Ala Gly Cys Leu Ser Gln Leu

His Ser Gly Leu Phe Leu Tyr Gln Gly Leu Leu Gln

Ala Leu Glu Gly Ile Ser Pro Glu Leu Gly Pro Thr

Leu Asp Thr Leu Gln Leu Asp Val Ala Asp Phe Ala

Thr Thr Ile Trp Gln Gln Met Glu Glu Leu Gly Met

Ala Pro Ala Leu Gln Pro pMON25184.pep (SEQ ID NO:56)

Ser Ala Phe Gln Arg Arg Ala Gly Gly Val Leu Val

Ala Ser His Leu Gln Ser Phe Leu Glu Val Ser Tyr

Arg Val Leu Arg His Leu Ala Gln Pro Thr Pro Leu

Gly Pro Ala Ser Ser Leu Pro Gln Ser Phe Leu Leu

Lys Ser Leu Glu Gln Val Arg Lys Ile Gln Gly Asp

Gly Ala Ala Leu Gln Glu Lys Leu Cys Ala Thr Tyr

Lys Leu Cys His Pro Glu Glu Leu Val Leu Leu Gly

His Ser Leu Gly Ile Pro Trp Ala Pro Leu Ser Ser

Cys Pro Ser Gln Ala Leu Gln Leu Ala Gly Cys Leu

Ser Gln Leu His Ser Gly Leu Phe Leu Tyr Gln Gly

Leu Leu Gln Ala Leu Glu Gly Ile Ser Pro Glu Leu

Gly Pro Thr Leu Asp Thr Leu Gln Leu Asp Val Ala

Asp Phe Ala Thr Thr Ile Trp Gln Gln Met Glu Glu

Leu Gly Met Ala Pro Ala Leu Gln Pro Thr Gln Gly

Ala Met Pro Ala Phe Ala pMON25185.pep (SEQ ID NO:57)

Pro Glu Leu Gly Pro Thr Leu Asp Thr Leu Gln Leu

Asp Val Ala Asp Phe Ala Thr Thr Ile Trp Gln Gln

Met Glu Glu Leu Gly Met Ala Pro Ala Leu Gln Pro

Thr Gln Gly Ala Met Pro Ala Phe Ala Ser Ala Phe

Gln Arg Arg Ala Gly Gly Val Leu Val Ala Ser His

Leu Gln Ser Phe Leu Glu Val Ser Tyr Arg Val Leu

Arg His Leu Ala Gln Pro Ser Gly Gly Ser Gly Gly

Ser Gln Ser Phe Leu Leu Lys Ser Leu Glu Gln Val

Arg Lys Ile Gln Gly Asp Gly Ala Ala Leu Gln Glu

Lys Leu Cys Ala Thr Tyr Lys Leu Cys His Pro Glu

Glu Leu Val Leu Leu Gly His Ser Leu Gly Ile Pro

Trp Ala Pro Leu Ser Ser Cys Pro Ser Gln Ala Leu

Gln Leu Ala Gly Cys Leu Ser Gln Leu His Ser Gly

Leu Phe Leu Tyr Gln Gly Leu Leu Gln Ala Leu Glu

Gly Ile Ser pMON25186.pep (SEQ ID NO:58)

Met Ala Pro Ala Leu Gln Pro Thr Gln Gly Ala Met

Pro Ala Phe Ala Ser Ala Phe Gln Arg Arg Ala Gly

Gly Val Leu Val Ala Ser His Leu Gln Ser Phe Leu

Glu Val Ser Tyr Arg Val Leu Arg His Leu Ala Gln

Pro Ser Gly Gly Ser Gly Gly Ser Gln Ser Phe Leu

Leu Lys Ser Leu Glu Gln Val Arg Lys Ile Gln Gly

Asp Gly Ala Ala Leu Gln Glu Lys Ala Thr Tyr Lys

Leu Cys His Pro Glu Glu Leu Val Leu Leu Gly His

Ser Leu Gly Ile Pro Trp Ala Pro Leu Ser Ser Cys

Pro Ser Gln Ala Leu Gln Leu Ala Gly Cys Leu Ser

Gln Leu His Ser Gly Leu Phe Leu Tyr Gln Gly Leu

Leu Gln Ala Leu Glu Gly Ile Ser Pro Glu Leu Gly

Pro Thr Leu Asp Thr Leu Gln Leu Asp Val Ala Asp

Phe Ala Thr Thr Ile Trp Gln Gln Met Glu Glu Leu

Gly pMON25187.pep (SEQ ID NO:59)

Thr Gln Gly Ala Met Pro Ala Phe Ala Ser Ala Phe

Gln Arg Arg Ala Gly Gly Val Leu Val Ala Ser His

TABLE 3-continued

PROTEIN SEQUENCES

Leu Gln Ser Phe Leu Glu Val Ser Tyr Arg Val Leu
Arg His Leu Ala Gln Pro Ser Gly Gly Ser Gly Gly
Ser Gln Ser Phe Leu Leu Lys Ser Leu Glu Gln Val
Arg Lys Ile Gln Gly Asp Gly Ala Ala Leu Gln Glu
Lys Leu Cys Ala Thr Tyr Lys Leu Cys His Pro Glu
Glu Leu Val Leu Leu Gly His Ser Leu Gly Ile Pro
Trp Ala Pro Leu Ser Ser Cys Pro Ser Gln Ala Leu
Gln Leu Ala Gly Cys Leu Ser Gln Leu His Ser Gly
Leu Phe Leu Tyr Gln Gly Leu Leu Gln Ala Leu Glu
Gly Ile Ser Pro Glu Leu Gly Pro Thr Leu Asp Thr
Leu Gln Leu Asp Val Ala Asp Phe Ala Thr Thr Ile
Trp Gln Gln Met Glu Glu Leu Gly Met Ala Pro Ala
Leu Gln Pro pMON25188.pep                                (SEQ ID NO:60)
Ser Ala Phe Gln Arg Arg Ala Gly Gly Val Leu Val
Ala Ser His Leu Gln Ser Phe Leu Glu Val Ser Tyr
Arg Val Leu Arg His Leu Ala Gln Pro Ser Gly Gly
Ser Gly Gly Ser Gln Ser Phe Leu Leu Lys Ser Leu
Glu Gln Val Arg Lys Ile Gln Gly Asp Gly Ala Ala
Leu Gln Glu Lys Leu Cys Ala Thr Tyr Lys Leu Cys
His Pro Glu Glu Leu Val Leu Leu Gly His Ser Leu
Gly Ile Pro Trp Ala Pro Leu Ser Ser Cys Pro Ser
Gln Ala Leu Gln Leu Ala Gly Cys Leu Ser Gln Leu
His Ser Gly Leu Phe Leu Tyr Gln Gly Leu Leu Gln
Ala Leu Glu Gly Ile Ser Pro Glu Leu Gly Pro Thr
Leu Asp Thr Leu Gln Leu Asp Val Ala Asp Phe Ala
Thr Thr Ile Trp Gln Gln Met Glu Glu Leu Gly Met
Ala Pro Ala Leu Gln Pro Thr Gln Gly Ala Met Pro
Ala Phe Ala pMON3460.Pep                                 (SEQ ID NO:95)
Leu Leu Gly His Ser Leu Gly Ile Pro Trp Ala Pro
Leu Ser Ser Cys Pro Ser Gln Ala Leu Gln Leu Ala
Gly Cys Leu Ser Gln Leu His Ser Gly Leu Phe Leu
Tyr Gln Gly Leu Leu Gln Ala Leu Glu Gly Ile Ser
Pro Glu Leu Gly Pro Thr Leu Asp Thr Leu Gln Leu
Asp Val Ala Asp Phe Ala Thr Thr Ile Trp Gln Gln
Met Glu Glu Leu Gly Met Ala Pro Ala Leu Gln Pro
Thr Gln Gly Ala Met Pro Ala Phe Ala Ser Ala Phe Gln Arg Arg Ala Gly Gly Val Leu Val Ala Ser His
Leu Gln Ser Phe Leu Glu Val Ser Tyr Arg Val Leu
Arg His Leu Ala Gln Pro Thr Pro Leu Gly Pro Ala
Ser Ser Leu Pro Gln Ser Phe Leu Leu Lys Ser Leu
Glu Gln Val Arg Lys Ile Gln Gly Asp Gly Ala Ala
Leu Gln Glu Lys Leu Cys Ala Thr Tyr Lys Leu Cys
His Pro Glu Glu Leu Val pMON3461.Pep                                 (SEQ ID NO:96)
Gln Leu His Ser Gly Leu Phe Leu Tyr Gln Gly Leu
Leu Gln Ala Leu Glu Gly Ile Ser Pro Glu Leu Gly
Pro Thr Leu Asp Thr Leu Gln Leu Asp Val Ala Asp
Phe Ala Thr Thr Ile Trp Gln Gln Met Glu Glu Leu
Gly Met Ala Pro Ala Leu Gln Pro Thr Gln Gly Ala
Met Pro Ala Phe Ala Ser Ala Phe Gln Arg Arg Ala
Gly Gly Val Leu Val Ala Ser His Leu Gln Ser Phe
Leu Glu Val Ser Tyr Arg Val Leu Arg His Leu Ala
Gln Pro Thr Pro Leu Gly Pro Ala Ser Ser Leu Pro
Gln Ser Phe Leu Leu Lys Ser Leu Glu Gln Val Arg
Lys Ile Gln Gly Asp Gly Ala Ala Leu Gln Glu Lys
Leu Cys Ala Thr Tyr Lys Leu Cys His Pro Glu Glu
Leu Val Leu Leu Gly His Ser Leu Gly Ile Pro Trp
Ala Pro Leu Ser Ser Cys Pro Ser Gln Ala Leu Gln
Leu Ala Gly Cys Leu Ser 3462.Pep                                     (SEQ ID NO:97)
Leu Phe Leu Tyr Gln Gly Leu Leu Gln Ala Leu Glu
Gly Ile Ser Pro Glu Leu Gly Pro Thr Leu Asp Thr
Leu Gln Leu Asp Val Ala Asp Phe Ala Thr Thr Ile
Trp Gln Gln Met Glu Glu Leu Gly Met Ala Pro Ala
Leu Gln Pro Thr Gln Gly Ala Met Pro Ala Phe Ala
Ser Ala Phe Gln Arg Arg Ala Gly Gly Val Leu Val
Ala Ser His Leu Gln Ser Phe Leu Glu Val Ser Tyr
Arg Val Leu Arg His Leu Ala Gln Pro Thr Pro Leu
Gly Pro Ala Ser Ser Leu Pro Gln Ser Phe Leu Leu
Lys Ser Leu Glu Gln Val Arg Lys Ile Gln Gly Asp
Gly Ala Ala Leu Gln Glu Lys Leu Cys Ala Thr Tyr
Lys Leu Cys His Pro Glu Glu Leu Val Leu Leu Gly
His Ser Leu Gly Ile Pro Trp Ala Pro Leu Ser Ser

TABLE 3-continued

PROTEIN SEQUENCES

Cys Pro Ser Gln Ala Leu Gln Leu Ala Gly Cys Leu
Ser Gln Leu His Ser Gly

3463.Pep
(SEQ ID NO:98)
Leu Tyr Gln Gly Leu Leu Gln Ala Leu Glu Gly Ile
Ser Pro Glu Leu Gly Pro Thr Leu Asp Thr Leu Gln
Leu Asp Val Ala Asp Phe Ala Thr Thr Ile Trp Gln
Gln Met Glu Glu Leu Gly Met Ala Pro Ala Leu Gln
Pro Thr Gln Gly Ala Met Pro Ala Phe Ala Ser Ala
Phe Gln Arg Arg Ala Gly Gly Val Leu Val Ala Ser
His Leu Gln Ser Phe Leu Glu Val Ser Tyr Arg Val
Leu Arg His Leu Ala Gln Pro Thr Pro Leu Gly Pro
Ala Ser Ser Leu Pro Gln Ser Phe Leu Leu Lys Ser
Leu Glu Gln Val Arg Lys Ile Gln Gly Asp Gly Ala
Ala Leu Gln Glu Lys Leu Cys Ala Thr Tyr Lys Leu
Cys His Pro Glu Glu Leu Val Leu Leu Gly His Ser
Leu Gly Ile Pro Trp Ala Pro Leu Ser Ser Cys Pro
Ser Gln Ala Leu Gln Leu Ala Gly Cys Leu Ser Gln
Leu His Ser Gly Leu Phe

3464.Pep
(SEQ ID NO:99)
Ala Leu Glu Gly Ile Ser Pro Glu Leu Gly Pro Thr
Leu Asp Thr Leu Gln Leu Asp Val Ala Asp Phe Ala
Thr Thr Ile Trp Gln Gln Met Glu Glu Leu Gly Met
Ala Pro Ala Leu Gln Pro Thr Gln Gly Ala Met Pro
Ala Phe Ala Ser Ala Phe Gln Arg Arg Ala Gly Gly
Val Leu Val Ala Ser His Leu Gln Ser Phe Leu Glu
Val Ser Tyr Arg Val Leu Arg His Leu Ala Gln Pro
Thr Pro Leu Gly Pro Ala Ser Ser Leu Pro Gln Ser
Phe Leu Leu Lys Ser Leu Glu Gln Val Arg Lys Ile
Gln Gly Asp Gly Ala Ala Leu Gln Glu Lys Leu Cys
Ala Thr Tyr Lys Leu Cys His Pro Glu Glu Leu Val
Leu Leu Gly His Ser Leu Gly Ile Pro Trp Ala Pro
Leu Ser Ser Cys Pro Ser Gln Ala Leu Gln Leu Ala
Gly Cys Leu Ser Gln Leu His Ser Gly Leu Phe Leu
Tyr Gln Gly Leu Leu Gln

3465.Pep
(SEQ ID NO:100)
Asp Phe Ala Thr Thr Ile Trp Gln Gln Met Glu Glu
Leu Gly Met Ala Pro Ala Leu Gln Pro Thr Gln Gly

Ala Met Pro Ala Phe Ala Ser Ala Phe Gln Arg Arg
Ala Gly Gly Val Leu Val Ala Ser His Leu Gln Ser
Phe Leu Glu Val Ser Tyr Arg Val Leu Arg His Leu
Ala Gln Pro Thr Pro Leu Gly Pro Ala Ser Ser Leu
Pro Gln Ser Phe Leu Leu Lys Ser Leu Glu Gln Val
Arg Lys Ile Gln Gly Asp Gly Ala Ala Leu Gln Glu
Lys Leu Cys Ala Thr Tyr Lys Leu Cys His Pro Glu
Glu Leu Val Leu Leu Gly His Ser Leu Gly Ile Pro
Trp Ala Pro Leu Ser Ser Cys Pro Ser Gln Ala Leu
Gln Leu Ala Gly Cys Leu Ser Gln Leu His Ser Gly
Leu Phe Leu Tyr Gln Gly Leu Leu Gln Ala Leu Glu
Gly Ile Ser Pro Glu Leu Gly Pro Thr Leu Asp Thr
Leu Gln Leu Asp Val Ala

3466.Pep
(SEQ ID NO:101)
Ile Trp Gln Gln Met Glu Glu Leu Gly Met Ala Pro
Ala Leu Gln Pro Thr Gln Gly Ala Met Pro Ala Phe
Ala Ser Ala Phe Gln Arg Arg Ala Gly Gly Val Leu
Val Ala Ser His Leu Gln Ser Phe Leu Glu Val Ser
Tyr Arg Val Leu Arg His Leu Ala Gln Pro Thr Pro
Leu Gly Pro Ala Ser Ser Leu Pro Gln Ser Phe Leu
Leu Lys Ser Leu Glu Gln Val Arg Lys Ile Gln Gly
Asp Gly Ala Ala Leu Gln Glu Lys Leu Cys Ala Thr
Tyr Lys Leu Cys His Pro Glu Glu Leu Val Leu Leu
Gly His Ser Leu Gly Ile Pro Trp Ala Pro Leu Ser
Ser Cys Pro Ser Gln Ala Leu Gln Leu Ala Gly Cys
Leu Ser Gln Leu His Ser Gly Leu Phe Leu Tyr Gln
Gly Leu Leu Gln Ala Leu Glu Gly Ile Ser Pro Glu
Leu Gly Pro Thr Leu Asp Thr Leu Gln Leu Asp Val
Ala Asp Phe Ala Thr Thr

3467.Pep
(SEQ ID NO:102)
Gln Gln Met Glu Glu Leu Gly Met Ala Pro Ala Leu
Gln Pro Thr Gln Gly Ala Met Pro Ala Phe Ala Ser
Ala Phe Gln Arg Arg Ala Gly Gly Val Leu Val Ala
Ser His Leu Gln Ser Phe Leu Glu Val Ser Tyr Arg
Val Leu Arg His Leu Ala Gln Pro Thr Pro Leu Gly
Pro Ala Ser Ser Leu Pro Gln Ser Phe Leu Leu Lys
Ser Leu Glu Gln Val Arg Lys Ile Gln Gly Asp Gly
Ala Ala Leu Gln Glu Lys Leu Cys Ala Thr Tyr Lys

TABLE 3-continued
PROTEIN SEQUENCES

```
Leu Cys His Pro Glu Glu Leu Val Leu Leu Gly His

Ser Leu Gly Ile Pro Trp Ala Pro Leu Ser Ser Cys

Pro Ser Gln Ala Leu Gln Leu Ala Gly Cys Leu Ser

Gln Leu His Ser Gly Leu Phe Leu Tyr Gln Gly Leu

Leu Gln Ala Leu Glu Gly Ile Ser Pro Glu Leu Gly

Pro Thr Leu Asp Thr Leu Gln Leu Asp Val Ala Asp

Phe Ala Thr Thr Ile Trp
```

3499.Pep
(SEQ ID NO:103)
```
Leu Leu Gly His Ser Leu Gly Ile Pro Trp Ala Pro

Leu Ser Ser Cys Pro Ser Gln Ala Leu Gln Leu Ala

Gly Cys Leu Ser Gln Leu His Ser Gly Leu Phe Leu

Tyr Gln Gly Leu Leu Gln Ala Leu Glu Gly Ile Ser

Pro Glu Leu Gly Pro Thr Leu Asp Thr Leu Gln Leu

Asp Val Ala Asp Phe Ala Thr Thr Ile Trp Gln Gln

Met Glu Glu Leu Gly Met Ala Pro Ala Leu Gln Pro

Thr Gln Gly Ala Met Pro Ala Phe Ala Ser Ala Phe

Gln Arg Arg Ala Gly Gly Val Leu Val Ala Ser His

Leu Gln Ser Phe Leu Glu Val Ser Tyr Arg Val Leu

Arg His Leu Ala Gln Pro Thr Pro Leu Gly Pro Ala

Ser Ser Leu Pro Gln Ser Phe Leu Leu Lys Ser Leu

Glu Gln Val Arg Lys Ile Gln Gly Asp Gly Ala Ala

Leu Gln Glu Lys Leu Cys Ala Thr Tyr Lys Leu Cys

His Pro Glu Glu Leu Val
``` pG1110.pep
(SEQ ID NO:104)
GlnSerPheLeuLeuLysSerLeuGluGlnValArgLysIleGlnGly
AspGlyAlaAlaLeuGlnGluLysLeuCysAlaThrTyrLysLeuCys
HisProGluGluLeuValLeuLeuGlyHisSerLeuGlyIleProTrp
AlaProLeuSerSerCysProSerGlnAlaLeuGlnLeuAlaGlyCys
LeuSerGlnLeuHisSerGlyLeuPheLeuTyrGlnGlyLeuLeuGln
AlaLeuGluGlyIleSerProGluLeuGlyProThrLeuAspThrLeu
GlnLeuAspValAlaAspPheAlaThrThrIleTrpGlnGlnMetGlu
GluLeuGlyMetAlaProAlaLeuGlnProThrGlnGlyAlaMetPro
AlaPheAlaSerAlaPheGlnArgArgAlaGlyGlyValLeuValAla
SerHisLeuGlnSerPheLeuGluValSerTyrArgValLeuArgHis
LeuAlaGlnProAspMetAlaThrProLeuGlyProAlaSerSerLeu
Pro pG123122.pep
(SEQ ID NO:105)
GluLeuGlyMetAlaProAlaLeuGlnProThrGlnGlyAlaMetPro
AlaPheAlaSerAlaPheGlnArgArgAlaGlyGlyValLeuValAla
SerHisLeuGlnSerPheLeuGluValSerTyrArgValLeuArgHis
LeuAlaGlnProAspMetAlaThrProLeuGlyProAlaSerSerLeu
ProGlnSerPheLeuLeuLysSerLeuGluGlnValArgLysIleGln
GlyAspGlyAlaAlaLeuGlnGluLysLeuCysAlaThrTyrLysLeu
CysHisProGluGluLeuValLeuLeuGlyHisSerLeuGlyIlePro
TrpAlaProLeuSerSerCysProSerGlnAlaLeuGlnLeuAlaGly
CysLeuSerGlnLeuHisSerGlyLeuPheLeuTyrGlnGlyLeuLeu
GlnAlaLeuGluGlyIleSerProGluLeuGlyProThrLeuAspThr
LeuGlnLeuAspValAlaAspPheAlaThrThrIleTrpGlnGlnMet
Glu pG125124.pep
(SEQ ID NO:106)
GlyMetAlaProAlaLeuGlnProThrGlnGlyAlaMetProAlaPhe
AlaSerAlaPheGlnArgArgAlaGlyGlyValLeuValAlaSerHis
LeuGlnSerPheLeuGluValSerTyrArgValLeuArgHisLeuAla
GlnProAspMetAlaThrProLeuGlyProAlaSerSerLeuProGln
SerPheLeuLeuLysSerLeuGluGlnValArgLysIleGlnGlyAsp
GlyAlaAlaLeuGlnGluLysLeuCysAlaThrTyrLysLeuCysHis
ProGluGluLeuValLeuLeuGlyHisSerLeuGlyIleProTrpAla
ProLeuSerSerCysProSerGlnAlaLeuGlnLeuAlaGlyCysLeu
SerGlnLeuHisSerGlyLeuPheLeuTyrGlnGlyLeuLeuGlnAla
LeuGluGlyIleSerProGluLeuGlyProThrLeuAspThrLeuGln
LeuAspValAlaAspPheAlaThrThrIleTrpGlnGlnMetGluGlu
Leu pG1312.pep
(SEQ ID NO:107)
PheLeuLeuLysSerLeuGluGlnValArgLysIleGlnGlyAspGly
AlaAlaLeuGlnGluLysLeuCysAlaThrTyrLysLeuCysHisPro
GluGluLeuValLeuLeuGlyHisSerLeuGlyIleProTrpAlaPro
LeuSerSerCysProSerGlnAlaLeuGlnLeuAlaGlyCysLeuSer
GlnLeuHisSerGlyLeuPheLeuTyrGlnGlyLeuLeuGlnAlaLeu
GluGlyIleSerProGluLeuGlyProThrLeuAspThrLeuGlnLeu
AspValAlaAspPheAlaThrThrIleTrpGlnGlnMetGluGluLeu
GlyMetAlaProAlaLeuGlnProThrGlnGlyAlaMetProAlaPhe
AlaSerAlaPheGlnArgArgAlaGlyGlyValLeuValAlaSerHis
LeuGlnSerPheLeuGluValSerTyrArgValLeuArgHisLeuAla
GlnProAspMetAlaThrProLeuGlyProAlaSerSerLeuProGln TABLE 3-continued

PROTEIN SEQUENCES

Ser pG159158.pep (SEQ ID NO:108)
SerPheLeuGluValSerTyrArgValLeuArgHisLeuAlaGlnPro
AspMetAlaThrProLeuGlyProAlaSerSerLeuProGlnSerPhe
LeuLeuLysSerLeuGluGlnValArgLysIleGlnGlyAspGlyAla
AlaLeuGlnGluLysLeuCysAlaThrTyrLysLeuCysHisProGlu
GluLeuValLeuLeuGlyHisSerLeuGlyIleProTrpAlaProLeu
SerSerCysProSerGlnAlaLeuGlnLeuAlaGlyCysLeuSerGln
LeuHisSerGlyLeuPheLeuTyrGlnGlyLeuLeuGlnAlaLeuGlu
GlyIleSerProGluLeuGlyProThrLeuAspThrLeuGlnLeuAsp
ValAlaAspPheAlaThrThrIleTrpGlnGlnMetGluGluLeuGly
MetAlaProAlaLeuGlnProThrGlnGlyAlaMetProAlaPheAla
SerAlaPheGlnArgArgAlaGlyGlyValLeuValAlaSerHisLeu
Gln pG1918.pep (SEQ ID NO:109)
GluGlnValArgLysIleGlnGlyAspGlyAlaAlaLeuGlnGluLys
LeuCysAlaThrTyrLysLeuCysHisProGluGluLeuValLeuLeu
GlyHisSerLeuGlyIleProTrpAlaProLeuSerSerCysProSer
GlnAlaLeuGlnLeuAlaGlyCysLeuSerGlnLeuHisSerGlyLeu
PheLeuTyrGlnGlyLeuLeuGlnAlaLeuGluGlyIleSerProGlu
LeuGlyProThrLeuAspThrLeuGlnLeuAspValAlaAspPheAla
ThrThrIleTrpGlnGlnMetGluGluLeuGlyMetAlaProAlaLeu
GlnProThrGlnGlyAlaMetProAlaPheAlaSerAlaPheGlnArg
ArgAlaGlyGlyValLeuValAlaSerHisLeuGlnSerPheLeuGlu
ValSerTyrArgValLeuArgHisLeuAlaGlnProAspMetAlaThr
ProLeuGlyProAlaSerSerLeuProGlnSerPheLeuLeuLysSer
Leu pG32.pep (SEQ ID NO:110)
LeuGlyProAlaSerSerLeuProGlnSerPheLeuLeuLysSerLeu
GluGlnValArgLysIleGlnGlyAspGlyAlaAlaLeuGlnGluLys
LeuCysAlaThrTyrLysLeuCysHisProGluGluLeuValLeuLeu
GlyHisSerLeuGlyIleProTrpAlaProLeuSerSerCysProSer
GlnAlaLeuGlnLeuAlaGlyCysLeuSerGlnLeuHisSerGlyLeu
PheLeuTyrGlnGlyLeuLeuGlnAlaLeuGluGlyIleSerProGlu
LeuGlyProThrLeuAspThrLeuGlnLeuAspValAlaAspPheAla
ThrThrIleTrpGlnGlnMetGluGluLeuGlyMetAlaProAlaLeu
GlnProThrGlnGlyAlaMetProAlaPheAlaSerAlaPheGlnArg
ArgALaGlyGlyValLeuValAlaSerHisLeuGlnSerPheLeuGlu
ValSerTyrArgValLeuArgHisLeuAlaGlnProAspMetAlaThr
Pro pG4948.pep (SEQ ID NO:111)
LeuLeuGlyHisSerLeuGlyIleProTrpAlaProLeuSerSerCys
ProSerGlnAlaLeuGlnLeuAlaGlyCysLeuSerGlnLeuHisSer
GlyLeuPheLeuTyrGlnGlyLeuLeuGlnAlaLeuGluGlyIleSer
ProGluLeuGlyProThrLeuAspThrLeuGlnLeuAspValAlaAsp
PheAlaThrThrIleTrpGlnGlnMetGluGluLeuGlyMetAlaPro
AlaLeuGlnProThrGlnGlyAlaMetProAlaPheAlaSerAlaPhe
GlnArgArgAlaGlyGlyValLeuValAlaSerHisLeuGlnSerPhe
LeuGluValSerTyrArgValLeuArgHisLeuAlaGlnProAspMet
AlaThrProLeuGlyProAlaSerSerLeuProGlnSerPheLeuLeu
LysSerLeuGluGlnValArgLysIleGlnGlyAspGlyAlaAlaLeu
GlnGluLysLeuCysAlaThrTyrLysLeuCysHiSProGluGluLeu
Val pG6059.pep (SEQ ID NO:112)
ProLeuSerSerCysProSerGlnAlaLeuGlnLeuAlaGlyCysLeu
SerGlnLeuHisSerGlyLeuPheLeuTyrGlnGlyLeuLeuGlnAla
LeuGluGlyIleSerProGluLeuGlyProThrLeuAspThrLeuGln
LeuAspValAlaAspPheAlaThrThrIleTrpGlnGlnMetGluGlu
LeuGlyMetAlaProAlaLeuGlnProThrGlnGlyAlaMetProAla
PheAlaSerAlaPheGlnArgArgAlaGlyGlyValLeuValAlaSer
HisLeuGlnSerPheLeuGluValSerTyrArgValLeuArgHisLeu
AlaGlnProAspMetAlaThrProLeuGlyProAlaSerSerLeuPro
GlnSerPheLeuLeuLysSerLeuGluGlnValArgLysIleGlnGly
AspGlyAlaAlaLeuGlnGluLysLeuCysAlaThrTyrLysLeuCys
HisProGluGluLeuValLeuLeuGlyHisSerLeuGlyIleProTrp
Ala pG6766.pep (SEQ ID NO:113)
GlnAlaLeuGlnLeuAlaGlyCysLeuSerGlnLeuHisSerGlyLeu
PheLeuTyrGlnGlyLeuLeuGlnAlaLeuGluGlyIleSerProGlu
LeuGlyProThrLeuAspThrLeuGlnLeuAspValAlaAspPheAla
ThrThrIleTrpGlnGlnMetGluGluLeuGlyMetAlaProAlaLeu
GlnProThrGlnGlyAlaMetProAlaPheAlaSerAlaPheGlnArg
ArgAlaGlyGlyValLeuValAlaSerHisLeuGlnSerPheLeuGlu
ValSerTyrArgValLeuArgHisLeuAlaGlnProAspMetAlaThr

TABLE 3-continued

PROTEIN SEQUENCES

ProLeuGlyProAlaSerSerLeuProGlnSerPheLeuLeuLysSer

LeuGluGlnValArgLysIleGlnGlyAspGlyAlaAlaLeuGlnGlu

LysLeuCysAlaThrTyrLysLeuCysHisProGluGluLeuValLeu

LeuGlyHisSerLeuGlyIleProTrpAlaProLeuSerSerCysPro

Ser pG6968.pep (SEQ ID NO:114)

LeuGlnLeuAlaGlyCysLeuSerGlnLeuHisSerGlyLeuPheLeu

TyrGlnGlyLeuLeuGlnAlaLeuGluGlyIleSerProGluLeuGly

ProThrLeuAspThrLeuGlnLeuAspValAlaAspPheAlaThrThr

IleTrpGlnGlnMetGluGluLeuGlyMetAlaProAlaLeuGlnPro

ThrGlnGlyAlaMetProAlaPheAlaSerAlaPheGlnArgArgAla

GlyGlyValLeuValAlaSerHisLeuGlnSerPheLeuGluValSer

TyrArgValLeuArgHisLeuAlaGlnProAspMetAlaThrProLeu

GlyProAlaSerSerLeuProGlnSerPheLeuLeuLysSerLeuGlu

GlnValArgLysIleGlnGlyAspGlyAlaAlaLeuGlnGluLysLeu

CysAlaThrTyrLysLeuCysHisProGluGluLeuValLeuLeuGly

HisSerLeuGlyIleProTrpAlaProLeuSerSerCysProSerGln

Ala pG7170.pep (SEQ ID NO:115)

LeuAlaGlyCysLeuSerGlnLeuHisSerGlyLeuPheLeuTyrGln

GlyLeuLeuGlnAlaLeuGluGlyIleSerProGluLeuGlyProThr

LeuAspThrLeuGlnLeuAspValAlaAspPheAlaThrThrIleTrp

GlnGlnMetGluGluLeuGlyMetAlaProAlaLeuGlnProThrGln

GlyAlaMetProAlaPheAlaSerAlaPheGlnArgArgAlaGlyGly

ValLeuValAlaSerHisLeuGlnSerPheLeuGluValSerTyrArg

ValLeuArgHisLeuAlaGlnProAspMetAlaThrProLeuGlyPro

AlaSerSerLeuProGlnSerPheLeuLeuLysSerLeuGluGlnVal

ArgLysIleGlnGlyAspGlyAlaAlaLeuGlnGluLysLeuCysAla

ThrTyrLysLeuCysHisProGluGluLeuValLeuLeuGlyHisSer

LeuGlyIleProTrpAlaProLeuSerSerCysProSerGlnAlaLeu

Gln p170169.pep (SEQ ID NO:128)

1  His Leu Ala Gln Pro Asp Met Ala Thr Pro Leu Gly
   Pro Ala Ser

16 Ser Leu Pro Gln Ser Phe Leu Leu Lys Ser Leu Glu
   Gln Val Arg

31 Lys Ile Gln Gly Asp Gly Ala Ala Leu Gln Glu Lys
   Leu Cys Ala

46 Thr Tyr Lys Leu Cys His Pro Glu Glu Leu Val Leu

TABLE 3-continued

PROTEIN SEQUENCES

Leu Gly His

61  Ser Leu Gly Ile Pro Trp Ala Pro Leu Ser Ser Cys
    Pro Ser Gln

76  Ala Leu Gln Leu Ala Gly Cys Leu Ser Gln Leu His
    Ser Gly Leu

91  Phe Leu Tyr Gln Gly Leu Leu Gln Ala Leu Glu Gly
    Ile Ser Pro

106 Glu Leu Gly Pro Thr Leu Asp Thr Leu Gln Leu Asp
    Val Ala Asp

121 Phe Ala Thr Thr Ile Trp Gln Gln Met Glu Glu Leu
    Gly Met Ala

136 Pro Ala Leu Gln Pro Thr Gln Gly Ala Met Pro Ala
    Phe Ala Ser

151 Ala Phe Gln Arg Arg Ala Gly Gly Val Leu Val Ala
    Ser His Leu

155 Gln Ser Phe Leu Glu Val Ser Tyr Arg Val Leu Arg

Materials and Methods

Recombinant DNA Methods

Unless noted otherwise, all specialty chemicals were obtained from Sigma Co., (St. Louis, Mo.). Restriction endonucleases and T4 DNA ligase were obtained from New England Biolabs (Beverly, Mass.) or Boehringer Mannheim (Indianapolis, Ind.).

Transformation of *E. coli* Strains

*E. coli* strains, such as DH5α™ (Life Technologies, Gaithersburg, Md.) and TG1 (Amersham Corp., Arlington Heights, Ill.) are used for transformation of ligation reactions and are the source of plasmid DNA for transfecting mammalian cells. *E. coli* strains, such as MON105 and JM101, can be used for expressing the G-CSF receptor agonist of the present invention in the cytoplasm or periplasmic space.

MON105 ATCC#55204: F-, lamda-,IN(rrnD, rrE)1, rpoD+, rpoH358

DH5α™: F-, phi80dlacZdeltaM15, delta(lacZYA-argF) U169, deoR, recA1, endA1, hsdR17(rk-,mk+), phoA, supE44lamda-, thi-1, gyrA96, relA1

TG1: delta(lac-pro), supE, thi-1, hsdD5/F' (traD36, proA+ B+, lacIq, lacZdeltaM15)

DH5α™ Subcloning efficiency cells are purchased as competent cells and are ready for transformation using the manufacturer's protocol, while both *E. coli* strains TG1 and MON105 are rendered competent to take up DNA using a CaCl$_2$ method. Typically, 20 to 50 mL of cells are grown in LB medium (1% Bacto-tryptone, 0.5% Bacto-yeast extract, 150 mM NaCl) to a density of approximately 1.0 optical density unit at 600 nanometers (OD600) as measured by a Baush & Lomb Spectronic spectrophotometer (Rochester, N.Y.). The cells are collected by centrifugation and resuspended in one-fifth culture volume of CaCl$_2$ solution (50 mM CaCl$_2$, 10 mM Tris-Cl, pH7.4) and are held at 4° C. for 30 minutes. The cells are again collected by centrifugation and resuspended in one-tenth culture volume of CaCl$_2$ solution. Ligated DNA is added to 0.2 mL of these cells, and the samples are held at 4° C. for 1 hour. The samples are shifted to 42° C. for two minutes and 1 mL of LB is added prior to shaking the samples at 37° C. for one hour. Cells from these samples are spread on plates (LB medium plus 1.5% Bacto-agar) containing either ampicillin (100 micrograms/mL, ug/mL) when selecting for ampicillin-resistant transformants, or spectinomycin (75 ug/mL) when selecting for spectinomycin-resistant transformants. The plates are incubated overnight at 37° C. Single colonies are picked, grown in LB supplemented with appropriate antibiotic for 6–16 hours at 37° C. with shaking. Colonies are picked and inoculated into LB plus appropriate antibiotic (100 ug/mL ampicillin or 75 ug/mL spectinomycin) and are grown at 37° C. while shaking. Before harvesting the cultures, 1 ul of cells are analyzed by PCR for the presence of a G-CSF gene. The PCR is carried out using a combination of primers that anneal to the G-CSF gene and/or vector. After the PCR is complete, loading dye is added to the sample followed by electrophoresis as described earlier. A gene has been ligated to the vector when a PCR product of the expected size is observed.

Methods for Creation of Genes with New N-terminus/C-terminus

Method I. Creation of genes with new N-terminus/C-terminus which contain a linker region.

Figure 2:
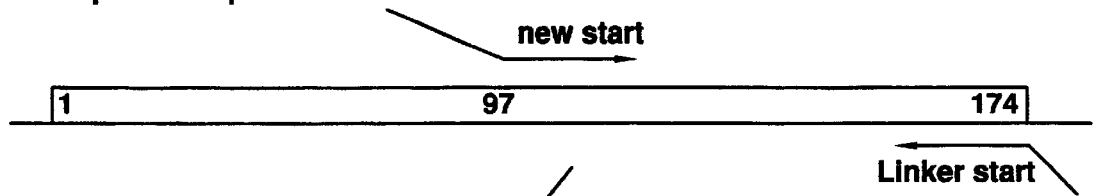
FIG. 2 shows a schematic of Method I, for creating new proteins in which the original N-terminus and C-terminus of the native protein are joined with a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to the amino acid 11 (a.a. 1–10 are deleted) through a linker region and a new C-terminus created at amino acid 96 of the original sequence.
Figure 2:
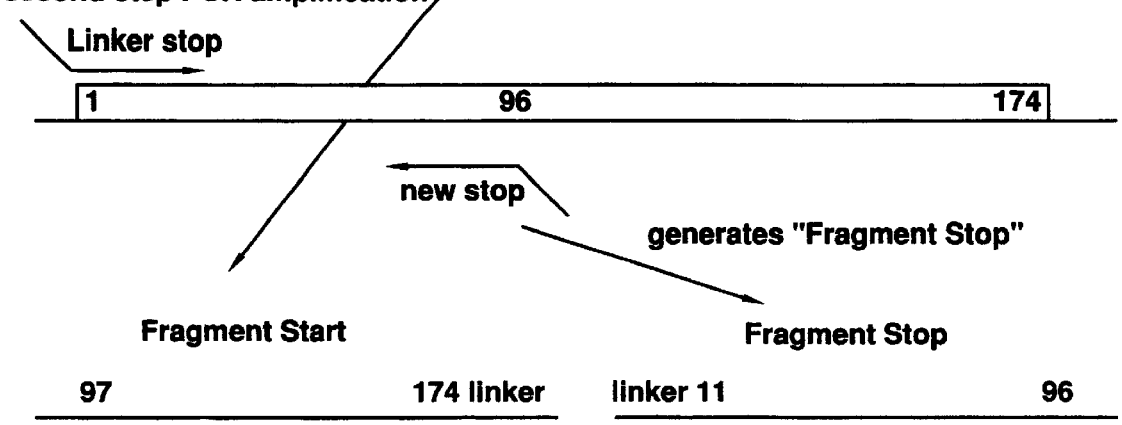
Figure 2:
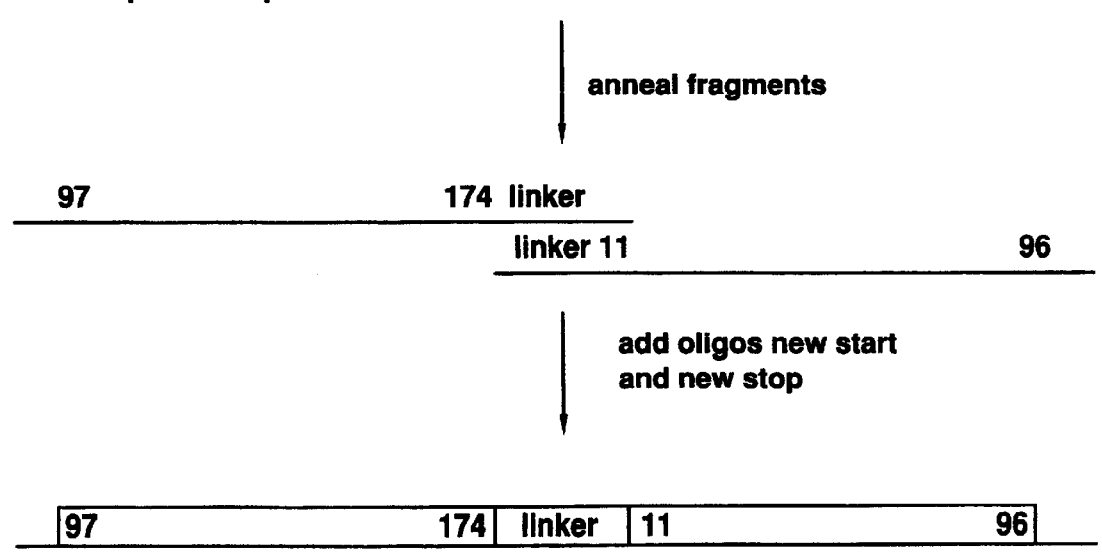

Genes with new N-terminus/C-terminus which contain a linker region separating the original C-terminus and N-terminus can be made essentially following the method described in L. S. Mullins, et al *J. Am. Chem. Soc.* 116, 5529–5533 (1994). Multiple steps of polymerase chain reaction (PCR) amplifications are used to rearrange the DNA sequence encoding the primary amino acid sequence of the protein. The steps are illustrated in FIG. 2.

In the first step, the primer set ("new start" and "linker start") is used to create and amplify, from the original gene sequence, the DNA fragment ("Fragment Start") that contains the sequence encoding the new N-terminal portion of the new protein followed by the linker that connects the C-terminal and N-terminal ends of the original protein. In the second step, the primer set ("new stop" and "linker stop") is used to create and amplify, from the original gene sequence, the DNA fragment ("Fragment Stop") that encodes the same linker as used above, followed by the new C-terminal portion of the new protein. The "new start" and "new stop" primers are designed to include the appropriate restriction enzyme recognition sites which allow cloning of the new gene into expression plasmids. Typical PCR conditions are one cycle 95° C. melting for two minutes; 25 cycles 94° C. denaturation for one minute, 50° C. annealing for one minute and 72° C. extension for one minute; plus one cycle 72° C. extension for seven minutes. A Perkin Elmer GeneAmp PCR Core Reagents kit is used. A 100 ul reaction contains 100 pmole of each primer and one ug of template DNA; and 1×PCR buffer, 200 uM dGTP, 200 uM DATP, 200 uM dTTP, 200 uM dCTP, 2.5 units AmpliTaq DNA polymerase and 2 mM $MgCl_2$. PCR reactions are performed in a Model 480 DNA thermal cycler (Perkin Elmer Corporation, Norwalk, Conn.).

"Fragment Start" and "Fragment Stop", which have complementary sequence in the linker region and the coding sequence for the two amino acids on both sides of the linker, are joined together in a third PCR step to make the full-length gene encoding the new protein. The DNA fragments "Fragment Start" and "Fragment Stop" are resolved on a 1% TAE gel, stained with ethidium bromide and isolated using a Qiaex Gel Extraction kit (Qiagen). These fragments are combined in equimolar quantities, heated at 70° C. for ten minutes and slow cooled to allow annealing through their shared sequence in "linker start" and "linker stop". In the third PCR step, primers "new start" and "new stop" are added to the annealed fragments to create and amplify the full-length new N-terminus/C-terminus gene. Typical PCR conditions are one cycle 95° C. melting for two minutes; 25 cycles 94° C. denaturation for one minute, 60° C. annealing for one minute and 72° C. extension for one minute; plus one cycle 72° C. extension for seven minutes. A Perkin Elmer GeneAmp PCR Core Reagents kit is used. A 100 ul reaction contains 100 pmole of each primer and approximately 0.5 ug of DNA; and 1×PCR buffer, 200 uM dGTP, 200 uM dATP, 200 uM dTTP, 200 uM dCTP, 2.5 units AmpliTaq DNA polymerase and 2 mM $MgCl_2$. PCR reactions are purified using a Wizard PCR Preps kit (Promega).

Method II. Creation of genes with new N-terminus/C-terminus without a linker region.

Figure 3:
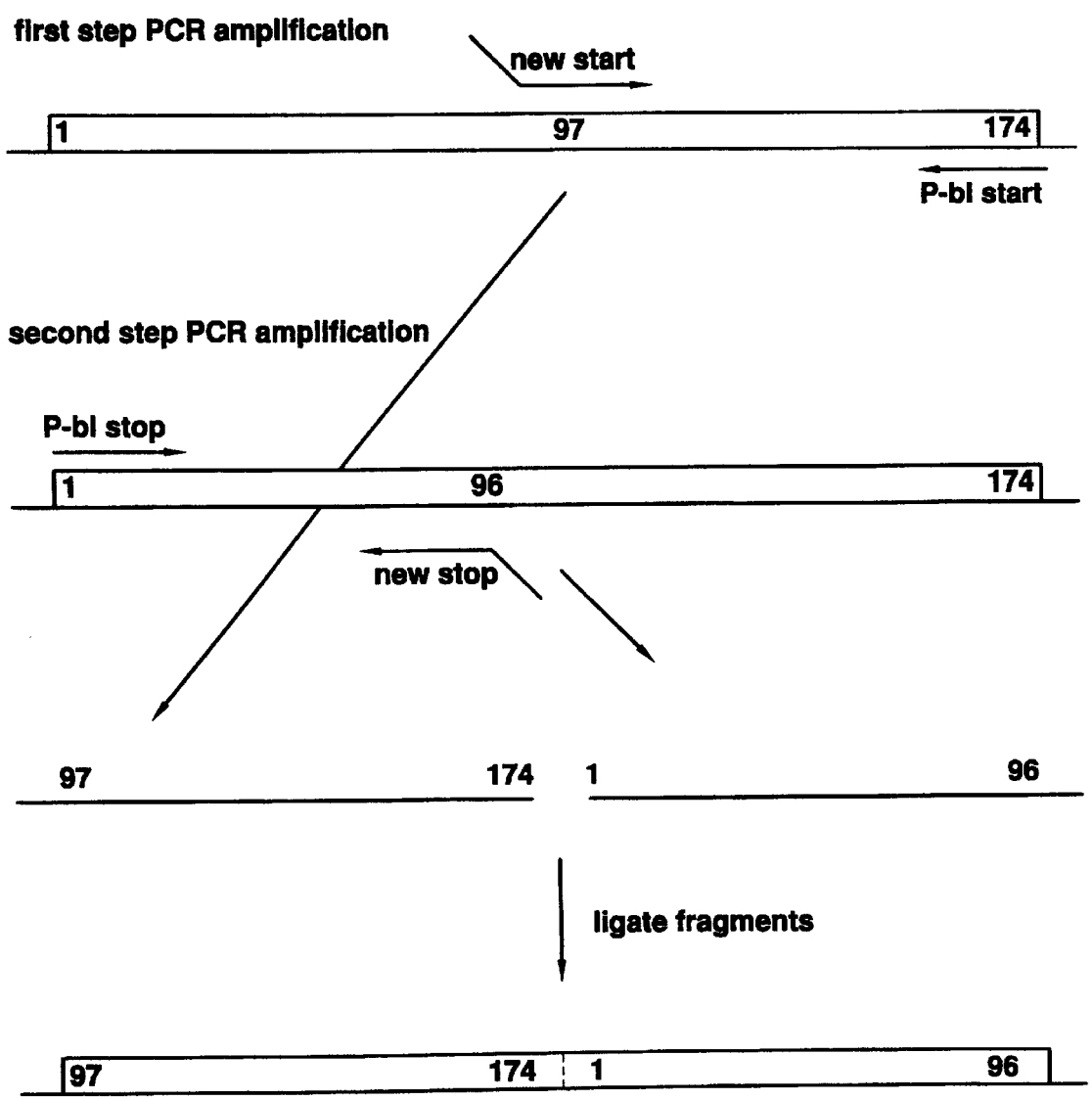
FIG. 3 shows a schematic of Method II, for creating new proteins in which the original N-terminus and C-terminus of the native protein are joined without a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to the original N-terminus and a new C-terminus created at amino acid 96 of the original sequence.

New N-terminus/C-terminus genes without a linker joining the original N-terminus and C-terminus can be made using two steps of PCR amplification and a blunt end ligation. The steps are illustrated in FIG. 3. In the first step, the primer set ("new start" and "P-bl start") is used to create and amplify, from the original gene sequence, the DNA fragment ("Fragment Start") that contains the sequence encoding the new N-terminal portion of the new protein. In the second step, the primer set ("new stop" and "P-bl stop") is used to create and amplify, from the original gene sequence, the DNA fragment ("Fragment Stop") that contains the sequence encoding the new C-terminal portion of the new protein. The "new start" and "new stop" primers are designed to include appropriate restriction sites which allow cloning of the new gene into expression vectors. Typical PCR conditions are one cycle 95° C. melting for two minutes; 25 cycles 94° C. denaturation for one minute, 50° C. annealing for 45 seconds and 72° C. extension for 45 seconds. Deep Vent polymerase (New England Biolabs) is used to reduce the occurrence of overhangs in conditions recommended by the manufacturer. The "P-bl start" and "P-bl stop" primers are phosphorylated at the 5' end to aid in the subsequent blunt end ligation of "Fragment Start" and "Fragment Stop" to each other. A 100 ul reaction contained 150 pmole of each primer and one ug of template DNA; and 1×Vent buffer (New England Biolabs), 300 uM dGTP, 300 uM DATP, 300 uM dTTP, 300 uM dCTP, and 1 unit Deep Vent polymerase. PCR reactions are performed in a Model 480 DNA thermal cycler (Perkin Elmer Corporation, Norwalk, Conn.). PCR reaction products are purified using a Wizard PCR Preps kit (Promega).

The primers are designed to include appropriate restriction enzyme recognition sites which allow for the cloning of the new gene into expression vectors. Typically "Fragment Start" is designed to create a NcoI restriction site, and "Fragment Stop" is designed to create a HindIII restriction site. Restriction digest reactions are purified using a Magic DNA Clean-up System kit (Promega). Fragments Start and Stop are resolved on a 1% TAE gel, stained with ethidium bromide and isolated using a Qiaex Gel Extraction kit (Qiagen). These fragments are combined with and annealed to the ends of the ~3800 base pair NcoI/HindIII vector fragment of pMON3934 by heating at 50° C. for ten minutes and allowed to slow cool. The three fragments are ligated together using T4 DNA ligase (Boehringer Mannheim). The result is a plasmid containing the full-length new N-terminus/C-terminus gene. A portion of the ligation reaction is used to transform *E. coli* strain DH5αcells (Life Technologies, Gaithersburg, Md.). Plasmid DNA is purified and sequence confirmed as below.

Method III. Creation of new N-terminus/C-terminus genes by tandem-duplication method New N-terminus/C-terminus genes can be made based on the method described in R. A. Horlick, et al *Protein Eng.*

Figure 4:
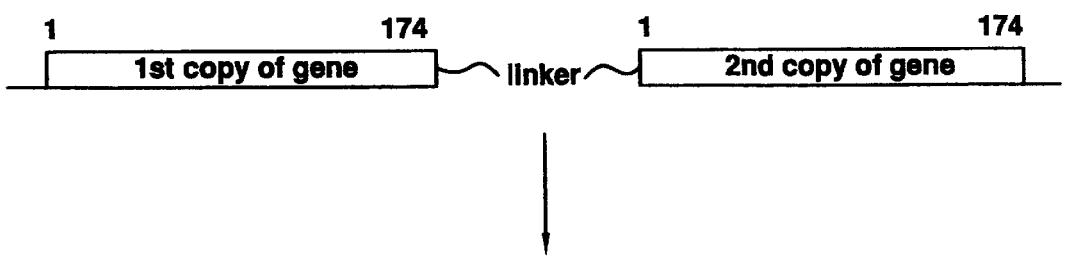
FIG. 4 shows a schematic of Method III, for creating new proteins in which the original N-terminus and C-terminus of the native protein are joined with a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to amino acid 1 through a linker region and a new C-terminus created at amino acid 96 of the original sequence.
Figure 4:
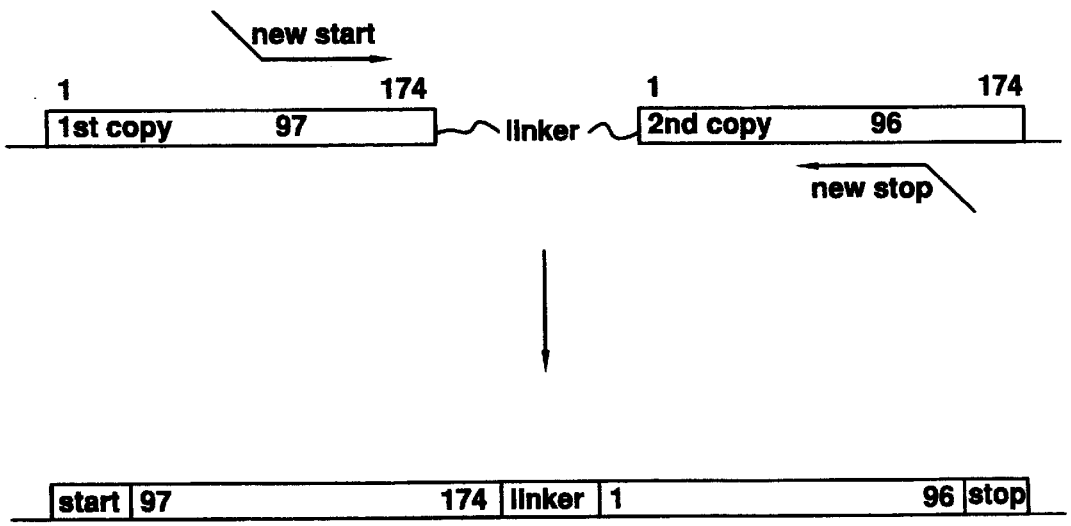

5:427–431 (1992). Polymerase chain reaction (PCR) amplification of the new N-terminus/C-terminus genes is performed using a tandemly duplicated template DNA. The steps are illustrated in FIG. 4.

The tandemly-duplicated template DNA is created by cloning and contains two copies of the gene separated by DNA sequence encoding a linker connecting the original C- and N-terminal ends of the two copies of the gene. Specific primer sets are used to create and amplify a full-length new N terminus/C-terminus gene from the tandemly-duplicated template DNA. These primers are designed to include appropriate restriction sites which allow for the cloning of the new gene into expression vectors. Typical PCR conditions are one cycle 95° C. melting for two minutes; 25 cycles 94° C. denaturation for one minute, 50° C. annealing for one minute and 72° C. extension for one minute; plus one cycle 72° C. extension for seven minutes. A Perkin Elmer Gene-Amp PCR Core Reagents kit (Perkin Elmer Corporation, Norwalk, Conn.) is used. A 100 ul reaction contains 100 pmole of each primer and one ug of template DNA; and 1×PCR buffer, 200 uM dGTP, 200 uM DATP, 200 uM dTTP, 200 uM dCTP, 2.5 units AmpliTaq DNA polymerase and 2 mM $MgCl_2$. PCR reactions are performed in a Model 480 DNA thermal cycler (Perkin Elmer Corporation, Norwalk, Conn.). PCR reactions are purified using a Wizard PCR Preps kit (Promega).

DNA Isolation and Characterization

Plasmid DNA can be isolated by a number of different methods and using commercially available kits known to those skilled in the art. A few such methods are shown herein. Plasmid DNA is isolated using the Promega Wizard™ Miniprep kit (Madison, Wis.), the Qiagen QIAwell Plasmid isolation kits (Chatsworth, Calif.) or Qiagen Plasmid Midi kit. These kits follow the same general procedure for plasmid DNA isolation. Briefly, cells are pelleted by centrifugation (5000×g), plasmid DNA released with sequential NaOH/acid treatment, and cellular debris is removed by centrifugation (10000×g). The supernatant (containing the plasmid DNA) is loaded onto a column containing a DNA-binding resin, the column is washed, and plasmid DNA eluted with TE. After screening for the colonies with the plasmid of interest, the E. coli cells are inoculated into 50–100 mLs of LB plus appropriate antibiotic for overnight growth at 37° C. in an air incubator while shaking. The purified plasmid DNA is used for DNA sequencing, further restriction enzyme digestion, additional subcloning of DNA fragments and transfection into mammalian, E. coli or other cells.

Sequence Confirmation

Purified plasmid DNA is resuspended in $dH_2O$ and quantitated by measuring the absorbance at 260/280 nm in a Bausch and Lomb Spectronic 601 UV spectrometer. DNA samples are sequenced using ABI PRISM™ DyeDeoxy™ terminator sequencing chemistry (Applied Biosystems Division of Perkin Elmer Corporation, Lincoln City, Calif.) kits (Part Number 401388 or 402078) according to the manufacturers suggested protocol usually modified by the addition of 5% DMSO to the sequencing mixture. Sequencing reactions are performed in a Model 480 DNA thermal cycler (Perkin Elmer Corporation, Norwalk, Conn.) following the recommended amplification conditions. Samples are purified to remove excess dye terminators with Centri-Sep™ spin columns (Princeton Separations, Adelphia, N.J.) and lyophilized. Fluorescent dye labeled sequencing reactions are resuspended in deionized formamide, and sequenced on denaturing 4.75% polyacrylamide-8M urea gels using an ABI Model 373A automated DNA sequencer. Overlapping DNA sequence fragments are analyzed and assembled into master DNA contigs using Sequencher v2.1 DNA analysis software (Gene Codes Corporation, Ann Arbor, Mich.).

Expression of G-CSF Receptor Agonists in Mammalian Cells

Mammalian Cell Transfection/Production of Conditioned Media

The BHK-21 cell line can be obtained from the ATCC 10801 University Boulevard, Manassas, Va. 20110-2209. The cells are cultured in Dulbecco's modified Eagle media (DMEM/high-glucose), supplemented to 2 mM (mM) L-glutamine and 10% fetal bovine serum (FBS). This formulation is designated BHK growth media. Selective media is BHK growth media supplemented with 453 units/mL hygromycin B (Calbiochem, San Diego, Calif.). The BHK-21 cell line was previously stably transfected with the HSV transactivating protein VP16, which transactivates the IE110 promoter found on the plasmid pMON3359 (See Hippenmeyer et al., *Bio/Technology*, pp.1037–1041, 1993). The VP16 protein drives expression of genes inserted behind the IE110 promoter. BHK-21 cells expressing the transactivating protein VP16 are designated BHK-VP16. The plasmid pMON1118 (See Highkin et al., *Poultry Sci.*, 70: 970–981, 1991) expresses the hygromycin resistance gene from the SV40 promoter. A similar plasmid is available from ATCC, pSV2-hph.

BHK-VP16 cells are seeded into a 60 millimeter (mm) tissue culture dish at $3 \times 10^5$ cells per dish 24 hours prior to transfection. Cells are transfected for 16 hours in 3 mL of "OPTIMEM"™ (Gibco-BRL, Gaithersburg, Md.) containing 10 ug of plasmid DNA containing the gene of interest, 3 ug hygromycin resistance plasmid, pMON1118, and 80 ug of Gibco-BRL "LIPOFECTAMINE"™ per dish. The media is subsequently aspirated and replaced with 3 mL of growth media. At 48 hours post-transfection, media from each dish is collected and assayed for activity (transient conditioned media). The cells are removed from the dish by trypsin-EDTA, diluted 1:10 and transferred to 100 mm tissue culture dishes containing 10 mL of selective media. After approximately 7 days in selective media, resistant cells grow into colonies several millimeters in diameter. The colonies are removed from the dish with filter paper (cut to approximately the same size as the colonies and soaked in trypsin/EDTA) and transferred to individual wells of a 24 well plate containing 1 mL of selective media. After the clones are grown to confluence, the conditioned media is re-assayed, and positive clones are expanded into growth media.

Expression of G-CSF Receptor Agonists in E. coli

E. coli strain MON105 or JM101 harboring the plasmid of interest are grown at 37° C. in M9 plus casamino acids medium with shaking in a air incubator Model G25 from New Brunswick Scientific (Edison, N.J.). Growth is monitored at OD600 until it reaches a value of 1, at which time nalidixic acid (10 milligrams/mL) in 0.1 N NaOH is added to a final concentration of 50 $\mu g/mL$. The cultures are then shaken at 37° C. for three to four additional hours. A high degree of aeration is maintained throughout culture period in order to achieve maximal production of the desired gene product. The cells are examined under a light microscope for the presence of inclusion bodies (IB). One mL aliquots of the culture are removed for analysis of protein content by boiling the pelleted cells, treating them with reducing buffer and electrophoresis via SDS-PAGE (see Maniatis et al. Molecular Cloning: A Laboratory Manual, 1982). The culture is centrifuged (5000×g) to pellet the cells.

Inclusion Body Preparation, Extraction, Refolding, Dialysis, DEAE Chromatography, and Characterization of the G-CSF Receptor Agonists which Accumulate as Inclusion Bodies in E. coli Isolation of Inclusion Bodies The cell pellet from a 330 mL E. coli culture is resuspended in 15 mL of sonication buffer (10 mM 2-amino-2-(hydroxymethyl) 1,3-propanediol hydrochloride (Tris-HCl), pH 8.0+1 mM ethylenediaminetetraacetic acid (EDTA)). These resuspended cells are sonicated using the microtip probe of a Sonicator Cell Disrupter (Model W-375, Heat Systems-Ultrasonics, Inc., Farmingdale, N.Y.). Three rounds of sonication in sonication buffer followed by centrifugation are employed to disrupt the cells and wash the inclusion bodies (IB). The first round of sonication is a 3 minute burst followed by a 1 minute burst, and the final two rounds of sonication are for 1 minute each.

Extraction and Refolding of Proteins from Inclusion Body Pellets

Following the final centrifugation step, the IB pellet is resuspended in 10 mL of 50 mM Tris-HCl, pH 9.5, 8 M urea and 5 mM dithiothreitol (DTT) and stirred at room temperature for approximately 45 minutes to allow for denaturation of the expressed protein.

The extraction solution is transferred to a beaker containing 70 mL of 5mM Tris-HCl, pH 9.5 and 2.3 M urea and gently stirred while exposed to air at 4° C. for 18 to 48 hours to allow the proteins to refold. Refolding is monitored by analysis on a Vydac (Hesperia, Calif.) C18 reversed phase high pressure liquid chromatography (RP-HPLC) column (0.46×25 cm). A linear gradient of 40% to 65% acetonitrile, containing 0.1% trifluoroacetic acid (TFA), is employed to monitor the refold. This gradient is developed over 30 minutes at a flow rate of 1.5 mL per minute. Denatured proteins generally elute later in the gradient than the refolded proteins.

Purification

Following the refold, contaminating E. coli proteins are removed by acid precipitation. The pH of the refold solution is titrated to between pH 5.0 and pH 5.2 using 15% (v/v) acetic acid (HOAc). This solution is stirred at 4° C. for 2 hours and then centrifuged for 20 minutes at 12,000×g to pellet any insoluble protein.

The supernatant from the acid precipitation step is dialyzed using a Spectra/Por 3 membrane with a molecular weight cut off (MWCO) of 3,500 daltons. The dialysis is against 2 changes of 4 liters (a 50-fold excess) of 10 mM Tris-HCl, pH 8.0 for a total of 18 hours. Dialysis lowers the sample conductivity and removes urea prior to DEAE chromatography. The sample is then centrifuged (20 minutes at 12,000×g) to pellet any insoluble protein following dialysis.

A Bio-Rad Bio-Scale DEAE2 column (7×52 mm) is used for ion exchange chromatography. The column is equilibrated in a buffer containing 10 mM Tris-HCl, pH 8.0. The protein is eluted using a 0-to-500 mM sodium chloride (NaCl) gradient, in equilibration buffer, over 45 column volumes. A flow rate of 1 mL per minute is used throughout the run. Column fractions (2 mL per fraction) are collected across the gradient and analyzed by RP HPLC on a Vydac (Hesperia, Calif.) C18 column (0.46×25 cm). A linear gradient of 40% to 65% acetonitrile, containing 0.1% trifluoroacetic acid (TFA), is employed. This gradient is developed over 30 minutes at a flow rate of 1.5 mL per minute. Pooled fractions are then dialyzed against 2 changes of 4 liters (50-to-500-fold excess) of 10 mM ammonium acetate ($NH_4Ac$), pH 4.0 for a total of 18 hours. Dialysis is performed using a Spectra/Por 3 membrane with a MWCO of 3,500 daltons. Finally, the sample is sterile filtered using a 0.22 μm syringe filter (μStar LB syringe filter, Costar, Cambridge, Mass.), and stored at 4° C.

In some cases the folded proteins can be affinity purified using affinity reagents such as mAbs or receptor subunits attached to a suitable matrix. Alternatively, (or in addition) purification can be accomplished using any of a variety of chromatographic methods such as: ion exchange, gel filtration or hydrophobic chromatography or reversed phase HPLC.

These and other protein purification methods are described in detail in Methods in Enzymology, Volume 182 'Guide to Protein Purification' edited by Murray Deutscher, Academic Press, San Diego, Calif. (1990).

Protein Characterization

The purified protein is analyzed by RP-HPLC, electrospray mass spectrometry, and SDS-PAGE. The protein quantitation is done by amino acid composition, RP-HPLC, and Bradford protein determination. In some cases tryptic peptide mapping is performed in conjunction with electrospray mass spectrometry to confirm the identity of the protein.

AML Proliferation Assay

The factor-dependent cell line AML 193 was obtained from the American Type Culture Collection (ATCC, Rockville, Md.). This cell line, established from a patient with acute myelogenous leukemia, is a growth factor dependent cell line which displayed enhanced growth in GM-CSF supplemented medium (Lange, B., et al., *Blood* 70: 192, 1987; Valtieri, M., et al., *J. Immunol.* 138:4042, 1987). The ability of AML 193 cells to proliferate in the presence of human IL-3 has also been documented. (Santoli, D., et al., *J. Immunol.* 139: 348, 1987). A cell line variant was used, AML 193 1.3, which was adapted for long term growth in IL-3 by washing out the growth factors and starving the cytokine dependent AML 193 cells for growth factors for 24 hours. The cells are then replated at $1\times10^5$ cells/well in a 24 well plate in media containing 100 U/mL IL-3. It took approximately 2 months for the cells to grow rapidly in IL-3. These cells are maintained as AML 193 1.3 thereafter by supplementing tissue culture medium (see below) with human IL-3.

AML 193 1.3 cells are washed 6 times in cold Hanks balanced salt solution (HBSS, Gibco, Grand Island, N.Y.) by centrifuging cell suspensions at 250×g for 10 minutes followed by decantation of the supernatant. Pelleted cells are resuspended in HBSS and the procedure is repeated until six wash cycles are completed. Cells washed six times by this procedure are resuspended in tissue culture medium at a density ranging from $2\times10^5$ to $5\times10^5$ viable cells/mL. This medium is prepared by supplementing Iscove's modified Dulbecco's Medium (IMDM, Hazelton, Lenexa, Kans.) with albumin, transferrin, lipids and 2-mercaptoethanol. Bovine albumin (Boehringer-Mannheim, Indianapolis, Ind.) is added at 500 μg/mL; human transferrin (Boehringer-Mannheim, Indianapolis, Ind.) is added at 100 μg/mL; soybean lipid (Boehringer-Mannheim, Indianapolis, Ind.) is added at 50 μg/mL; and 2-mercaptoethanol (Sigma, St. Louis, Mo.) is added at $5\times10^{-5}$ M.

Serial dilutions of G-CSF receptor agonist proteins are made in triplicate series in tissue culture medium supplemented as stated above in 96 well Costar 3596 tissue culture plates. Each well contained 50 μl of medium containing G-CSF receptor agonist proteins once serial dilutions are completed. Control wells contained tissue culture medium alone (negative control). AML 193 1.3 cell suspensions prepared as above are added to each well by pipetting 50 μl ($2.5\times10^4$ cells) into each well. Tissue culture plates are incubated at 37° C. with 5% $CO_2$ in humidified air for 3 days. On day 3, 0.5 μCi $^3$H-thymidine (2 Ci/mM, New England Nuclear, Boston, Mass.) is added in 50 μl of tissue culture medium. Cultures are incubated at 37° C. with 5% $CO_2$ in humidified air for 18–24 hours. Cellular DNA is harvested onto glass filter mats (Pharmacia LKB, Gaithersburg, Md.) using a TOMTEC cell harvester (TOMTEC, Orange, Conn.) which utilized a water wash cycle followed by a 70% ethanol wash cycle. Filter mats are allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) is added. Beta emissions of samples from individual tissue culture wells are counted in a LKB BetaPlate model 1205 scintillation counter (Pharmacia LKB, Gaithersburg, Md.) and data is expressed as counts per minute of $^3$H-thymidine incorporated into cells from each tissue culture well. Activity of each G-CSF receptor agonist proteins preparation is quantitated by measuring cell proliferation ($^3$H-thymidine incorporation) induced by graded concentrations of G-CSF receptor agonist. Typically, concentration ranges from 0.05 pM–$10^5$ pM are quantitated in these assays. Activity is determined by measuring the dose of G-CSF receptor agonist protein which provides 50% of maximal proliferation ($EC_{50}$=0.5×(maximum average counts per minute of $^3$H-thymidine incorporated per well among triplicate cultures of all concentrations of G-CSF receptor agonists tested—background proliferation measured by $^3$H-thymidine incorporation observed in triplicate cultures lacking any factor). This $EC_{50}$ value is also equivalent to 1 unit of bioactivity. Every assay is performed with native interleukin-3 and G-CSF as reference standards so that relative activity levels could be assigned.

Typically, the G-CSF receptor agonist proteins were tested in a concentration range of 2000 pM to 0.06 pM titrated in serial 2 fold dilutions.

Activity for each sample was determined by the concentration which gave 50% of the maximal response by fitting a four-parameter logistic model to the data. It was observed that the upper plateau (maximal response) for the sample and the standard with which it was compared did not differ. Therefore relative potency calculation for each sample was determined from EC50 estimations for the sample and the standard as indicated above.

Other in vitro Cell Based Proliferation Assays

Other in vitro cell based proliferation assays, known to those skilled in the art, may also be useful to determine the activity of the G-CSF receptor agonists in a similar manner as described in the AML 193.1.3 cell proliferation assay.

Transfected Cell Lines

Cell lines, such as BHK or the murine pro B cell line Baf/3, can be transfected with a colony stimulating factor receptor, such as the human G-CSF receptor which the cell line does not have. These transfected cell lines can be used to determine the activity of the ligand of which the receptor has been transfected.

EXAMPLE 1

Construction of pMON3485

The new N-terminus/C-terminus gene in pMON3485 was created using Method I as described in Materials and Methods. Fragment Start was created and amplified from G-CSF Ser$^{17}$ sequence in pMON13037 using the primer set, 39 start (SEQ ID NO:7) and L-11 start (SEQ ID NO:3). Fragment Stop was created and amplified from G-CSF Ser$^{17}$ sequence in the plasmid, pMON13037 (WO 95/21254), using the primer set, 38 stop (SEQ ID NO:8) and L-11 stop (SEQ ID NO:4). The full-length new N terminus/C-terminus G-CSF Ser$^{17}$ gene was created and amplified from the annealed Fragments Start and Stop using the primers 39 start (SEQ ID NO:7) and 38 stop (SEQ ID NO:8).

The resulting DNA fragment which contains the new gene was digested with restriction endonucleases NcoI and HindIII and purified using a Magic DNA Clean-up System kit (Promega, Madison, Wis.). The plasmid, pMON3934 (derivative of pMON3359), was digested with restriction endonucleases HindIII and NcoI, resulting in an approximately 3800 base pair vector fragment, and gel-purified. The purified restriction fragments were combined and ligated using T4 DNA ligase. A portion of the ligation reaction was used to transform *E. coli* strain DH5α cells (Life Technologies, Gaithersburg, Md.). Transformant bacteria were selected on ampicillin-containing plates. Plasmid DNA was isolated and sequenced to confirm the correct insert. The resulting plasmid was designated pMON3485.

BHK cells were transfected with the plasmid, pMON3485, for protein expression and bioassay.

The plasmid, pMON3485 containing the gene sequence of (SEQ ID NO:25), encodes the following amino acid sequence:

(SEQ ID NO:43)
Tyr Lys Leu Cys His Pro Glu Glu Leu Val Leu Leu

Gly His Ser Leu Gly Ile Pro Trp Ala Pro Leu Ser

Ser Cys Pro Ser Gln Ala Leu Gln Leu Ala Gly Cys

Leu Ser Gln Leu His Ser Gly Leu Phe Leu Tyr Gln

Gly Leu Leu Gln Ala Leu Glu Gly Ile Ser Pro Glu

Leu Gly Pro Thr Leu Asp Thr Leu Gln Leu Asp Val

Ala Asp Phe Ala Thr Thr Ile Trp Gln Gln Met Glu

Glu Leu Gly Met Ala Pro Ala Leu Gln Pro Thr Gln

Gly Ala Met Pro Ala Phe Ala Ser Ala Phe Gln Arg

Arg Ala Gly Gly Val Leu Val Ala Ser His Leu Gln

Ser Phe Leu Glu Val Ser Tyr Arg Val Leu Arg His

Leu Ala Gln Pro Ser Gly Gly Ser Gly Gly Ser Gln

Ser Phe Leu Leu Lys Ser Leu Glu Gln Val Arg Lys

Ile Gln Gly Asp Gly Ala Ala Leu Gln Glu Lys Leu

Cys Ala Thr

EXAMPLE 2

Construction of pMON3486

The new N-terminus/C-terminus gene in pMON3486 was created using Method I as described in Materials and Methods. Fragment Start was created and amplified from G-CSF Serl$^7$ sequence in the plasmid, pMON13037, using the primer set, 97 start (SEQ ID NO:9) and L-11 start (SEQ ID NO:3). Fragment Stop was created and amplified from G-CSF Ser$^{17}$ sequence in pMON13037 using the primer set, 96 stop (SEQ ID NO:10) and L-11 stop (SEQ ID NO:4). The full-length new N terminus/C-terminus G-CSF Ser$^{17}$ gene was created and amplified from the annealed Fragments Start and Stop using the primers 97 start (SEQ ID NO:9) and 96 stop (SEQ ID NO:10).

The resulting DNA fragment which contains the new gene was digested with restriction endonucleases NcoI and HindIII and gel-purified using a Magic DNA Clean-up System kit. The plasmid, pMON3934, was digested with restriction endonucleases HindIII and NcoI, resulting in an approximately 3800 base pair vector fragment, and gel-purified. The purified restriction fragments were combined and ligated using T4 DNA ligase. A portion of the ligation reaction was used to transform *E. coli* strain DH5α cells. Transformant bacteria were selected on ampicillin-containing plates. Plasmid DNA was isolated and sequenced to confirm the correct insert. The resulting plasmid was designated pMON3486.

BHK cells were transfected with the plasmid, pMON3486, for protein expression and bioassay.

The plasmid, pMON3486 containing the gene sequence of (SEQ ID NO:26), encodes the following amino acid sequence:

(SEQ ID NO:44)
Pro Glu Leu Gly Pro Thr Leu Asp Thr Leu Gln Leu

Asp Val Ala Asp Phe Ala Thr Thr Ile Trp Gln Gln

Met Glu Glu Leu Gly Met Ala Pro Ala Leu Gln Pro

Thr Gln Gly Ala Met Pro Ala Phe Ala Ser Ala Phe

Gln Arg Arg Ala Gly Gly Val Leu Val Ala Ser His

Leu Gln Ser Phe Leu Glu Val Ser Tyr Arg Val Leu

Arg His Leu Ala Gln Pro Ser Gly Gly Ser Gly Gly

Ser Gln Ser Phe Leu Leu Lys Ser Leu Glu Gln Val

Arg Lys Ile Gln Gly Asp Gly Ala Ala Leu Gln Glu

Lys Leu Cys Ala Thr Tyr Lys Leu Cys His Pro Glu

Glu Leu Val Leu Leu Gly His Ser Leu Gly Ile Pro

Trp Ala Pro Leu Ser Ser Cys Pro Ser Gln Ala Leu

Gln Leu Ala Gly Cys Leu Ser Gln Leu His Ser Gly

Leu Phe Leu Tyr Gln Gly Leu Leu Gln Ala Leu Glu

Gly Ile Ser

EXAMPLE 3

Construction of pMON3487

The new N-terminus/C-terminus gene in pMON3487 was created using Method I as described in Materials and Methods. Fragment Start was created and amplified from G-CSF Ser[17] sequence in the plasmid, pMON13037, using the primer set, 126 start (SEQ ID NO:11) and L-11 start (SEQ ID NO:3). Fragment Stop was created and amplified from G-CSF Ser[17] sequence in pMON13037 using the primer set, 125 stop (SEQ ID NO:12) and L-11 stop (SEQ ID NO:4). The full-length new N terminus/C-terminus G-CSF Ser[17] gene was created and amplified from the annealed Fragments Start and Stop using the primers 126 start (SEQ ID NO:11) and 125 stop (SEQ ID NO:12).

The resulting DNA fragment which contains the new gene was digested with restriction endonucleases NcoI and HindIII and purified using a Magic DNA Clean-up System kit. The plasmid, pMON3934, was digested with restriction endonucleases HindIII and NcoI, resulting in an approximately 3800 base pair vector fragment, and gel-purified. The purified restriction fragments were combined and ligated using T4 DNA ligase. A portion of the ligation reaction was used to transform E. coli strain DH5α cells. Transformant bacteria were selected on ampicillin-containing plates. Plasmid DNA was isolated and sequenced to confirm the correct insert. The resulting plasmid was designated pMON3487.

BHK cells were transfected with the plasmid, pMON3487, for protein expression and bioassay.

The plasmid, pMON3487 containing the gene sequence of (SEQ ID NO:27), encodes the following amino acid sequence:

(SEQ ID NO:45)
Met Ala Pro Ala Leu Gln Pro Thr Gln Gly Ala Met

Pro Ala Phe Ala Ser Ala Phe Gln Arg Arg Ala Gly

Gly Val Leu Val Ala Ser His Leu Gln Ser Ph

-continued
Leu Gln Ser Phe Leu Glu Val Ser Tyr Arg Val Leu

Arg His Leu Ala Gln Pro Ser Gly Gly Ser Gly Gly

Ser Gln Ser Phe Leu Leu Lys Ser Leu Glu Gln Val

Arg Lys Ile Gln Gly Asp Gly Ala Ala Leu Gln Glu

Lys Leu Cys Ala Thr Tyr Lys Leu Cys His Pro Glu

Glu Leu Val Leu Leu Gly His Ser Leu Gly Ile Pro

Trp Ala Pro Leu Ser Ser Cys Pro Ser Gln Ala Leu

Gln Leu Ala Gly Cys Leu Ser Gln Leu His Ser Gly

Leu Phe Leu Tyr Gln Gly Leu Leu Gln Ala Leu Glu

Gly Ile Ser Pro Glu Leu Gly Pro Thr Leu Asp Thr

Leu Gln Leu Asp Val Ala Asp Phe Ala Thr Thr Ile

Trp Gln Gln Met Glu Glu Leu Gly Met Ala Pro Ala

Leu Gln Pro

EXAMPLE 5
Construction of pMON3489

The new N-terminus/C-terminus gene in pMON3489 was created using Method I as described in Materials and Methods. Fragment Start was created and amplified from G-CSF Ser[17] sequence in the plasmid, pMON13037, using the primer set, 142 start (SEQ ID NO:15) and L-11 start (SEQ ID NO:3). Fragment Stop was created and amplified from G-CSF Ser[17] sequence in pMON13037 using the primer set, 141 stop (SEQ ID NO:16) and L-11 stop (SEQ ID NO:4). The full-length new N terminus/C-terminus G-CSF Ser[17] gene was created and amplified from the annealed Fragments Start and Stop using the primers 142 start (SEQ ID NO:15) and 141 stop (SEQ ID NO:16).

The resulting DNA fragment which contains the new gene was digested with restriction endonucleases NcoI and HindIII and purified using a Magic DNA Clean-up System kit. The plasmid, pMON3934, was digested with restriction endonucleases HindIII and NcoI, resulting in an approximately 3800 base pair vector fragment, and gel-purified. The purified restriction fragments were combined and ligated using T4 DNA ligase. A portion of the ligation reaction was used to transform E. coli strain DH5α cells. Transformant bacteria were selected on ampicillin-containing plates. Plasmid DNA was isolated and sequenced to confirm the correct insert. The resulting plasmid was designated pMON3489.

BHK cells were transfected with the plasmid, pMON3489, for protein expression and bioassay.

The plasmid, pMON3489 containing the gene sequence of (SEQ ID NO:29), encodes the following amino acid sequence:

(SEQ ID NO:47)
Ser Ala Phe Gln Arg Arg Ala Gly Gly Val Leu Val

Ala Ser His Leu Gln Ser Phe Leu Glu Val Ser Tyr

Arg Val Leu Arg His Leu Ala Gln Pro Ser Gly Gly

Ser Gly Gly Ser Gln Ser Phe Leu Leu Lys Ser Leu

Glu Gln Val Arg Lys Ile Gln Gly Asp Gly Ala Ala

-continued
Leu Gln Glu Lys Leu Cys Ala Thr Tyr Lys Leu Cys

His Pro Glu Glu Leu Val Leu Leu Gly His Ser Leu

Gly Ile Pro Trp Ala Pro Leu Ser Ser Cys Pro Ser

Gln Ala Leu Gln Leu Ala Gly Cys Leu Ser Gln Leu

His Ser Gly Leu Phe Leu Tyr Gln Gly Leu Leu Gln

Ala Leu Glu Gly Ile Ser Pro Glu Leu Gly Pro Thr

Leu Asp Thr Leu Gln Leu Asp Val Ala Asp Phe Ala

Thr Thr Ile Trp Gln Gln Met Glu Glu Leu Gly Met

Ala Pro Ala Leu Gln Pro Thr Gln Gly Ala Met Pro

Ala Phe Ala

EXAMPLE 6
Construction of pMON3490

The new N-terminus/C-terminus gene in pMON3490 was created using Method II as described in Materials and Methods. Fragment Start was created and amplified from G-CSF sequence in the plasmid, pMON13037, using the primer set, 39 start (SEQ ID NO:7) and P-bl start (SEQ ID NO:5). Fragment Stop was created and amplified from G-CSF Ser[17] sequence in pMON13037 using the primer set, 38 stop (SEQ ID NO:8) and P-bl stop (SEQ ID NO:6). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934. Transformant bacteria were selected on ampicillin-containing plates. Plasmid DNA was isolated and sequenced to confirm the correct insert. The resulting plasmid was designated pMON3490.

BHK cells were transfected with the plasmid, pMON3490, for protein expression and bioassay.

The plasmid, pMON3490 containing the gene sequence of (SEQ ID NO:30), encodes the following amino acid sequence:

(SEQ ID NO:48)
Tyr Lys Leu Cys His Pro Glu Glu Leu Val Leu Leu

Gly His Ser Leu Gly Ile Pro Trp Ala Pro Leu Ser

Ser Cys Pro Ser Gln Ala Leu Gln Leu Ala Gly Cys

Leu Ser Gln Leu His Ser Gly Leu Phe Leu Tyr Gln

Gly Leu Leu Gln Ala Leu Glu Gly Ile Ser Pro Glu

Leu Gly Pro Thr Leu Asp Thr Leu Gln Leu Asp Val

Ala Asp Phe Ala Thr Thr Ile Trp Gln Gln Met Glu

Glu Leu Gly Met Ala Pro Ala Leu Gln Pro Thr Gln

Gly Ala Met Pro Ala Phe Ala Ser Ala Phe Gln Arg

Arg Ala Gly Gly Val Leu Val Ala Ser His Leu Gln

Ser Phe Leu Glu Val Ser Tyr Arg Val Leu Arg His

Leu Ala Gln Pro Thr Pro Leu Gly Pro Ala Ser Ser

Leu Pro Gln Ser Phe Leu Leu Lys Ser Leu Glu Gln

```
Val Arg Lys Ile Gln Gly Asp Gly Ala Ala Leu Gln

Glu Lys Leu Cys Ala Thr
```

EXAMPLE 7
Construction of pMON3491

The new N-terminus/C-terminus gene in pMON3491 was created using Method II as described in Materials and Methods. Fragment Start was created and amplified from G-CSF sequence in the plasmid, pMON13037, using the primer set, 97 start (SEQ ID NO:9) and P-bl start (SEQ ID NO:5). Fragment Stop was created and amplified from G-CSF Ser[17] sequence in pMON13037 using the primer set, 96 stop (SEQ ID NO:10) and P-bl stop (SEQ ID NO:6). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934. A portion of the ligation reaction was used to transform E. coli strain DH5α cells. Transformant bacteria were selected on ampicillin-containing plates. Plasmid DNA was isolated and sequenced to confirm the correct insert. The resulting plasmid was designated pMON3491.

BHK cells were transfected with the plasmid, pMON3491, for protein expression and bioassay.

The plasmid, pMON3491 containing the gene sequence of (SEQ ID NO:31), encodes the following amino acid sequence:

```
                                              (SEQ ID NO:49)
Pro Glu Leu Gly Pro Thr Leu Asp Thr Leu Gln Leu

Asp Val Ala Asp Phe Ala Thr Thr Ile Trp Gln Gln

Met Glu Glu Leu Gly Met Ala Pro Ala Leu Gln Pro

Thr Gln Gly Ala Met Pro Ala Phe Ala Ser Ala Phe

Gln Arg Arg Ala Gly Gly Val Leu Val Ala Ser His

Leu Gln Ser Phe Leu Glu Val Ser Tyr Arg Val Leu

Arg His Leu Ala Gln Pro Thr Pro Leu Gly Pro Ala

Ser Ser Leu Pro Gln Ser Phe Leu Leu Lys Ser Leu

Glu Gln Val Arg Lys Ile Gln Gly Asp Gly Ala Ala

Leu Gln Glu Lys Leu Cys Ala Thr Tyr Lys Leu Cys

His Pro Glu Glu Leu Val Leu Leu Gly His Ser Leu

Gly Ile Pro Trp Ala Pro Leu Ser Ser Cys Pro Ser

Gln Ala Leu Gln Leu Ala Gly Cys Leu Ser Gln Leu

His Ser Gly Leu Phe Leu Tyr Gln Gly Leu Leu Gln

Ala Leu Glu Gly Ile Ser
```

EXAMPLE 8
Construction of pMON3492

The new N-terminus/C-terminus gene in pMON3492 was created using Method II as described in Materials and Methods. Fragment Start was created and amplified from G-CSF sequence in the plasmid, pMON13037, using the primer set, 126 start (SEQ ID NO:11) and P-bl start (SEQ ID NO:5). Fragment Stop was created and amplified from G-CSF Ser[17] sequence in pMON13037 using the primer set, 125 stop (SEQ ID NO:12) and P-bl stop (SEQ ID NO:6). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934. A portion of the ligation reaction was used to transform E. coli strain DH5α cells. Transformant bacteria were selected on ampicillin-containing plates. Plasmid DNA was isolated and sequenced to confirm the correct insert. The resulting plasmid was designated pMON3492.

BHK cells were transfected with the plasmid, pMON3492, for protein expression and bioassay.

The plasmid, pMON3492 containing the gene sequence of (SEQ ID NO:32), encodes the following amino acid sequence:

```
                                              (SEQ ID NO:50)
Met Ala Pro Ala Leu Gln Pro Thr Gln Gly Ala Met

Pro Ala Phe Ala Ser Ala Phe Gln Arg Arg Ala Gly

Gly Val Leu Val Ala Ser His Leu Gln Ser Phe Leu

Glu Val Ser Tyr Arg Val Leu Arg His Leu Ala Gln

Pro Thr Pro Leu Gly Pro Ala Ser Ser Leu Pro Gln

Ser Phe Leu Leu Lys Ser Leu Glu Gln Val Arg Lys

Ile Gln Gly Asp Gly Ala Ala Leu Gln Glu Lys Leu

Cys Ala Thr Tyr Lys Leu Cys His Pro Glu Glu Leu

Val Leu Leu Gly His Ser Leu Gly Ile Pro Trp Ala

Pro Leu Ser Ser Cys Pro Ser Gln Ala Leu Gln Leu

Ala Gly Cys Leu Ser Gln Leu His Ser Gly Leu Phe

Leu Tyr Gln Gly Leu Leu Gln Ala Leu Glu Gly Ile

Ser Pro Glu Leu Gly Pro Thr Leu Asp Thr Leu Gln

Leu Asp Val Ala Asp Phe Ala Thr Thr Ile Trp Gln

Gln Met Glu Glu Leu Gly
```

EXAMPLE 9
Construction of pMON3493

The new N-terminus/C-terminus gene in pMON3493 was created using Method II as described in Materials and Methods. Fragment Start was created and amplified from G-CSF sequence in the plasmid, pMON13037, using the primer set, 133 start (SEQ ID NO:13) and P-bl start (SEQ ID NO:5). Fragment Stop was created and amplified from G-CSF Ser[17] sequence in pMON13037 using the primer set, 132 stop (SEQ ID NO:14) and P-bl stop (SEQ ID NO:6). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934. A portion of the ligation reaction was used to transform E. coli strain DH5α cells. Transformant bacteria were selected on ampicillin-containing plates. Plasmid DNA was isolated and sequenced to confirm the correct insert. The resulting plasmid was designated pMON3493.

BHK cells were transfected with the plasmid, pMON3493, for protein expression and bioassay.

The plasmid, pMON3493 containing the gene sequence of (SEQ ID NO:33), encodes the following amino acid sequence:

(SEQ ID NO:51)
Thr Gln Gly Ala Met Pro Ala Phe Ala Ser Ala Phe
Gln Arg Arg Ala Gly Gly Val Leu Val Ala Ser His
Leu Gln Ser Phe Leu Glu Val Ser Tyr Arg Val Leu
Arg His Leu Ala Gln Pro Thr Pro Leu Gly Pro Ala
Ser Ser Leu Pro Gln Ser Phe Leu Leu Lys Ser Leu
Glu Gln Val Arg Lys Ile Gln Gly Asp Gly Ala Ala
Leu Gln Glu Lys Leu Cys Ala Thr Tyr Lys Leu Cys
His Pro Glu Glu Leu Val Leu Leu Gly His Ser Leu
Gly Ile Pro Trp Ala Pro Leu Ser ser Cys Pro Ser
Gln Ala Leu Gln Leu Ala Gly Cys Leu Ser Gln Leu
His Ser Gly Leu Phe Leu Tyr Gln Gly Leu Leu Gln
Ala Leu Glu Gly Ile Ser Pro Glu Leu Gly Pro Thr
Leu Asp Thr Leu Gln Leu Asp Val Ala Asp Phe Ala
Thr Thr Ile Trp Gln Gln Met Glu Glu Leu Gly Met
Ala Pro Ala Leu Gln Pro

EXAMPLE 10
Construction of pMON3494

The new N-terminus/C-terminus gene in pMON3494 was created using Method II as described in Materials and Methods. Fragment Start was created and amplified from G-CSF sequence in the plasmid, pMON13037, using the primer set, 142 start (SEQ ID NO:15) and P-bl start (SEQ ID NO:5). Fragment Stop was created and amplified from G-CSF Ser[17] sequence in pMON13037 using the primer set, 141 stop (SEQ ID NO:16) and P-bl stop (SEQ ID NO:6). Fragment Start was digested with restriction endonuclease NcoI, and Fragment Stop was digested with restriction endonuclease HindIII. After purification, the digested Fragments Start and Stop were combined with and ligated to the approximately 3800 base pair NcoI-HindIII vector fragment of pMON3934. A portion of the ligation reaction was used to transform E. coli strain DH5α cells. Transformant bacteria were selected on ampicillin-containing plates. Plasmid DNA was isolated and sequenced to confirm the correct insert. The resulting plasmid was designated pMON3494.

BHK cells were transfected with the plasmid, pMON3494, for protein expression and bioassay.

The plasmid, pMON3494 containing the gene sequence of (SEQ ID NO:34), encodes the following amino acid sequence:

(SEQ ID NO:52)
Ser Ala Phe Gln Arg Arg Ala Gly Gly Val Leu Val
Ala Ser His Leu Gln Ser Phe Leu Glu Val Ser Tyr
Arg Val Leu Arg His Leu Ala Gln Pro Thr Pro Leu
Gly Pro Ala Ser Ser Leu Pro Gln Ser Phe Leu Leu
Lys Ser Leu Glu Gln Val Arg Lys Ile Gln Gly Asp
Gly Ala Ala Leu Gln Glu Lys Leu Cys Ala Thr Tyr
Lys Leu Cys His Pro Glu Glu Leu Val Leu Leu Gly
His Ser Leu Gly Ile Pro Trp Ala Pro Leu Ser Ser
Cys Pro Ser Gln Ala Leu Gln Leu Ala Gly Cys Leu
Ser Gln Leu His Ser Gly Leu Phe Leu Tyr Gln Gly
Leu Leu Gln Ala Leu Glu Gly Ile Ser Pro Glu Leu
Gly Pro Thr Leu Asp Thr Leu Gln Leu Asp Val Ala
Asp Phe Ala Thr Thr Ile Trp Gln Gln Met Glu Glu
Leu Gly Met Ala Pro Ala Leu Gln Pro Thr Gln Gly
Ala Met Pro Ala Phe Ala

EXAMPLES 11–20

The genes encoding the G-CSF receptor agonists of Examples 1–10 were excised from the BHK vectors as a NcoI/HindIII fragment and ligated with the ~3630 base pair NcoI/HindIII vector fragment of pMON2341 (WO 94/12638). The resulting plasmids (Examples 11–20) are indicated in Table 4. The plasmids were transformed into E. coli strain JM101 cells and expression of the G-CSF receptor agonist protein was evaluated. The proteins expressed are the same as those expressed in the parental BHK expression vector except the proteins were immediately preceded by a Methionine-Alanine dipeptide and the Methionine is processed off by methionine aminopeptidase. Overnight growths of cells (20 Klett units) were inoculated in 10 mL of minimal M9 medium supplemented with vitamin B1 and trace minerals and incubated with shaking at 37° C. until initial Klett readings of ~120 units were obtained. At 120 Klett units 5 uL of 10 mg/mL nalidixic acid was added. Four hours post-induction, a 1 ml aliquot was removed for protein expression analysis by SDS-PAGE. Cells were also examined using light microscopy for the presence of inclusion bodies. Only pMON3450 and pMON3455 had significant expression levels of the G-CSF receptor agonist protein. In an effort to improve expression levels of G-CSF receptor agonists, the 5' end of the genes were re-engineered to incorporate AT-rich codons and E. coli preferred codons between the unique NcoI and NheI restriction endonuclease recognition sites (Examples 21–28).

TABLE 4

E. coli expression plasmids

| Example # | Resulting E. coli expression plasmid pMON# | Break-point | Linker | Parental BHK plasmid pMON# |
|---|---|---|---|---|
| Example 11 | pMON3450 | 38/39 | zero | pMON3490 |
| Example 12 | pMON3455 | 38/39 | Δ1–10 | pMON3485 |
| Example 13 | pMON3451 | 96/97 | zero | pMON3491 |
| Example 14 | pMON3456 | 96/97 | Δ1–10 | pMON3486 |
| Example 15 | pMON3452 | 125/126 | zero | pMON3492 |
| Example 16 | pMON3457 | 125/126 | Δ1–10 | pMON3487 |
| Example 17 | pMON3453 | 132/133 | zero | pMON3493 |
| Example 18 | pMON3458 | 132/133 | Δ1–10 | pMCN3488 |
| Example 19 | pMON3454 | 141/142 | zero | pMON3494 |
| Example 20 | pMON3459 | 141/142 | Δ1–10 | pMON3489 |

EXAMPLE 21
Construction of pMON25184

The complementary pair of synthetic oligomers, 141for.seq (SEQ ID NO:23) and 141rev.seq (SEQ ID NO:24), (Midland Certified Reagent Co., Midland Tex.) were annealed by heating 2 ug of each synthetic oligomer in a 20 ul reaction mixture containing 20 mM Tris-HCl (7.5), 10 mM $MgCl_2$, and 50 mM NaCl, at 80° C. for 5 minutes, and allowing the mixture to slowly cool to ambient temperature (approximately 45 minutes). When properly annealed the oligomers create an NcoI site at the 5' end and a NheI site at the 3' end. Approximately 15 ng of the annealed oligomer pair was ligated with the gel-purified ~4120 base pair NcoI/NheI vector fragment of pMON3454 (~molar ratio of 10:1). The resulting gene, had seven codon changes at the 5' end of the gene. The ligation reaction was used to transform *E. coli* strain DH5α and the desired codon changes were confirmed by DNA sequence analysis. The resulting plasmid was designated pMON25184. Plasmid, pMON25184 containing the gene sequence of (SEQ ID NO:38), DNA was retransformed into *E. coli* strain JM101 cells for protein expression. The protein expressed is the same as that expressed from pMON3454.

EXAMPLE 22
Construction of PMON25188

The complementary pair of synthetic oligomers, 141for.seq (SEQ ID NO:23) and 141rev.seq (SEQ ID NO:24), (Midland Certified Reagent Co., Midland Tex.) were annealed by heating 2 ug of each synthetic oligomer in a 20 ul reaction mixture containing 20 mM Tris-HCl (7.5), 10 mM $MgCl_2$, and 50 mM NaCl, at 80° C. for 5 minutes, and allowing the mixture to slowly cool to ambient temperature (approximately 45 minutes). When properly annealed the oligomers create an NcoI site at the 5' end and a NheI site at the 3' end. Approximately 15 ng of the annealed oligomer pair was ligated with the ~4110 base pair NcoI/NheI gel-purified pMON3459 (~molar ratio of 10:1). The ligation mixture was used to transform *E. coli* strain DH5α and the desired codon changes were confirmed by DNA sequence analysis. The resulting plasmid was designated pMON25188. The resulting gene, had seven codon changes at the 5' end of the gene. Plasmid, pMON25188 containing the gene sequence of (SEQ ID NO:42), DNA was retransformed into *E. coli* strain JM101 cells for protein expression. The protein expressed is the same as that expressed from pMON3459.

EXAMPLE 23
Construction of pMON25183 pMON25183 was constructed using an overlapping PCR primer method. The synthetic oligomers, 132for.seq (SEQ ID NO:321 and 132rev.seq (SEQ ID NO:22), encode the NcoI and NheI restriction recognition sequence, respectively. Amplified DNA was generated by the DNA polymerase chain amplification method using the PCR Optimizer Kit (Invitrogen). The PCR reactions were performed using the manufacturer's recommended conditions using 5×buffer B (300 mM Tris-HCl pH8.5, 75 mM $(NH_4)_2SO_4$, 10 mM $MgCl_2$) for seven cycles consisting of 94° C. for 1', 65° C. for 2', and 72° C. for 2', followed by 20 cycles of 94° C. for 1', and 72° C. for 3', and a final cycle of 7 minutes at 72° C. using a Perkin Elmer Model 480 DNA thermal cycler (Perkin Elmer). The reaction product was desalted using Centri-Sep spin columns (Princeton Separations) following the manufacturer's recommended protocol, digested with NcoI/NheI, and gel purified from TAE-agarose gels using Gene Clean (Bio 101) and the DNA product was eluted in $dH_2O$ The purified PCR product was ligated with the ~4090 base pair NcoI/NheI pMON3453 vector fragment. Positive clones containing the AT-rich replacement insert were identified as described in Example 21. The resulting plasmid was designated pMON25183. The resulting gene, had 14 codon changes at the 5' end of the gene. Plasmid, pMON25183 containing the gene sequence of (SEQ ID NO:37), DNA was retransformed into *E. coli* strain JM101 cells for protein expression. The protein expressed is the same as that expressed from pMON3453.

EXAMPLE 24
Construction of pMON25187 pMON25187 was constructed using an overlapping PCR primer method. The synthetic oligomers, 132for.seq (SEQ ID NO:21) and 132rev.seq (SEQ ID NO:22), encode the NcoI and NheI restriction recognition sequence, respectively. Amplified DNA was generated by the DNA polymerase chain amplification method using the PCR Optimizer Kit (Invitrogen). The PCR reactions were performed using the manufacturer's recommended conditions, in 5×buffer B for seven cycles consisting of 94° C. for 1', 65° C. for 2', and 72° C. for 2', followed by 20 cycles of 94° C. for 1', and 72° C. for 3', and a final cycle of 7 minutes at 72° C. using a Perkin Elmer Model 480 DNA thermal cycler (Perkin Elmer). The reaction product was desalted using Centri-Sep spin columns (Princeton Separations) following the manufacturer's recommended protocol, digested with NcoI/NheI, and gel purified from TAE-agarose gels using Gene Clean (Bio 101) and the DNA product was eluted in $dH_2O$. The purified PCR product was ligated with the ~4080 base pair NcoI/NheI pMON3458 vector fragment. Positive clones containing the AT-rich replacement insert were identified as described in Example 21. The resulting plasmid was designated pMON25187. The resulting gene, had 14 codon changes at the 5' end of the gene. Plasmid, pMON25187 containing the gene sequence of (SEQ ID NO:41), DNA was retransformed into *E. coli* strain JM101 cells for protein expression. The protein expressed is the same as that expressed from pMON3458.

EXAMPLE 25
Construction of pMON25182 pMON25182 was constructed using the overlapping PCR primer approach described in Example 23. The synthetic oligomer primers 125for.seq (SEQ ID NO:19) and 125rev.seq (SEQ ID NO:20) were used in the PCR reaction. The PCR reaction conditions were identical to those used in Example 23 except the annealing temperature for the first seven cycles was 60° C. The purified PCR product was ligated with ~4070 base pair NcoI/NheI pMON3452 vector fragment. Positive clones containing the AT-rich replacement insert were identified a s described in Example 21. The resulting plasmid was designated pMON25182. The resulting gene, had 19 codon changes at the 5' end of the gene. Plasmid, pMON25182 containing the gene sequence of (SEQ ID NO:36), DNA was retransfomed into *E. coli* strain JM101 cells for protein expression. The protein expressed is the same as that expressed from pMON3452.

EXAMPLE 26
Construction of pMON25186 pMON25186 was constructed using the overlapping PCR primer approach described in Example 23. The synthetic oligomer primers 125for.seq (SEQ ID NO:19) and 125rev.seq (SEQ ID NO:20) were used in the PCR reaction. The PCR reaction conditions were identical to those used in Example 23 except the annealing temperature for the first seven cycles was 60° C. The purified PCR product was ligated with the ~4060 base pair NcoI/NheI pMON3457 vector fragment. Positive clones containing the AT-rich replacement insert were identified as described in Example 21. The resulting plasmid was designated pMON25186. The resulting gene, had 19 codon changes at the 5' end of the gene. Plasmid, pMON25186 containing the gene sequence of (SEQ ID NO:40), DNA was retransformed into *E. coli* strain JM101 cells for protein expression. The protein expressed is the same as that expressed from pMON3457.

EXAMPLES 27

Construction of pMON25181 pMON25181 was constructed using PCR to amplify a DNA fragment from pMON3451 as the template using the oligomers 96for.seq (SEQ ID NO:17) and 96rev.seq (SEQ ID NO:18). The oligomer 96for.seq was designed to create six codon changes. The PCR reaction conditions were the same as described in Example 25, except 10 ng of pMON3451 plasmid DNA was added. The purified PCR product was ligated with the ~3980 base pair NcoI/NheI pMON3451 vector fragment. Positive clones containing the AT-rich replacement insert were identified as described in Example 21. The resulting plasmid was designated pMON25181. The resulting gene, had 6 codon changes at the 5' end of the gene. Plasmid, pMON25181 containing the gene sequence of (SEQ ID NO:35), DNA was retransformed into *E. coli* strain JM101 cells for protein expression. The protein expressed is the same as that expressed from pMON3451.

EXAMPLES 28

Construction of pMON25185 pMON25185 was constructed using PCR to amplify a DNA fragment from pMON3451 as the template using the oligomers 96for.seg (SEQ ID NO:17) and 96rev.seq (SEQ ID NO:18). The oligomer 9697for.seq was designed to create six codon changes. The PCR reaction conditions were the same as described in Example 25, except 10 ng of pMON3456 plasmid DNA was added. The purified PCR product was ligated with the ~3970 base pair NcoI/NheI pMON3456 vector fragment. Positive clones containing the AT-rich replacement insert were identified as described in Example 21. The resulting plasmid was designated pMON25185. The resulting gene, had 6 codon changes at the 5' end of the gene. Plasmid, pMON25185 containing the gene sequence of (SEQ ID NO:39), DNA was retransformed into *E. coli* strain JM101 cells for protein expression. The protein expressed is the same as that expressed from pMON3456.

EXAMPLE 29

The G-CSF amino acid substitution variants of the present invention were made using PCR mutagenesis techniques as described in WO 94/12639 and WO 94/12638. These and other variants (i.e. amino acid substitutions, insertions or deletions and N-terminal or C-terminal extensions) could also be made, by one skilled in the art, using a variety of other methods including synthetic gene assembly or site-directed mutagenesis (see Taylor et al., *Nucl. Acids Res.*, 13:7864–8785, 1985; Kunkel et al., *Proc. Natl. Acad. Sci. USA*, 82:488–492, 1985; Sambrook et al., Molecular Cloning: A Laboratory Manual, 2nd ed., Cold Spring Harbor Laboratory Press, Cold Spring Harbor, N.Y., 1989, WO 94/12639 and WO 94/12638). These substitutions can be made one at a time or in combination with other amino acid substitutions, and/or deletions, and/or insertions and/or extensions. After sequence verification of the changes, the plasmid DNA can be transfected into an appropriate mammalian cell, insect cell or bacterial strain such as *E. coli* for production. Known variants of G-CSF, which are active, include substitutions at positions 1 (Thr to Ser, Arg or Gly, 2 (Pro to Leu), 3 (Leu to Arg or Ser) and 17 (Cys to Ser) and deletions of amino acids 1–11 (Kuga et al. *Biochemicla and Biophysical Research Comm.* 159:103–111, 1989). It is understood that these G-CSF amino acid substitution variants could serve as the template sequence for the rearrangement of the amino acid sequence as described in the other examples.

Bioactivity determination of G-CSF amino acid substitution variants.

The G-CSF amino acid substitution variants were assayed in the Baf/3 cell line, transfected with the human G-CSF receptor, proliferation assay to determine their bioactivity relative to native G-CSF. The G-CSF variants tested and their relative bioactivity are shown in Table 5. A "+" indicates that the activity was comparable to native G-CSF and "−" indicates that the activity was significantly decreased or not detected.

TABLE 5

CELL PROLIFERATION ACTIVITY OF G-CSF VARIANTS IN BAF/3 CELL LINE TRANSFECTED WITH THE HUMAN G-CSF RECEPTOR

| aa position | native aa | mutant aa | activity * |
|---|---|---|---|
| 13 | Phe | Ser | + |
| 13 | Phe | His | + |
| 13 | Phe | Thr | + |
| 13 | Phe | Pro | + |
| 16 | Lys | Pro | + |
| 16 | Lys | Ser | + |
| 16 | Lys | Thr | + |
| 16 | Lys | His | + |
| 18 | Leu | Pro | + |
| 18 | Leu | His | + |
| 18 | Leu | Cys | + |
| 18 | Leu | Ile | + |
| 19 | Glu | Ala | − |
| 19 | Glu | Thr | − |
| 19 | Glu | Arg | − |
| 19 | Glu | Pro | − |
| 19 | Glu | Leu | − |
| 19 | Glu | Gly | − |
| 19 | Glu | Ser | − |
| 22 | Arg | Tyr | + |
| 22 | Arg | Ser | + |
| 22 | Arg | Ala | + |
| 22 | Arg | Val | + |
| 22 | Arg | Thr | + |
| 24 | Ile | Pro | + |
| 24 | Ile | Leu | + |
| 24 | Ile | Tyr | + |
| 27 | Asp | Gly | + |
| 30 | Ala | Ile | + |
| 30 | Ala | Leu | + |
| 34 | Lys | Ser | + |
| 43 | His | Gly | + |
| 43 | His | Thr | + |
| 43 | His | Val | + |
| 43 | His | Lys | + |
| 43 | His | Trp | + |
| 43 | His | Ala | + |
| 43 | His | Arg | + |
| 43 | His | Cys | + |
| 43 | His | Leu | + |
| 44 | Pro | Arg | + |
| 44 | Pro | Asp | + |
| 44 | Pro | Val | + |
| 44 | Pro | Ala | + |

TABLE 5-continued

CELL PROLIFERATION ACTIVITY OF G-CSF
VARIANTS IN BAF/3 CELL LINE TRANSFECTED
WITH THE HUMAN G-CSF RECEPTOR

| aa position | native aa | mutant aa | activity * |
|---|---|---|---|
| 44 | Pro | His | + |
| 44 | Pro | Gln | + |
| 44 | Pro | Trp | + |
| 44 | Pro | Gly | + |
| 44 | Pro | Thr | + |
| 46 | Glu | Ala | + |
| 46 | Glu | Arg | + |
| 46 | Glu | Phe | + |
| 46 | Glu | Ile | + |
| 47 | Leu | Thr | + |
| 49 | Leu | Phe | + |
| 49 | Leu | Arg | + |
| 49 | Leu | Ser | + |
| 50 | Leu | His | + |
| 50 | Leu | Pro | + |
| 51 | Gly | Ser | + |
| 51 | Gly | Met | + |
| 54 | Leu | His | + |
| 67 | Gln | Lys | + |
| 67 | Gln | Leu | + |
| 67 | Gln | Cys | + |
| 67 | Gln | Lys | + |
| 70 | Gln | Pro | + |
| 70 | Gln | Leu | + |
| 70 | Gln | Arg | + |
| 70 | Gln | Ser | + |
| 104 | Asp | Gly | + |
| 104 | Asp | Val | + |
| 108 | Leu | Ala | + |
| 108 | Leu | Val | + |
| 108 | Leu | Arg | + |
| 108 | Leu | Gly | + |
| 108 | Leu | Trp | + |
| 108 | Leu | Gln | + |
| 115 | Thr | His | + |
| 115 | Thr | Leu | + |
| 115 | Thr | Ala | + |
| 115 | Thr | Ile | + |
| 120 | Gln | Gly | + |
| 120 | Gln | Arg | + |
| 120 | Gln | Lys | + |
| 120 | Gln | His | + |
| 123 | Glu | Arg | + |
| 123 | Glu | Phe | + |
| 123 | Glu | Thr | + |
| 144 | Phe | His | + |
| 144 | Phe | Arg | + |
| 144 | Phe | Pro | + |
| 144 | Phe | Leu | + |
| 144 | Phe | Glu | + |
| 146 | Arg | Gln | + |
| 147 | Arg | Gln | + |
| 156 | His | Asp | − |
| 156 | His | Ser | + |
| 156 | His | Gly | + |
| 159 | Ser | Arg | + |
| 159 | Ser | Thr | + |
| 159 | Ser | Tyr | + |
| 159 | Ser | Tyr | + |
| 162 | Glu | Gly | − |
| 162 | Glu | Trp | + |
| 162 | Glu | Leu | + |
| 163 | Val | Arg | + |
| 163 | Val | Arg | + |
| 163 | Val | Gly | + |
| 165 | Tyr | Cys | not determined |
| 169 | Ser | Leu | + |
| 169 | Ser | Cys | + |
| 169 | Ser | Arg | + |
| 170 | His | Arg | + |
| 170 | His | Ser | + |

EXAMLPLE 30–37

Examples 30–37 were made in a similar manner as described in Example 6 using the plasmid pMON13037 as the template and the oligonucleotide primers indicated in Table 6. The resulting gene and the designated plasmid pMON # and the protein encoded are indicated in Table 6.

TABLE 6

| Example | breakpoint | primers | resulting gene | resulting protein |
|---|---|---|---|---|
| 30 | 48/49 | 49start (SEQ ID NO:68) 48stop (SEQ ID NO:69) | pMON3460 (SEQ ID NO:86) | (SEQ ID NO:95) |
| 31 | 76/77 81/82 | 77start (SEQ ID NO:70) 76stop (SEQ ID NO:71) | pMON3461 (SEQ ID NO:87) | (SEQ ID NO:96) |
| 32 | 81/82 | 82start (SEQ ID NO:72) 81stop (SEQ ID NO:73) | pMON3462 (SEQ ID NO:88) | (SEQ ID NO:97) |
| 33 | 83/84 | 84start (SEQ ID NO:74) 83stop (SEQ ID NO:75) | pMON3463 (SEQ ID NO:88) | (SEQ ID NO:98) |
| 34 | 90/91 | 91start (SEQ ID NO:76) 90stop (SEQ ID NO:77) | pMON3464 (SEQ ID NO:89) | (SEQ ID NO:99) |

TABLE 6-continued

| Example | breakpoint | primers | resulting gene | resulting protein |
|---------|------------|---------|----------------|-------------------|
| 35 | 111/112 | 112start (SEQ ID NO:78) 111stop (SEQ ID NO:79) | pMON3465 (SEQ ID NO:90) | (SEQ ID NO:100) |
| 36 | 116/117 | 117start (SEQ ID NO:80) 116stop (SEQ ID NO:81) | pMON3466 (SEQ ID NO:91) | (SEQ ID NO:101) |
| 37 | 118/119 | 119start (SEQ ID NO:82) 118stop (SEQ ID NO:83) | pMON3467 (SEQ ID NO:92) | (SEQ ID NO:102) |

The G-CSF receptor agonist genes in pMON3640, pMON3461, pMON3462, pMON3463, pMON3464, pMON3465, pMON3466 and pMON3467 were transferred to an E. coli expression vector, pMON2341, as an NcoI/HindIII restriction fragment, resulting in the plasmids pMON3468, pMON3469, pMON3470, pMON3471, pMON3472, pMON3473, pMON3474 and pMON3498 respectively.

EXAMPLE 38

The plasmid, pMON3468, resulted in low expression levels in E. coli of the desired G-CSF receptor agonist. The 5' end of the gene was redesigned to use codon selection that was AT rich to increase expression levels. The oligonucleotides, Z4849AT.for (SEQ ID NO:84) and Z4849AT.rev (SEQ ID NO:85), were used to re-engineer the gene. The resulting plasmid, pMON3499, containing the gene (SEQ ID NO:94) encodes the G-CSF receptor agonist of (SEQ ID NO:103).

EXAMPLE 39

The G-CSF receptor agonists were assayed in the Baf/3 cell line, transfected with the human G-CSF receptor, (Baf/3-G-CSF) proliferation assay to determine their bioactivity relative to native G-CSF. The activity of the receptor agonists is shown in Table 7.

TABLE 7

G-CSF receptor agonist activity in Baf/3-G-CSF cell proliferation assay

| PMON# | break-point | Expression | E. coli refold | EC50 (pM) |
|-------|-------------|------------|----------------|-----------|
| native G-CSF | | | | 60 pM |
| pMON25182 | 125/126 | + | + | 38 pM |
| pMON25183 | 132/133 | + | + | 58 pM |
| pMON25184 | 141/142 | + | + | 70 pM |
| pMON25186 | 125/126 | + | + | 92 pM |
| pMON25187 | 132/133 | + | + | 83 pM |
| pMON25188 | 141/142 | + | + | 41 pM |
| pMON3450 | 38/39 | + | + | 121 pM |
| pMON3455 | 38/39 | + | + | 102 pM |
| pMON3499 | 48/49 | + | + | 137 pM |
| pMON3470 | 81/82 | + | + | no activity detected |
| pMON3473 | 111/112 | + | − | |

EXAMPLES 40–52

The plasmids in Table 8 contain genes encoding sequence rearranged G-CSF receptor agonists that were made by the method of Horlich et al (Protein Eng. 5:427–431, 1992). As described in Materials and Methods, the tandem repeat of the G-CSF Ser$^{17}$ gene was maintained on a pACYC177 based plasmid (Chang and Cohen, J. Bacteriol. 1341141–1156, 1978), containing the sequence; GAG ATG GCT, encoding; Asp Met Ala, following immediately downstream of amino acid 174 of the first copy of the G-CSF Ser$^{17}$ gene and immediately preceeding amino acid 1 of the second copy of the G-CSF Ser$^{17}$ gene. The resulting sequence rearranged G-CSF receptor agonists have the linker; Asp Met Ala, between the original C-terminus and original N-terminus of G-CSF Ser$^{17}$. The sequence rearranged G-CSF receptor agonists encoded by the plasmids of Table 8 were identified using a G-CSF receptor binding screen (Wantanabe et al. Analyt. Biochem 195:38–44, 1991). The sequence rearranged G-CSF receptor agonists shown in Table 8 had receptor binding comparable to or better than native recombinant hG-CSF.

TABLE 8

| plasmid designation | breakpoint | gene sequence | protein sequence |
|---------------------|------------|---------------|------------------|
| pG32 | 2–3 | SEQ ID NO:110 | SEQ ID NO:122 |
| pG1110 | 10–11 | SEQ ID NO: 104 | SEQ ID NO: 116 |
| pG1312 | 12–13 | SEQ ID NO: 107 | SEQ ID NO: 119 |
| pG4948 | 48–49 | SEQ ID NO: 111 | SEQ ID NO: 123 |
| pG5960 | 59–60 | SEQ ID NO: 112 | SEQ ID NO: 124 |
| pG6667 | 66–67 | SEQ ID NO: 113 | SEQ ID NO: 125 |
| pG6869 | 68–69 | SEQ ID NO: 114 | SEQ ID NO: 126 |
| pG123122 | 122–123 | SEQ ID NO: 105 | SEQ ID NO: 117 |
| pG159158 | 158–159 | SEQ ID NO: 108 | SEQ ID NO: 120 |
| pG7170 | 70–71 | SEQ ID NO: 115 | SEQ ID NO: 127 |
| pG125124 | 124–125 | SEQ ID NO: 106 | SEQ ID NO: 118 |
| pG1918 | 18–19 | SEQ ID NO: 109 | SEQ ID NO: 121 |
| pG170169 | 169–170 | SEQ ID NO: 129 | SEQ ID NO: 128 |

Additional techniques for the construction of the variant genes, recombinant protein expression, protein purification, protein characterization, biological activity determination can be found in WO 94/12639, WO 94/12638, WO 95/20976, WO 95/21197, WO 95/20977, WO 95/21254 which are hereby incorporated by reference in their entirety.

All references, patents or applications cited herein are incorporated by reference in their entirety as if written herein.

Various other examples will be apparent to the person skilled in the art after reading the present disclosure without departing from the spirit and scope of the invention. It is intended that all such other examples be included within the scope of the appended claims.

What is claimed is:

1. A method for stimulating the production of hematopoietic cells in a patient in need thereof comprising the step of administering to said patient;
 a human G-CSF receptor agonist polypeptide, comprising a modified G-CSF amino acid sequence selected from the group consisting of:
  (a) the sequence of SEQ ID NO:1; wherein
   Xaa at position 1 is Thr, Ser, Arg, Tyr or Gly;
   Xaa at position 2 is Pro or Leu;
   Xaa at position 3 is Leu, Arg, Tyr or Ser;
   Xaa at position 13 is Phe, Ser, His, Thr or Pro;
   Xaa at position 16 is Lys, Pro, Ser, Thr or His;
   Xaa at position 17 is Cys, Ser, Gly, Ala, Ile, Tyr or Arg;
   Xaa at position 18 is Leu, Thr, Pro, His, Ile or Cys;
   Xaa at position 22 is Arg, Tyr, Ser, Thr or Ala;
   Xaa at position 24 is Ile, Pro, Tyr or Leu;

Xaa at position 27 is Asp, or Gly;
Xaa at position 30 is Ala, Ile, Leu or Gly;
Xaa at position 34 is Lys or Ser;
Xaa at position 36 is Cys;
Xaa at position 42 is Cys;
Xaa at position 43 is His, Thr, Gly, Val, Lys, Trp, Ala, Arg, Cys, or Leu;
Xaa at position 44 is Pro, Gly, Arg, Asp, Val, Ala, His, Trp, Gln, or Thr;
Xaa at position 46 is Glu, Arg, Phe, Arg, Ile or Ala;
Xaa at position 47 is Leu or Thr;
Xaa at position 49 is Leu, Phe, Arg or Ser;
Xaa at position 50 is Leu, Ile, His, Pro or Tyr;
Xaa at position 54 is Leu or His;
Xaa at position 64 is Cys;
Xaa at position 67 is Gln, Lys, Leu or Cys;
Xaa at position 70 is Gln, Pro, Leu, Arg or Ser;
Xaa at position 74 is Cys;
Xaa at position 104 is Asp, Gly or Val;
Xaa at position 108 is Leu, Ala, Val, Arg, Trp, Gln or Gly;
Xaa at position 115 is Thr, His, Leu or Ala;
Xaa at position 120 is Gln, Gly, Arg, Lys or His
Xaa at position 123 is Glu, Arg, Phe or Thr
Xaa at position 144 is Phe, His, Arg, Pro, Leu, Gln or Glu;
Xaa at position 146 is Arg or Gln;
Xaa at position 147 is Arg or Gln;
Xaa at position 156 is His, Gly or Ser;
Xaa at position 159 is Ser, Arg, Thr, Tyr, Val or Gly;
Xaa at position 162 is Glu, Leu, Gly or Trp;
Xaa at position 163 is Val, Gly, Arg or Ala;
Xaa at position 169 is Arg, Ser, Leu, Arg or Cys;
Xaa at position 170 is His, Arg or Ser;
  (b) residues 12–174 of SEQ ID NO:1 according to (a);
  (c) residues 1–169 of SEQ ID NO:1 according to (a); and
  (d) residues 1–169 of SEQ ID NO:1 according to (a);
wherein the N-terminus is joined to the C-terminus directly or through a linker and wherein a new C-terminus and N-terminus are created between the amino acid residue pairs of SEQ ID NO:1 selected from the group consisting of:
  38-39, 39-40, 40-41, 41-42, 42-43, 43-44, 45-46, 48-49, 49-50, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 91-92, 92-93, 93-94, 94-95, 95-96, 96-97, 97-98, 98-99, 99-100, 123-124, 124-125, 125-126, 126-127, 127-128, 128-129, 129-130, 130-131, 131-132, 132-133, 133-134, 134-135, 135-136, 136-137, 137-138, 138-139, 139-140, 140-141, 141-142 and 142-143.

2. The method according to claim 1 wherein said G-CSF receptor agonist polypeptide is immediately preceded by an N-terminal methionine residue, alanine residue or methionine-alanine di-peptide.

3. The method according to claim 1 or 2 wherein in said G-CSF receptor agonist polypeptide said linker is selected from the group consisting of;
  (SEQ ID NO:2), (SEQ ID NO:61), (SEQ ID NO:62), (SEQ ID NO:63), (SEQ ID NO:64), (SEQ ID NO:65), (SEQ ID NO:66), and (SEQ ID NO:67).

4. The method according to claim 1 wherein said G-CSF receptor agonist polypeptide is selected from the group consisting of:
  (SEQ ID NO:48), (SEQ ID NO:49), (SEQ ID NO:50), (SEQ ID NO:51), (SEQ ID NO:52), (SEQ ID NO:118), (SEQ ID NO:123), (SEQ ID NO:124), (SEQ ID NO:125), (SEQ ID NO:126), and (SEQ ID NO:127).

5. The method according to claim 2 wherein said G-CSF receptor agonist polypeptide is selected from the group consisting of:
  Met(SEQ ID NO:48), Met-Ala(SEQ ID NO:48), Ala(SEQ ID NO:48), Met(SEQ ID NO:49), Met-Ala(SEQ ID NO:49), Ala(SEQ ID NO:49), Met(SEQ ID NO:50), Met-Ala(SEQ ID NO:50), Ala(SEQ ID NO:50), Met(SEQ ID NO:51), Met-Ala(SEQ ID NO:51), Ala(SEQ ID NO:51), Met(SEQ ID NO:52), Met-Ala(SEQ ID NO:52), Ala(SEQ ID NO:52), Met(SEQ ID NO:118), Met-Ala(SEQ ID NO:118), Ala(SEQ ID NO:118), Met(SEQ ID NO:123), Met-Ala(SEQ ID NO:123), Ala(SEQ ID NO:123), Met(SEQ ID NO:124), Met-Ala(SEQ ID NO:124), Ala(SEQ ID NO:124), Met(SEQ ID NO:125), Met-Ala(SEQ ID NO:125), Ala(SEQ ID NO:125), Met(SEQ ID NO:126), Met-Ala(SEQ ID NO:126), Ala(SEQ ID NO:126) Met(SEQ ID NO:127), Met-Ala(SEQ ID NO:127) and Ala(SEQ ID NO:127).

6. A method for stimulating the production of hematopoietic cells in a patient in need thereof comprising the step of administering to said patient a composition comprising;
  a human G-CSF receptor agonist polypeptide, comprising a modified G-CSF amino acid sequence selected from the group consisting of:
  (a) the sequence of SEQ ID NO:1; wherein
    Xaa at position 1 is Thr, Ser, Arg, Tyr or Gly;
    Xaa at position 2 is Pro or Leu;
    Xaa at position 3 is Leu, Arg, Tyr or Ser;
    Xaa at position 13 is Phe, Ser, His, Thr or Pro;
    Xaa at position 16 is Lys, Pro, Ser, Thr or His;
    Xaa at position 17 is Cys, Ser, Gly, Ala, Ile, Tyr or Arg;
    Xaa at position 18 is Leu, Thr, Pro, His, Ile or Cys;
    Xaa at position 22 is Arg, Tyr, Ser, Thr or Ala;
    Xaa at position 24 is Ile, Pro, Tyr or Leu;
    Xaa at position 27 is Asp, or Gly;
    Xaa at position 30 is Ala, Ile, Leu or Gly;
    Xaa at position 34 is Lys or Ser;
    Xaa at position 36 is Cys;
    Xaa at position 42 is Cys;
    Xaa at position 43 is His, Thr, Gly, Val, Lys, Trp, Ala, Arg, Cys, or Leu;
    Xaa at position 44 is Pro, Gly, Arg, Asp, Val, Ala, His, Trp, Gln, or Thr;
    Xaa at position 46 is Glu, Arg, Phe, Arg, Ile or Ala;
    Xaa at position 47 is Leu or Thr;
    Xaa at position 49 is Leu, Phe, Arg or Ser;
    Xaa at position 50 is Leu, Ile, His, Pro or Tyr;
    Xaa at position 54 is Leu or His;
    Xaa at position 64 is Cys;
    Xaa at position 67 is Gln, Lys, Leu or Cys;
    Xaa at position 70 is Gln, Pro, Leu, Arg or Ser;
    Xaa at position 74 is Cys;
    Xaa at position 104 is Asp, Gly or Val;
    Xaa at position 108 is Leu, Ala, Val, Arg, Trp, Gln or Gly;
    Xaa at position 115 is Thr, His, Leu or Ala;
    Xaa at position 120 is Gln, Gly, Arg, Lys or His
    Xaa at position 123 is Glu, Arg, Phe or Thr
    Xaa at position 144 is Phe, His, Arg, Pro, Leu, Gln or Glu;
    Xaa at position 146 is Arg or Gln;
    Xaa at position 147 is Arg or Gln;
    Xaa at position 156 is His, Gly or Ser;
    Xaa at position 159 is Ser, Arg, Thr, Tyr, Val or Gly;
    Xaa at position 162 is Glu, Leu, Gly or Trp;
    Xaa at position 163 is Val, Gly, Arg or Ala;

Xaa at position 169 is Arg, Ser, Leu, Arg or Cys;
Xaa at position 170 is His, Arg or Ser;
(b) residues 12-174 of SEQ ID NO:1 according to (a);
(c) residues 1-169 of SEQ ID NO:1 according to (a); and
(d) residues 1-169 of SEQ ID NO:1 according to (a);
wherein the N-terminus is joined to the C-terminus directly or through a linker and wherein a new C-terminus and N-terminus are created between the amino acid residue pairs of SEQ ID NO:1 selected from the group consisting of:
38-39, 39-40, 40-41, 41-42, 42-43, 43-44, 45-46, 48-49, 49-50, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 91-92, 92-93, 93-94, 94-95, 95-96, 96-97, 97-98, 98-99, 99-100, 123-124, 124-125, 125-126, 126-127, 127-128, 128-129, 129-130, 130-131, 131-132, 132-133, 133-134, 134-135, 135-136, 136-137, 137-138, 138-139, 139-140, 140-141, 141-142 and 142-143; and
a pharmaceutically acceptable carrier.

7. The method according to claim 6 wherein said G-CSF receptor agonist polypeptide is immediately preceded by an N-terminal methionine residue, alanine residue or methionine-alanine di-peptide.

8. The method according to claim 6 or 7 wherein in said G-CSF receptor agonist polypeptide said linker is selected from the group consisting of;
(SEQ ID NO:2), (SEQ ID NO:61), (SEQ ID NO:62), (SEQ ID NO:63), (SEQ ID NO:64), (SEQ ID NO:65), (SEQ ID NO:66), and (SEQ ID NO:67).

9. The method according to claim 6 wherein said G-CSF receptor agonist polypeptide is selected from the group consisting of:
(SEQ ID NO:48), (SEQ ID NO:49), (SEQ ID NO:50), (SEQ ID NO:51), (SEQ ID NO:52), (SEQ ID NO:118), (SEQ ID NO:123), (SEQ ID NO:124),(SEQ ID NO:125),(SEQ ID NO:126), and (SEQ ID NO:127).

10. The method according to claim 7 wherein said G-CSF receptor agonist polypeptide is selected from the group consisting of:
Met(SEQ ID NO:48), Met-Ala(SEQ ID NO:48), Ala(SEQ ID NO:48), Met(SEQ ID NO:49), Met-Ala(SEQ ID NO:49), Ala(SEQ ID NO:49), Met(SEQ ID NO:50), Met-Ala(SEQ ID NO:50), Ala(SEQ ID NO:50), Met (SEQ ID NO:51), Met-Ala(SEQ ID NO:51), Ala(SEQ ID NO:51), Met(SEQ ID NO:52), Met-Ala(SEQ ID NO:52), Ala(SEQ ID NO:52), Met(SEQ ID NO:118), Met-Ala(SEQ ID NO:118), Ala(SEQ ID NO:118), Met (SEQ ID NO:123), Met-Ala(SEQ ID NO:123), Ala (SEQ ID NO:123), Met(SEQ ID NO:124), Met-Ala (SEQ ID NO:124), Ala(SEQ ID NO:124), Met(SEQ ID NO:125), Met-Ala(SEQ ID NO:125), Ala(SEQ ID NO:125), Met(SEQ ID NO:126), Met-Ala(SEQ ID NO:126), Ala(SEQ ID NO:126) Met(SEQ ID NO:127), Met-Ala(SEQ ID NO:127) and Ala(SEQ ID NO:127).

11. A method for stimulating the production of hematopoietic cells in a patient in need thereof comprising the step of administering to said patient a composition comprising;
a human G-CSF receptor agonist polypeptide, comprising a modified G-CSF amino acid sequence selected from the group consisting of:
(a) the sequence of SEQ ID NO:1; wherein
Xaa at position 1 is Thr, Ser, Arg, Tyr or Gly;
Xaa at position 2 is Pro or Leu;
Xaa at position 3 is Leu, Arg, Tyr or Ser;
Xaa at position 13 is Phe, Ser, His, Thr or Pro;
Xaa at position 16 is Lys, Pro, Ser, Thr or His;
Xaa at position 17 is Cys, Ser, Gly, Ala, Ile, Tyr or Arg;
Xaa at position 18 is Leu, Thr, Pro, His, Ile or Cys;
Xaa at position 22 is Arg, Tyr, Ser, Thr or Ala;
Xaa at position 24 is Ile, Pro, Tyr or Leu;
Xaa at position 27 is Asp, or Gly;
Xaa at position 30 is Ala, Ile, Leu or Gly;
Xaa at position 34 is Lys or Ser;
Xaa at position 36 is Cys;
Xaa at position 42 is Cys;
Xaa at position 43 is His, Thr, Gly, Val, Lys, Trp, Ala, Arg, Cys, or Leu;
Xaa at position 44 is Pro, Gly, Arg, Asp, Val, Ala, His, Trp, Gln, or Thr;
Xaa at position 46 is Glu, Arg, Phe, Arg, Ile or Ala;
Xaa at position 47 is Leu or Thr;
Xaa at position 49 is Leu, Phe, Arg or Ser;
Xaa at position 50 is Leu, Ile, His, Pro or Tyr;
Xaa at position 54 is Leu or His;
Xaa at position 64 is Cys;
Xaa at position 67 is Gln, Lys, Leu or Cys;
Xaa at position 70 is Gln, Pro, Leu, Arg or Ser;
Xaa at position 74 is Cys;
Xaa at position 104 is Asp, Gly or Val;
Xaa at position 108 is Leu, Ala, Val, Arg, Trp, Gln or Gly;
Xaa at position 115 is Thr, His, Leu or Ala;
Xaa at position 120 is Gln, Gly, Arg, Lys or His;
Xaa at position 123 is Glu, Arg, Phe or Thr;
Xaa at position 144 is Phe, His, Arg, Pro, Leu, Gln or Glu;
Xaa at position 146 is Arg or Gln;
Xaa at position 147 is Arg or Gln;
Xaa at position 156 is His, Gly or Ser;
Xaa at position 159 is Ser, Arg, Thr, Tyr, Val or Gly;
Xaa at position 162 is Glu, Leu, Gly or Trp;
Xaa at position 163 is Val, Gly, Arg or Ala;
Xaa at position 169 is Arg, Ser, Leu, Arg or Cys;
Xaa at position 170 is His, Arg or Ser;
(b) residues 12-174 of SEQ ID NO:1 according to (a);
(c) residues 1-169 of SEQ ID NO:1 according to (a); and
(d) residues 1-169 of SEQ ID NO:1 according to (a);
wherein the N-terminus is joined to the C-terminus directly or through a linker and wherein a new C-terminus and N-terminus are created between the amino acid residue pairs of SEQ ID NO:1 selected from the group consisting of:
38-39, 39-40, 40-41, 41-42, 42-43, 43-44, 45-46, 48-49, 49-50, 52-53, 53-54, 54-55, 55-56, 56-57, 57-58, 58-59, 59-60, 60-61, 61-62, 62-63, 63-64, 64-65, 65-66, 66-67, 67-68, 68-69, 69-70, 70-71, 71-72, 91-92, 92-93, 93-94, 94-95, 95-96, 96-97, 97-98, 98-99, 99-100, 123-124, 124-125, 125-126, 126-127, 127-128, 128-129, 129-130, 130-131, 131-132, 132-133, 133-134, 134-135, 135-136, 136-137, 137-138, 138-139, 139-140, 140-141, 141-142 and 142-143;
a colony stimulating factor selected from the group consisting of:
GM-CSF, c-mpl ligand, M-CSF, erythropoietin IL-1, IL-2, IL-3, IL-4, IL-5, IL-6, IL-7, IL-8, IL-9, IL-10, IL-11, IL-12, IL-13, IL-15, LIF, flt3 ligand and stem cell factor; and
a pharmaceutically acceptable carrier.

12. The method according to claim 11 wherein said G-CSF receptor agonist polypeptide is immediately preceded by an N-terminal methionine residue, alanine residue or methionine-alanine di-peptide.

13. The method according to claim 11 or 12 wherein in said G-CSF receptor agonist polypeptide said linker is selected from the group consisting of;

(SEQ ID NO:2), (SEQ ID NO:61), (SEQ ID NO:62), (SEQ ID NO:63), (SEQ ID NO:64), (SEQ ID NO:65), (SEQ ID NO:66), and (SEQ ID NO:67).

14. The method according to claim 11 wherein said G-CSF receptor agonist polypeptide is selected from the group consisting of:

(SEQ ID NO:48), (SEQ ID NO:49), (SEQ ID NO:50), (SEQ ID NO:51), (SEQ ID NO:52), (SEQ ID NO:118), (SEQ ID NO:123), (SEQ ID NO:124), (SEQ ID NO:125), (SEQ ID NO:126), and (SEQ ID NO:127).

15. The method according to claim 12 wherein said G-CSF receptor agonist polypeptide is selected from the group consisting of:

Met(SEQ ID NO:48), Met-Ala(SEQ ID NO:48), Ala(SEQ ID NO:48), Met(SEQ ID NO:49), Met-Ala(SEQ ID NO:49), Ala(SEQ ID NO:49), Met(SEQ ID NO:50), Met-Ala(SEQ ID NO:50), Ala(SEQ ID NO:50), Met(SEQ ID NO:51), Met-Ala(SEQ ID NO:51), Ala(SEQ ID NO:51), Met(SEQ ID NO:52), Met-Ala(SEQ ID NO:52), Ala(SEQ ID NO:52), Met(SEQ ID NO:118), Met-Ala(SEQ ID NO:118), Ala(SEQ ID NO:118), Met(SEQ ID NO:123), Met-Ala(SEQ ID NO:123), Ala(SEQ ID NO:123), Met(SEQ ID NO:124), Met-Ala(SEQ ID NO:124), Ala(SEQ ID NO:124), Met(SEQ ID NO:125), Met-Ala(SEQ ID NO:125), Ala(SEQ ID NO:125), Met(SEQ ID NO:126), Met-Ala(SEQ ID NO:126), Ala(SEQ ID NO:126) Met(SEQ ID NO:127), Met-Ala(SEQ ID NO:127) and Ala(SEQ ID NO:127).

\* \* \* \* \*

UNITED STATES PATENT AND TRADEMARK OFFICE
CERTIFICATE OF CORRECTION

PATENT NO. : 6,358,505 B1
DATED : March 19, 2002
INVENTOR(S) : Zurfluh et al.

It is certified that error appears in the above-identified patent and that said Letters Patent is hereby corrected as shown below:

Title page,
Item [63], Related U.S. Application Data, replace "Provisional application No. 60/004,382, filed on Sep. 27, 1995." with -- Provisional application No. 60/004,832, filed on Oct. 5, 1995. --

Column 1,
Lines 7-8, replace "U.S. provisional application Ser. No. 60/004,382 filed Sep. 27, 1995." with -- U.S. provisional application Ser. No. 60/004,832 filed Oct. 05, 1995. --

Signed and Sealed this

Twenty-ninth Day of June, 2004

JON W. DUDAS
*Acting Director of the United States Patent and Trademark Office*